(12) United States Patent
Deutschle et al.

(10) Patent No.: US 10,011,381 B2
(45) Date of Patent: Jul. 3, 2018

(54) PROCESS AND APPARATUS FOR THE TREATMENT OR PROCESSING OF CONTAINERS FOR SUBSTANCES FOR MEDICAL, PHARMACEUTICAL OR COSMETIC APPLICATIONS

(71) Applicant: SCHOTT AG, Mainz (DE)

(72) Inventors: Gregor Fritz Deutschle, Wiesbaden (DE); Joern Wassenberg, Mainz (DE); Alexander Wansel, Wiesbaden (DE); Kai Wissner, Hirschberg (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 14/712,949

(22) Filed: May 15, 2015

(65) Prior Publication Data

US 2017/0197745 A1 Jul. 13, 2017

Related U.S. Application Data

(63) Continuation of application No. 14/710,394, filed on May 12, 2015, and a continuation of application No. PCT/EP2013/003164, filed on Oct. 21, 2013.

(30) Foreign Application Priority Data

Nov. 12, 2012 (DE) .................. 10 2012 110 866

(51) Int. Cl.
*B65B 43/46* (2006.01)
*B65B 3/00* (2006.01)
(Continued)

(52) U.S. Cl.
CPC ............... *B65B 43/46* (2013.01); *B01L 9/06* (2013.01); *B65B 3/003* (2013.01); *B65B 7/2821* (2013.01);
(Continued)

(58) Field of Classification Search
CPC ....... B65B 43/46; B65B 3/003; B65B 7/2821; B65B 43/59; B65B 63/08; G01G 17/06; F26B 35/06; B01L 9/06
See application file for complete search history.

(56) References Cited

U.S. PATENT DOCUMENTS

| 3,939,626 A | 2/1976 | Cioni et al. | |
| 5,964,043 A * | 10/1999 | Oughton | F26B 5/06 34/284 |

(Continued)

FOREIGN PATENT DOCUMENTS

| CN | 1433939 | 8/2003 |
| CN | 101128177 | 2/2008 |

(Continued)

OTHER PUBLICATIONS

English translation of the International Preliminary Report on Patentability dated May 12, 2015 for corresponding International Application No. PCT/EP2013/03164, 17 pages.

(Continued)

*Primary Examiner* — Michelle Lopez
*Assistant Examiner* — Chinyere Rushing-Tucker
(74) *Attorney, Agent, or Firm* — Ohlandt, Greeley, Ruggiero & Perle, L.L.P.

(57) ABSTRACT

Disclosed is a process for the treatment or processing of containers that serve for storing, or contain, substances for medical, pharmaceutical or cosmetic applications, wherein the containers are conveyed automatically, by a conveyor, past at least one processing station or pass it for the treatment or processing. In the process, a plurality of containers is conveyed by the conveyor while being held by a carrier in a regular arrangement. The containers held on the carrier are raised to a raised position for the treatment or processing at or in the respective processing station and are lowered after the treatment or processing, to be held again (Continued)

on the carrier in the regular arrangement. The carrier is configured such that the containers can be held on the carrier during the entire process. A negative pressure acts on the bottoms of the containers in order to lower them.

28 Claims, 59 Drawing Sheets

(51) Int. Cl.
  *B65B 7/28* (2006.01)
  *B65B 43/59* (2006.01)
  *B65B 63/08* (2006.01)
  *G01G 17/06* (2006.01)
  *F26B 5/06* (2006.01)
  *B01L 9/06* (2006.01)

(52) U.S. Cl.
  CPC ............. *B65B 43/59* (2013.01); *B65B 63/08* (2013.01); *F26B 5/06* (2013.01); *G01G 17/06* (2013.01); *B01L 2200/025* (2013.01); *B01L 2200/028* (2013.01)

(56) References Cited

U.S. PATENT DOCUMENTS

| | | | |
|---|---|---|---|
| 8,100,263 B2 | 1/2012 | Vanderbush et al. | |
| 8,118,167 B2 | 2/2012 | Togashi et al. | |
| 2001/0052416 A1 | 12/2001 | Heinz et al. | |
| 2004/0195074 A1 | 10/2004 | Iwasa | |
| 2006/0136095 A1 | 6/2006 | Rob | |
| 2006/0191240 A1* | 8/2006 | Rothbauer | A61J 3/074 53/471 |
| 2006/0266719 A1* | 11/2006 | Knight | B01L 9/06 211/74 |
| 2007/0125442 A1* | 6/2007 | Tribble | B65B 3/003 141/27 |
| 2008/0072996 A1* | 3/2008 | Py | A61J 1/18 141/329 |
| 2008/0184671 A1 | 8/2008 | Fleckenstein et al. | |
| 2009/0158612 A1 | 6/2009 | Thilly et al. | |
| 2011/0197990 A1 | 8/2011 | Poole | |
| 2014/0196411 A1* | 7/2014 | Procyshyn | B25J 21/02 53/467 |
| 2014/0238528 A1 | 8/2014 | Spreizer | |
| 2014/0318875 A1 | 10/2014 | Poole | |
| 2015/0354894 A1* | 12/2015 | Corbin | F26B 5/06 34/296 |
| 2016/0116212 A1* | 4/2016 | Trebbi | F26B 5/06 414/222.01 |

FOREIGN PATENT DOCUMENTS

| | | |
|---|---|---|
| CN | 101244767 | 8/2008 |
| CN | 101804225 | 8/2010 |
| CN | 101855139 | 10/2010 |
| DE | 933708 B | 9/1955 |
| DE | 965156 B | 6/1957 |
| DE | 2439405 A1 | 3/1975 |
| DE | 10028823 A1 | 12/2001 |
| DE | 10242118 A1 | 11/2003 |
| DE | 102004035061 A1 | 2/2006 |
| DE | 102005014116 A1 | 9/2006 |
| DE | 102010060308 A1 | 5/2012 |
| EP | 0588908 B1 | 8/1997 |
| EP | 1138390 | 10/2001 |
| EP | 1061975 B1 | 2/2004 |
| WO | 2007061987 A2 | 5/2007 |
| WO | 2009015862 A1 | 2/2009 |
| WO | 2011110872 A1 | 9/2011 |
| WO | 2011135085 A1 | 11/2011 |

OTHER PUBLICATIONS

English translation of the International Search Report dated May 6, 2014 for corresponding International Application No. PCT/EP2013/03164.

English translation of the Written Opinion of the International Search Authority dated May 6, 2014 for corresponding International Application No. PCT/EP2013/03164.

\* cited by examiner

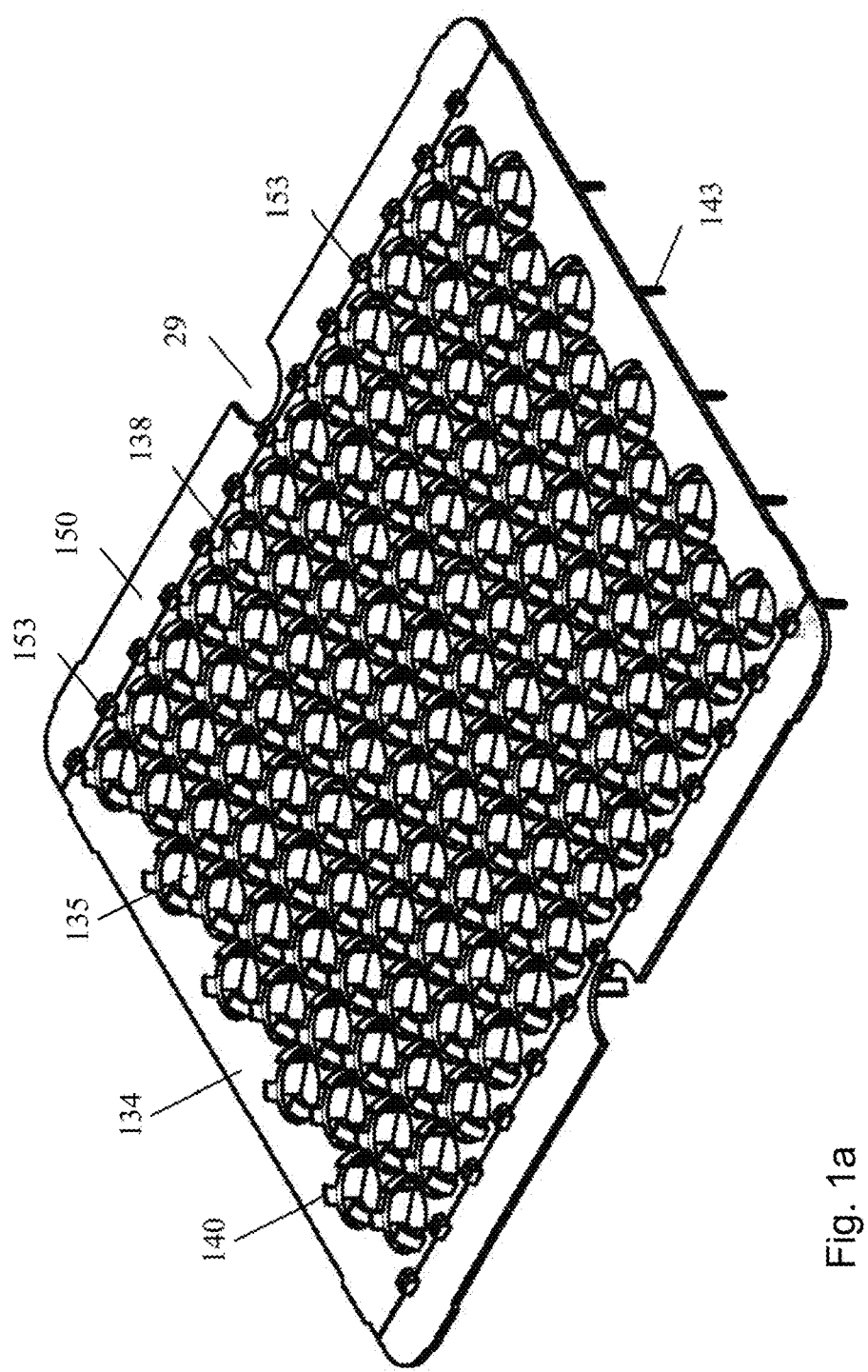

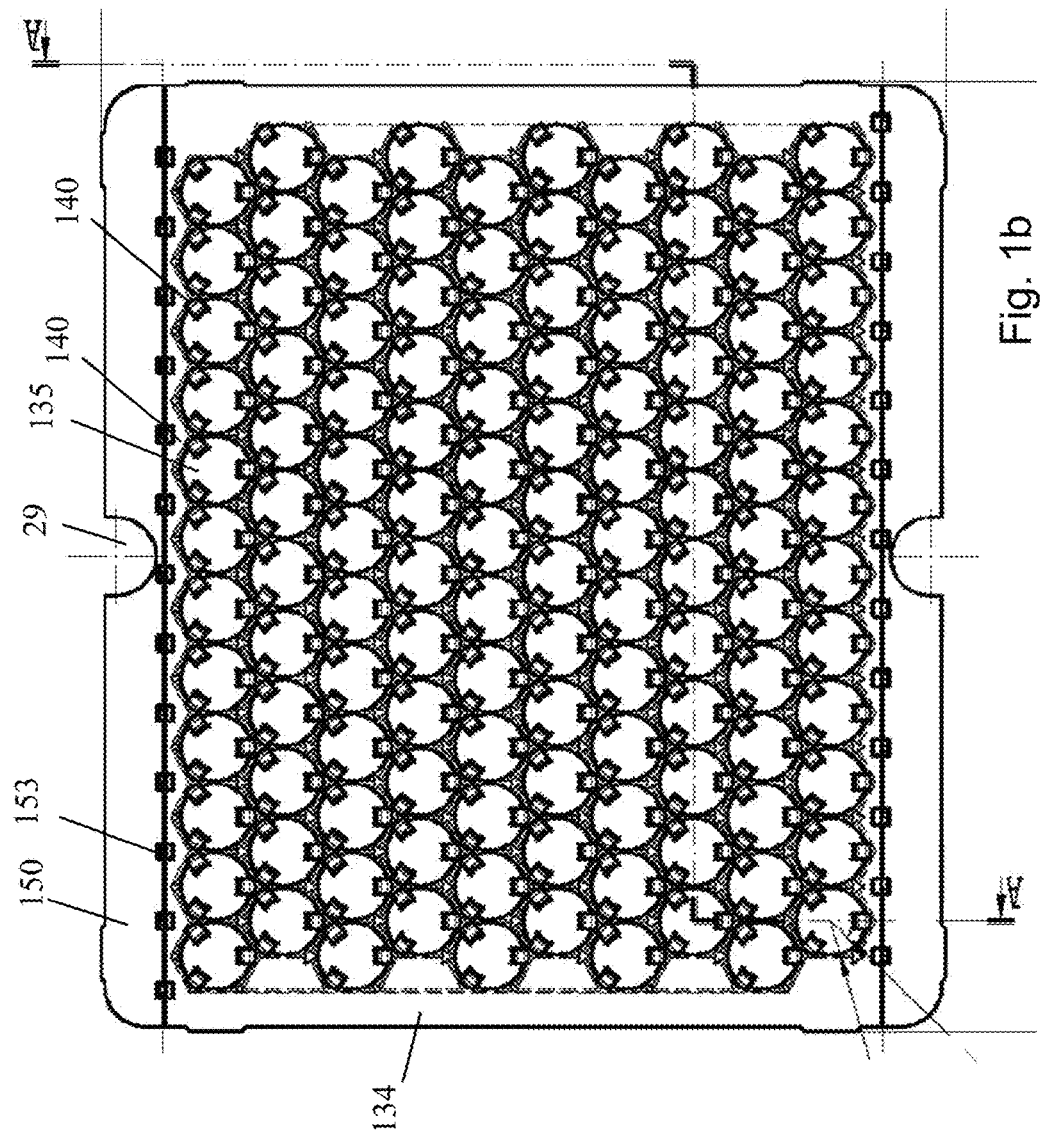

A

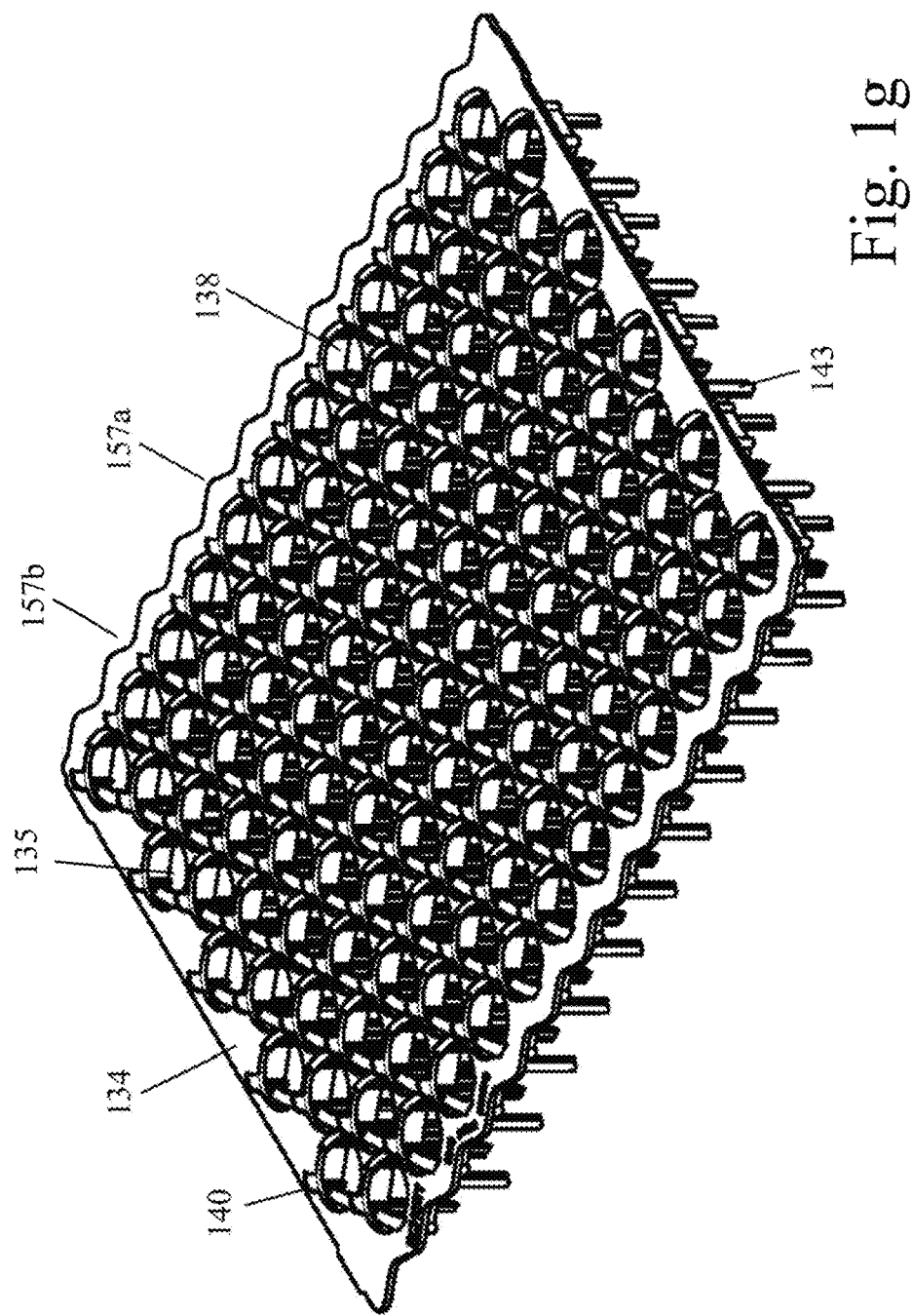

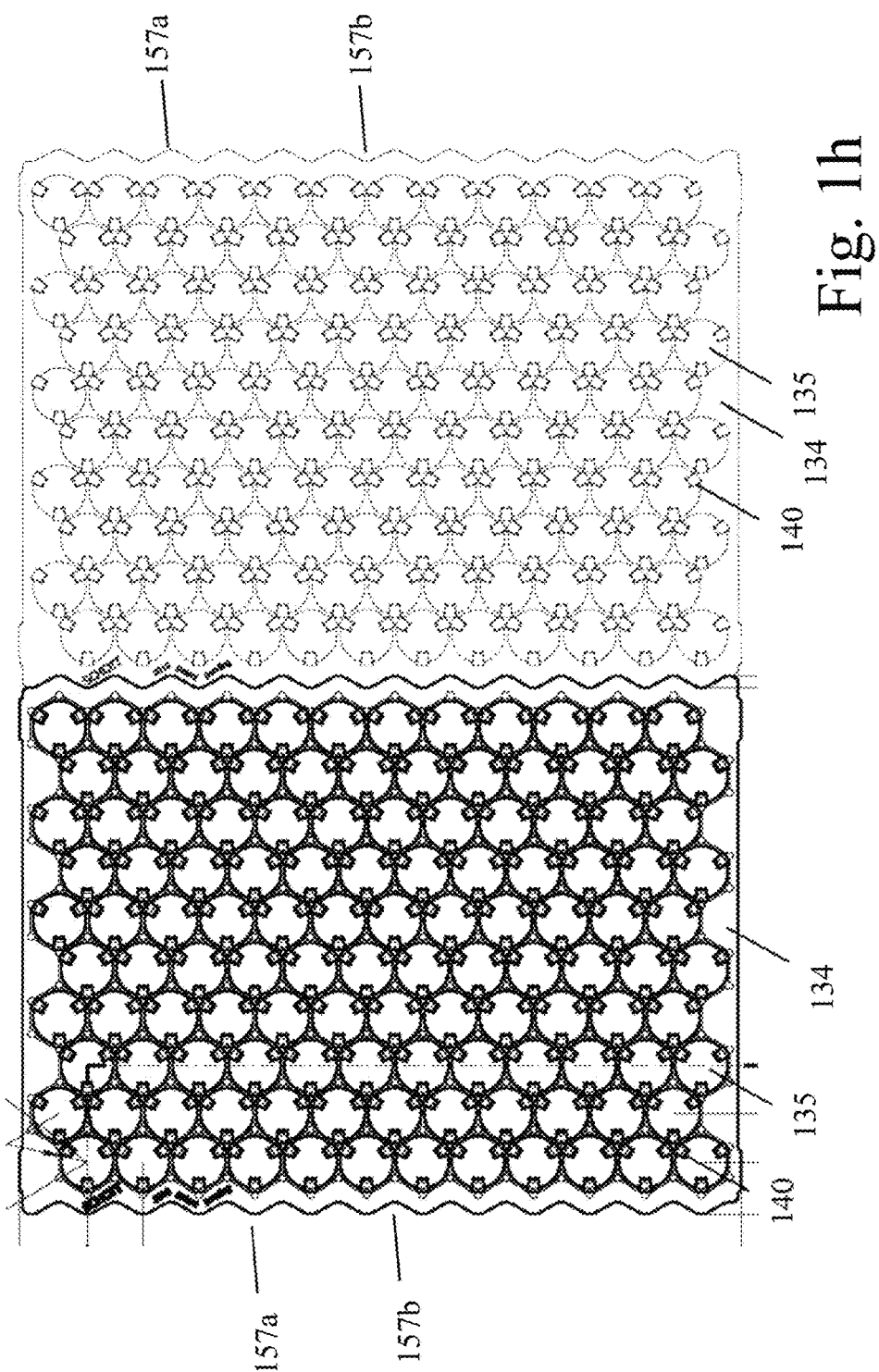

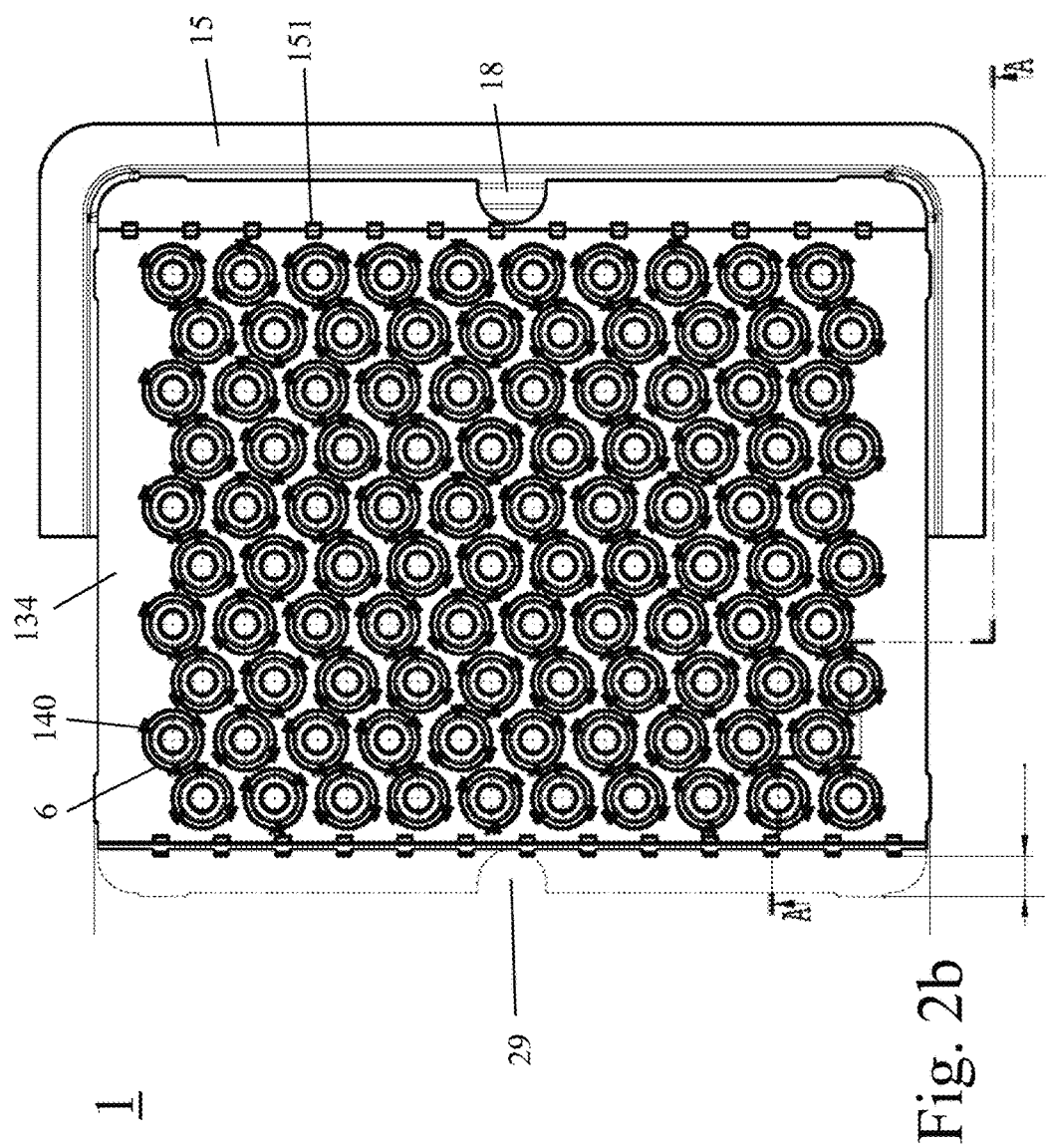

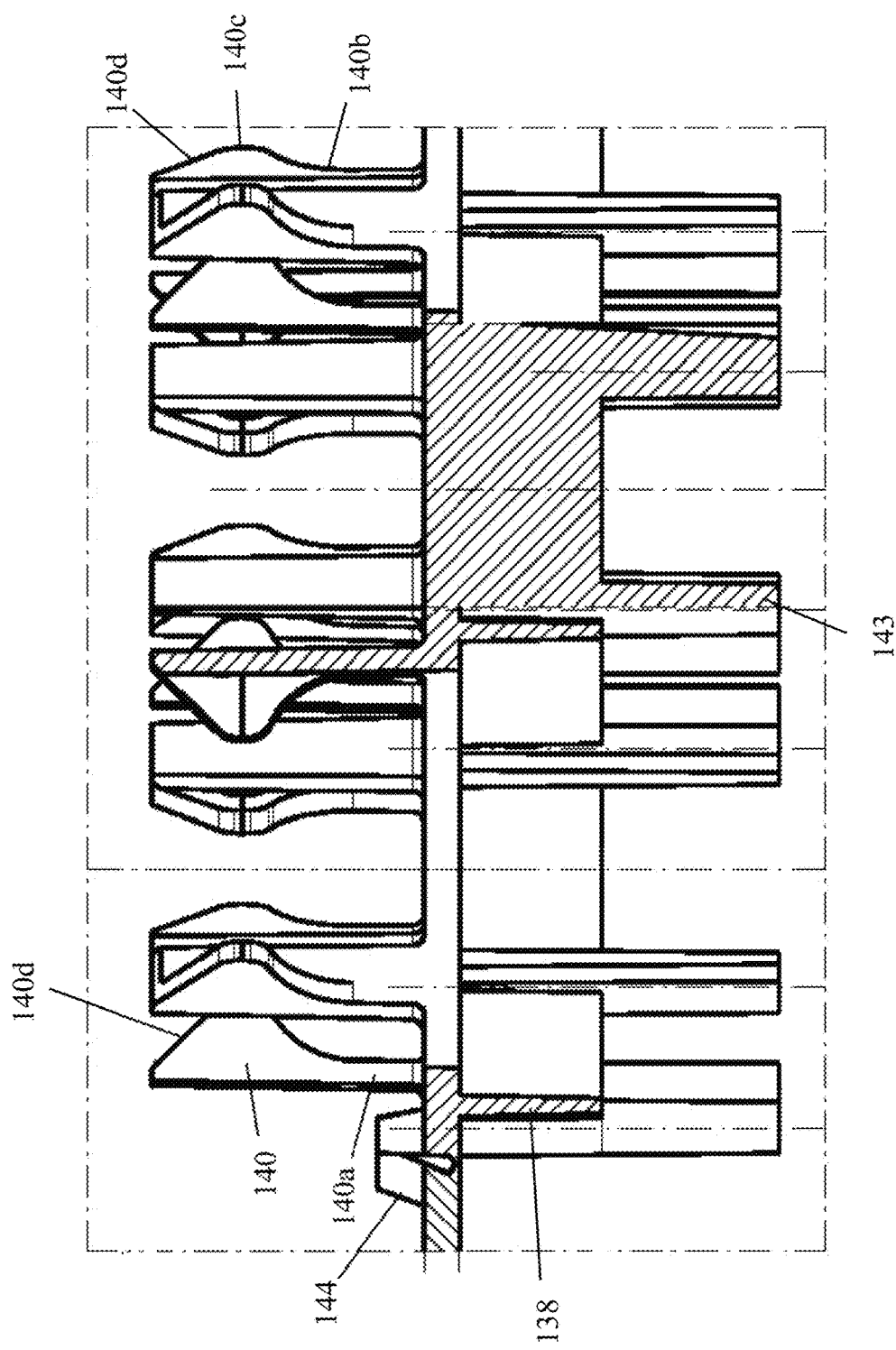

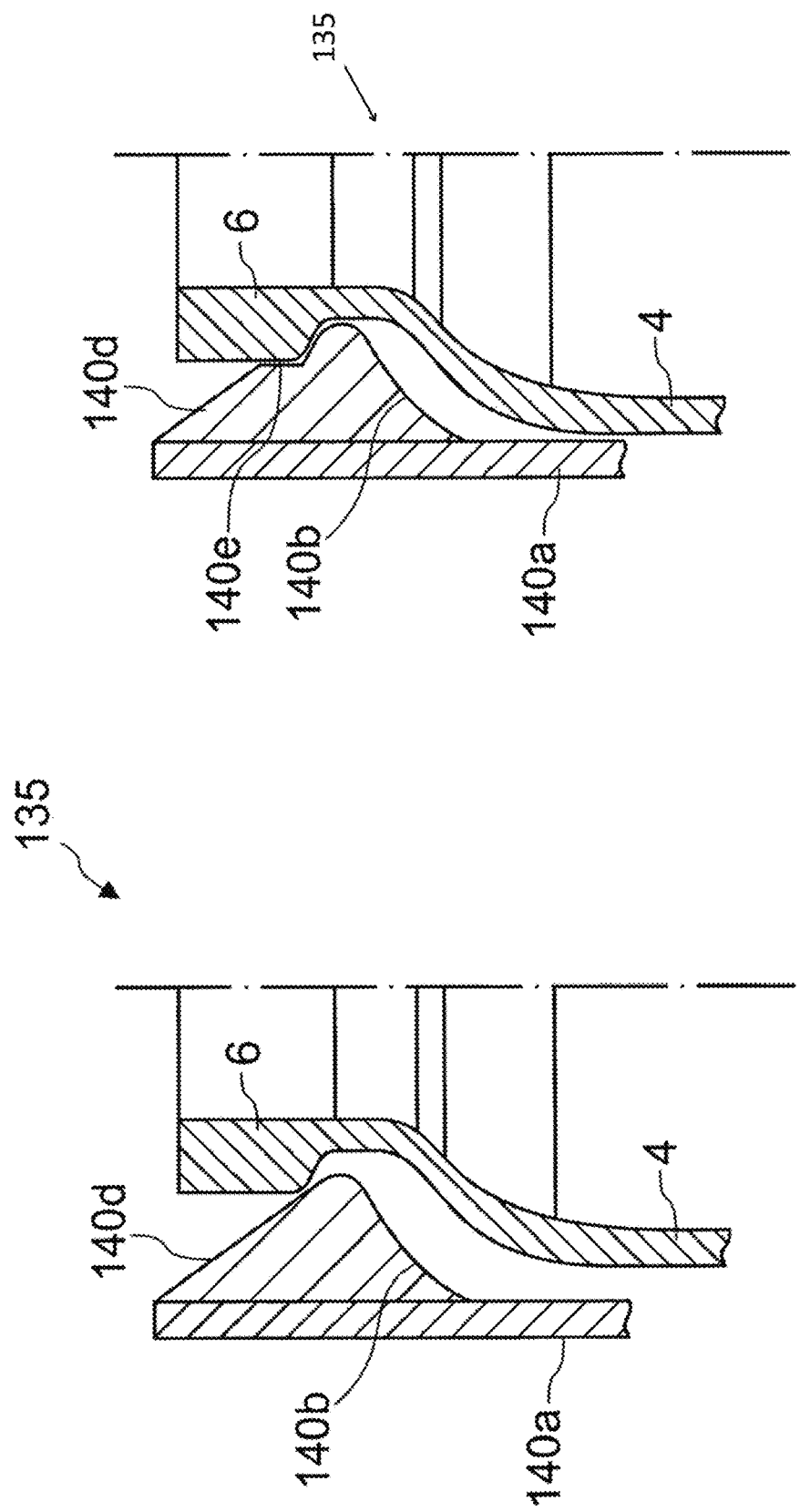

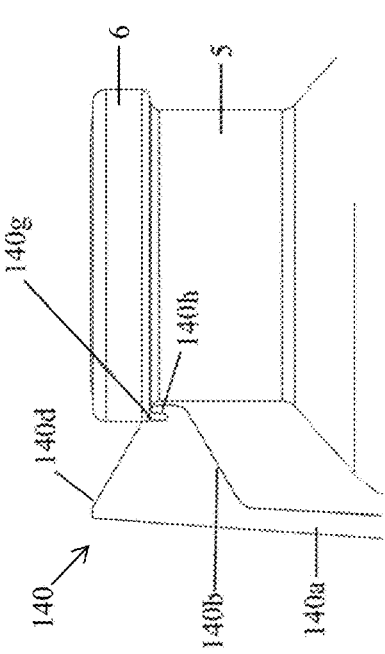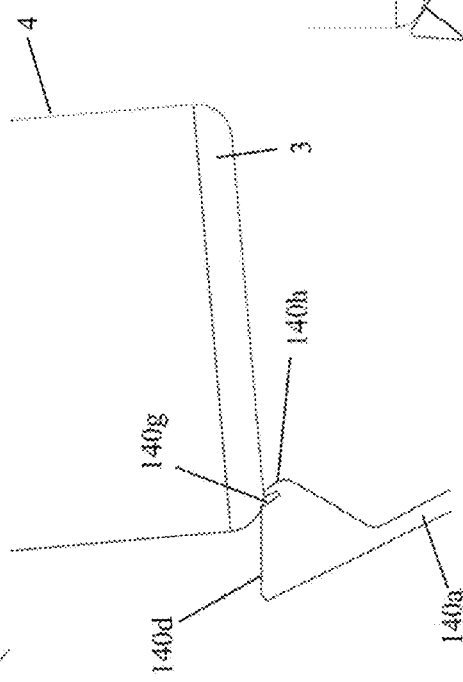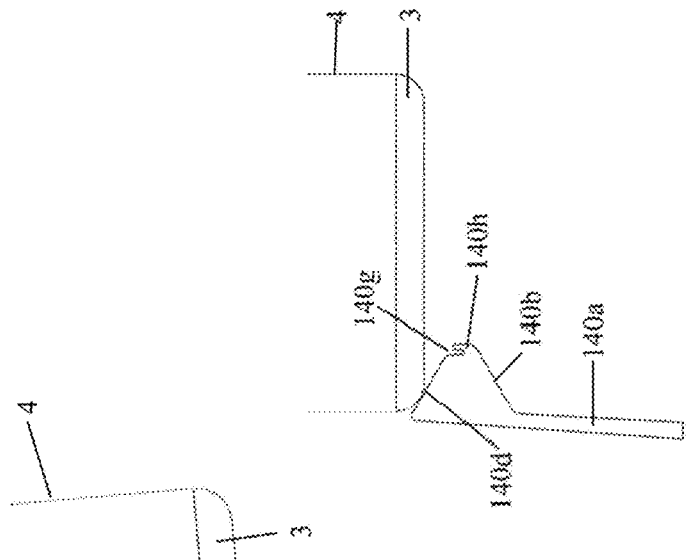

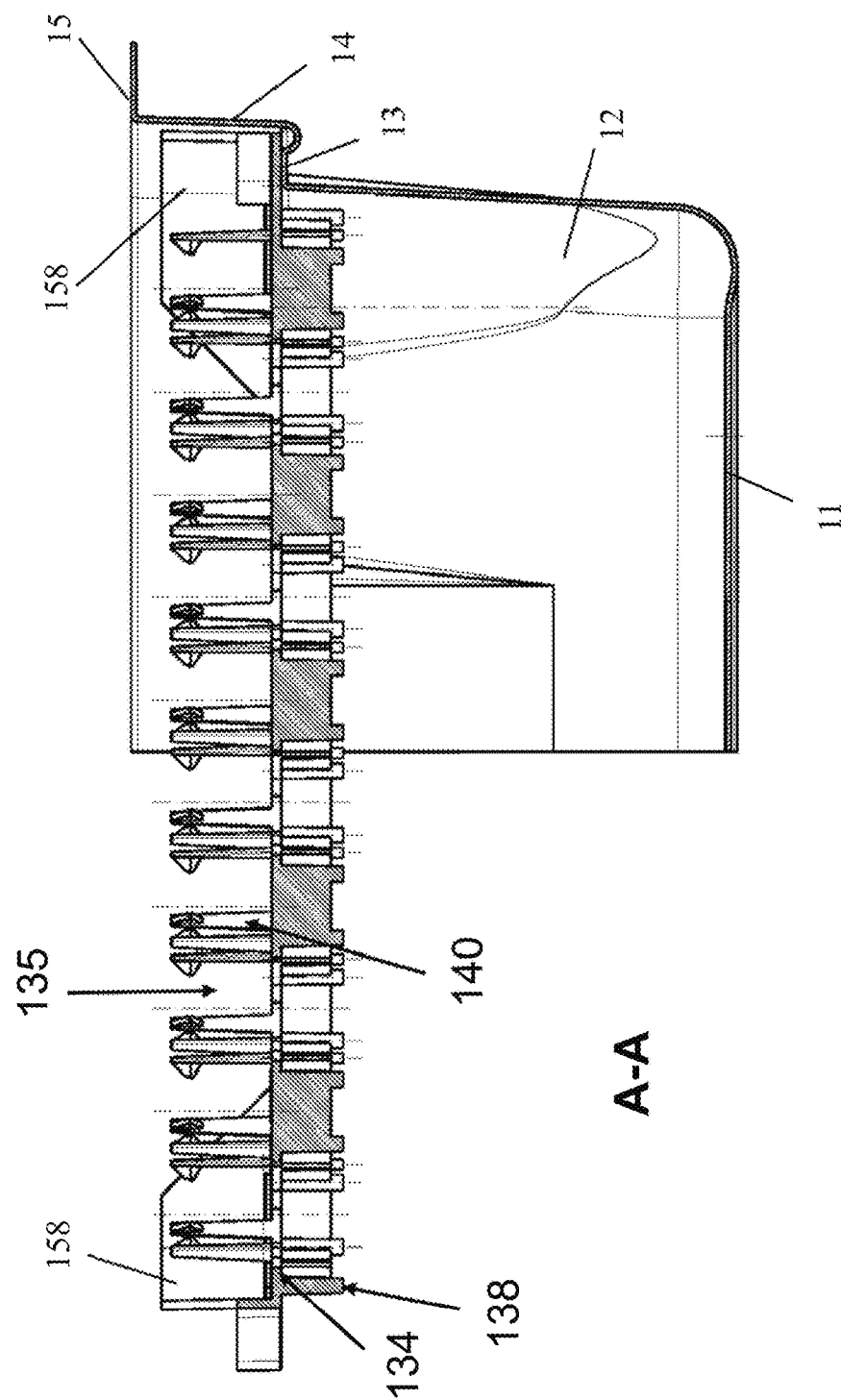

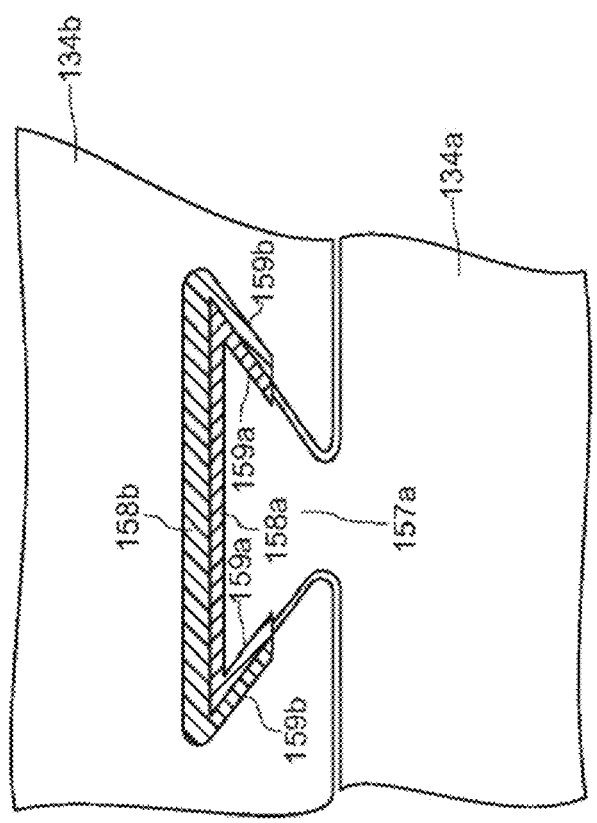

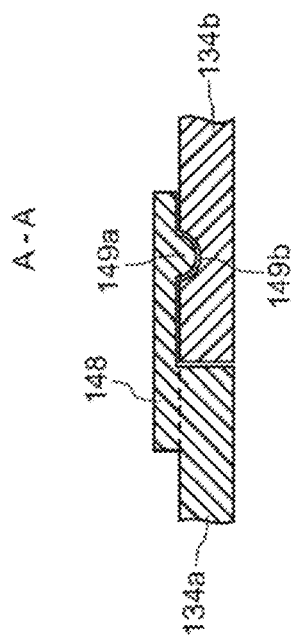
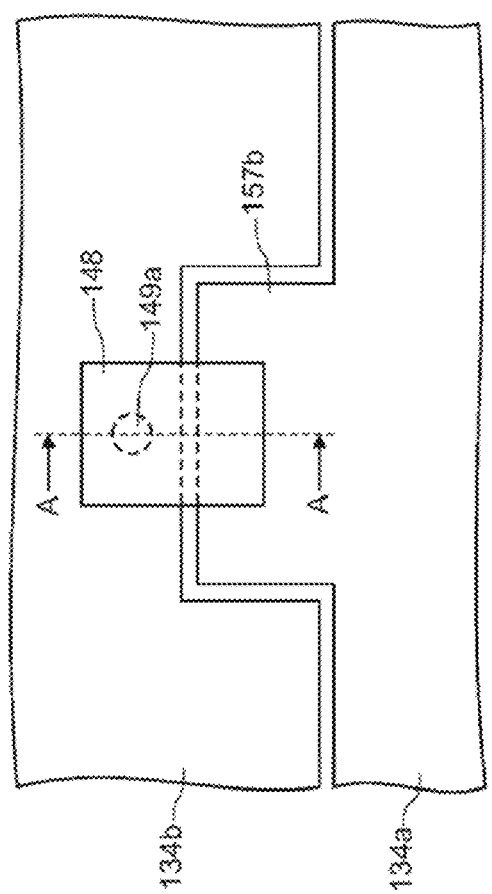

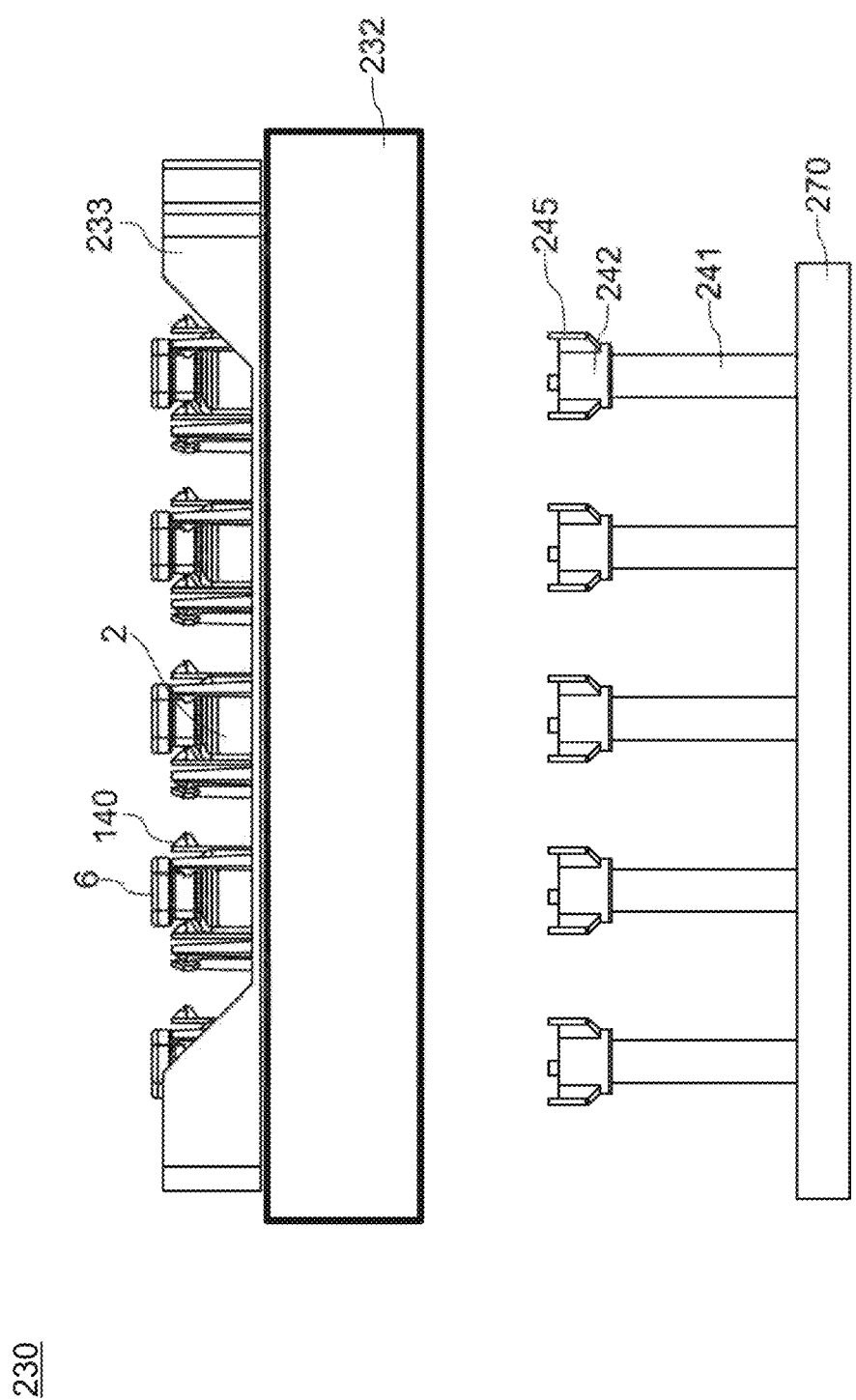

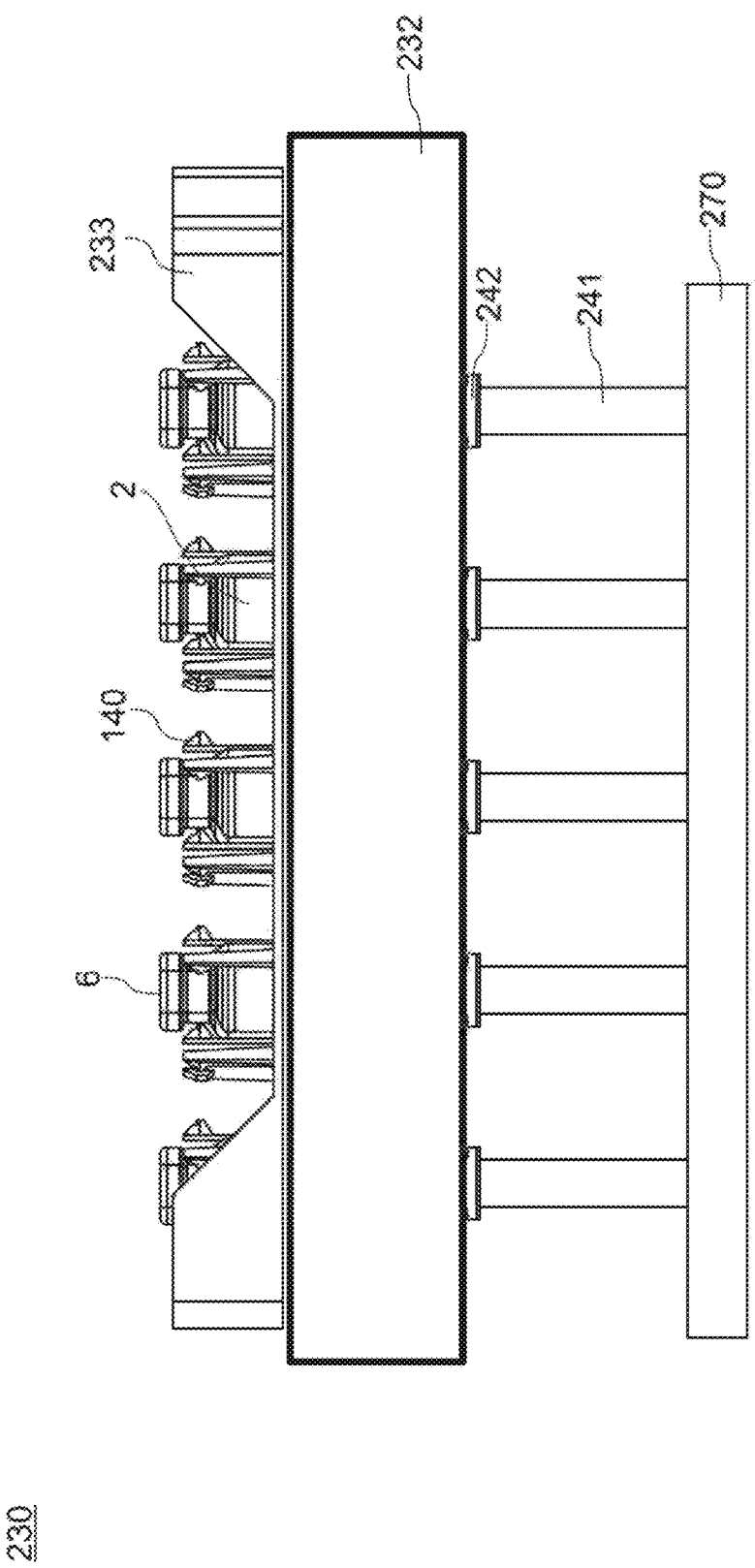

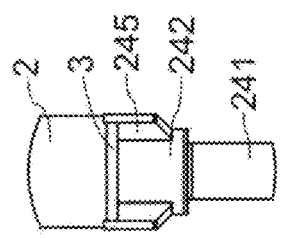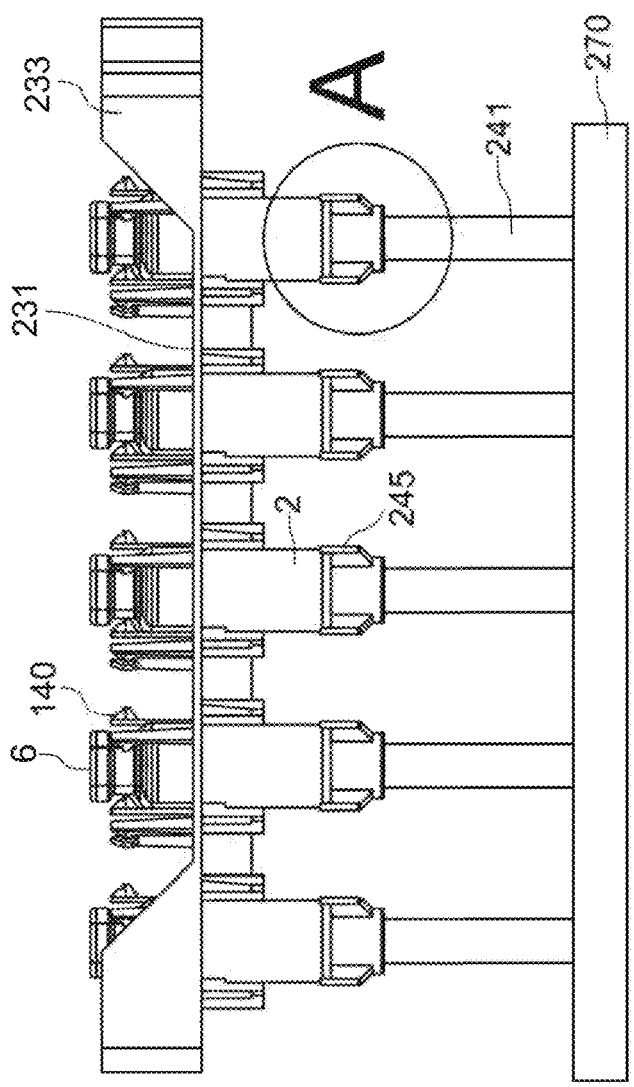

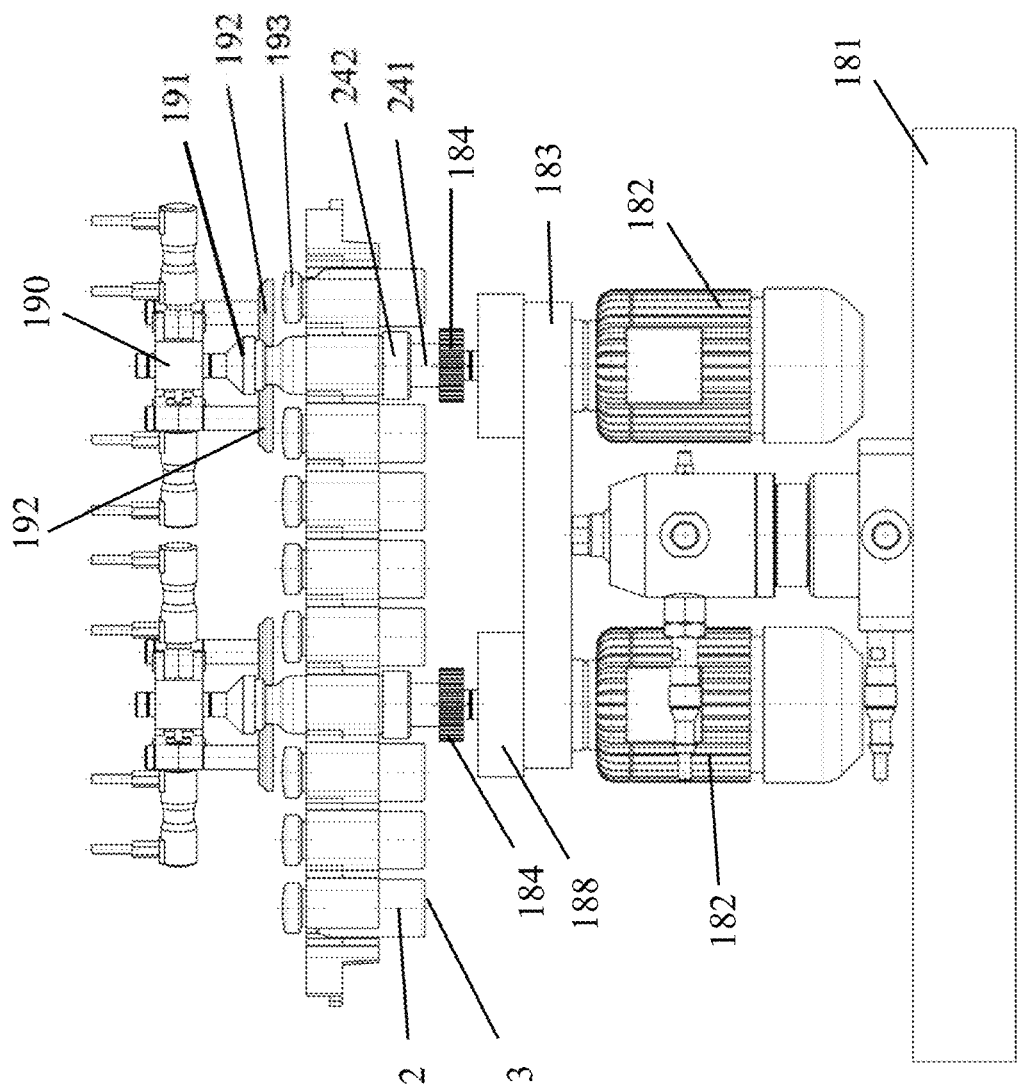

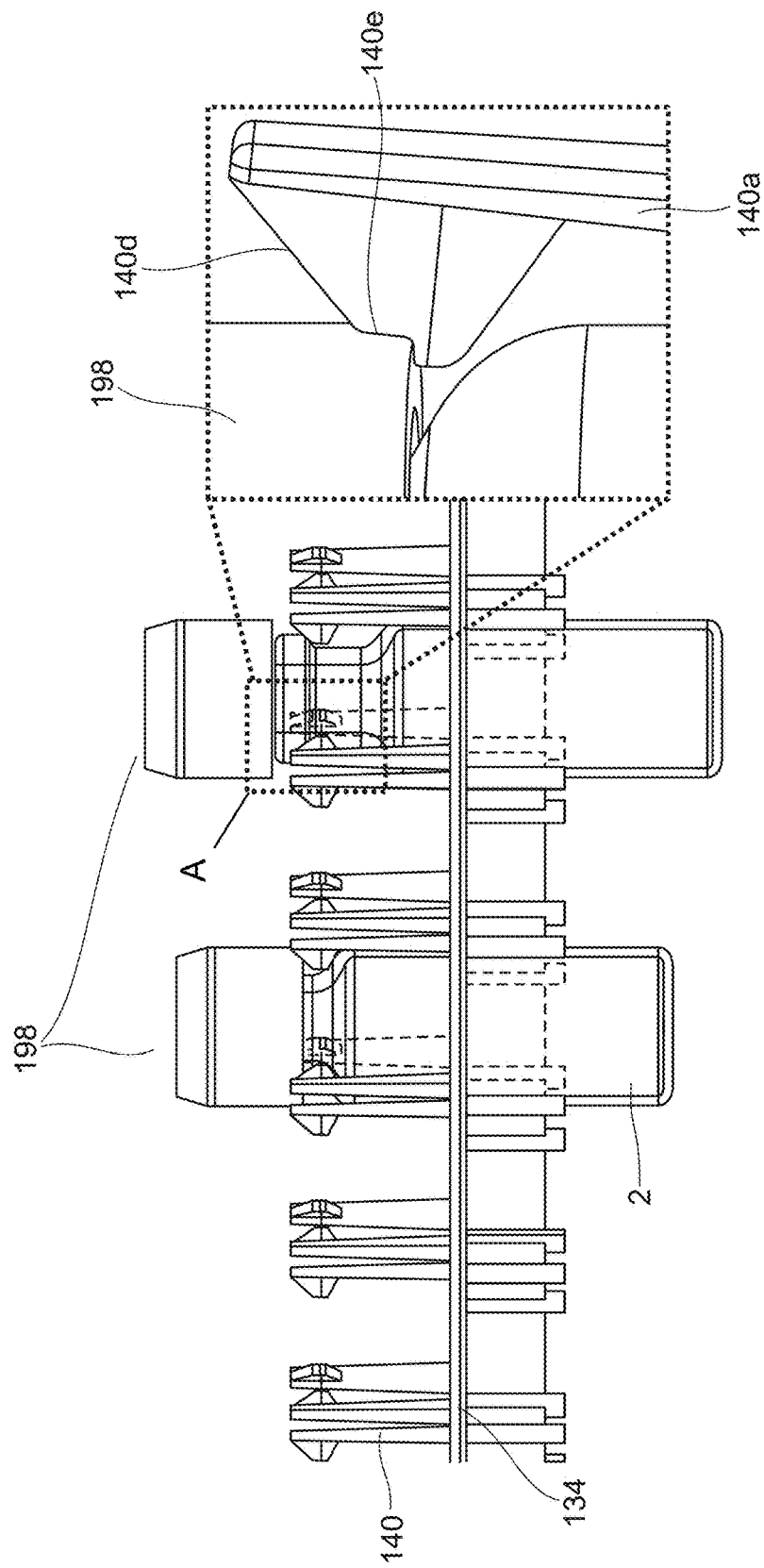

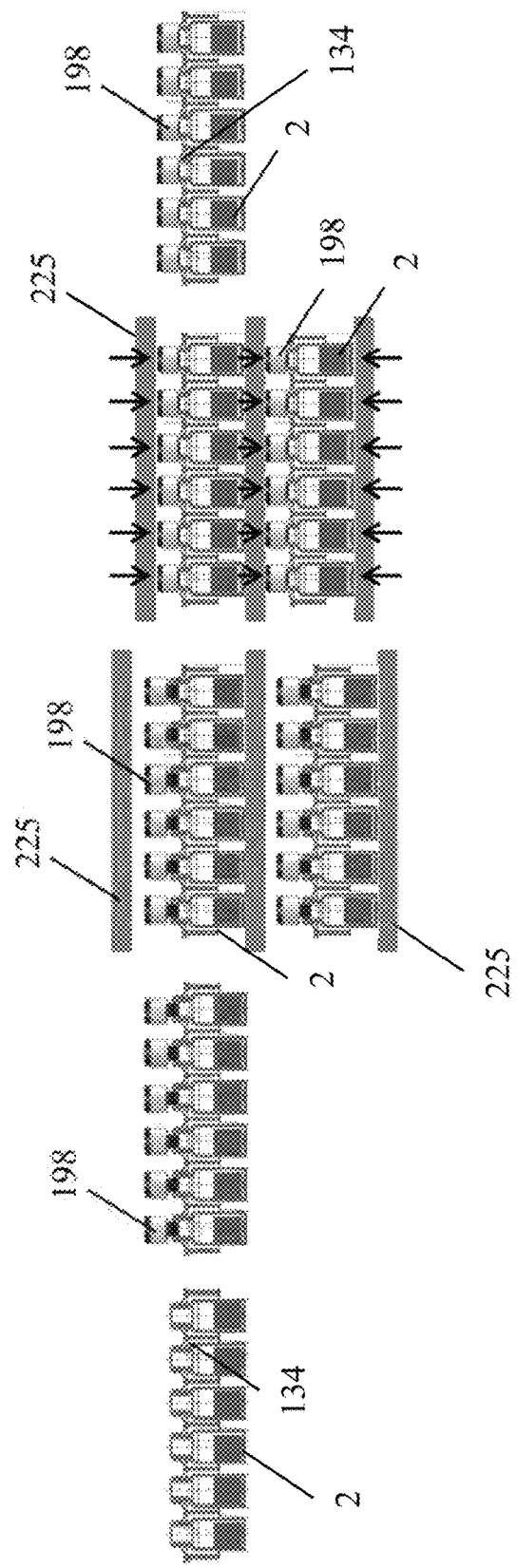

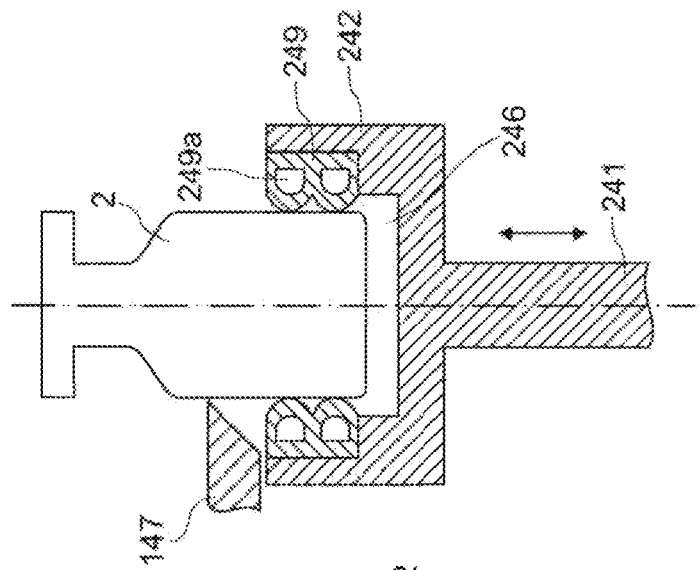
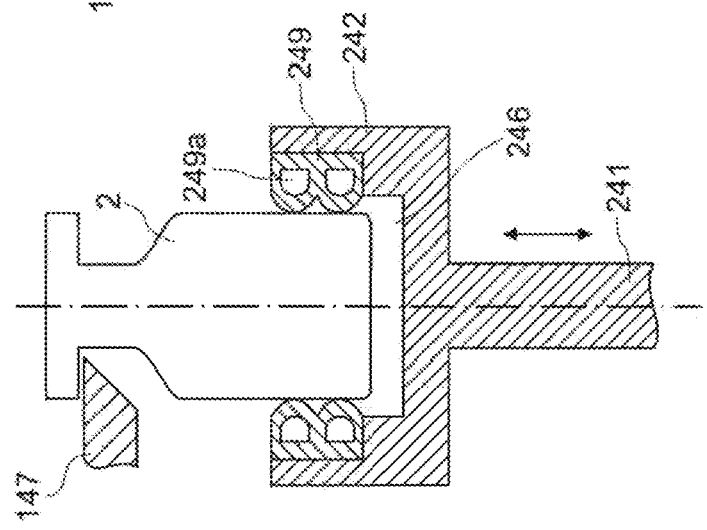
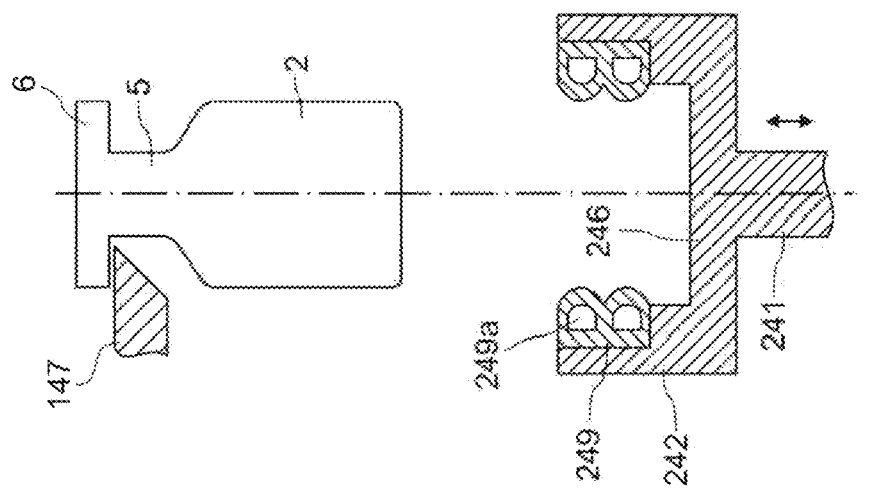

PROCESS AND APPARATUS FOR THE TREATMENT OR PROCESSING OF CONTAINERS FOR SUBSTANCES FOR MEDICAL, PHARMACEUTICAL OR COSMETIC APPLICATIONS

CROSS REFERENCE TO RELATED APPLICATIONS

This application is a continuation of U.S. application Ser. No. 14/710,394 filed May 12, 2015, which is in turn a continuation of International Application No. PCT/EP2013/003164 filed Oct. 21, 2013, which claims the benefit of German Application No. 10 2012 110 866.8 filed Nov. 12, 2012, the entire contents of all of which are incorporated herein by reference.

BACKGROUND

1. Field of Invention

The present invention relates in general to the concurrent holding of a plurality of containers for storing substances for medical, pharmaceutical or cosmetic applications, in particular of vials (vials), ampoules or cartridges, and relates in particular to a process and an apparatus for the treatment or processing of vials at or in a processing station, particularly while they are supported or at least guided by a supporting structure, and to a displacement device for this purpose.

2. Description of Related Art

Medication containers, for example vials, ampoules or cartridges, are widely used as containers for preservation and storage of medical, pharmaceutical or cosmetic preparations to be administered in liquid form, in particular in pre-dosed amounts. These generally have a cylindrical shape, can be made of plastic or glass and are available in large quantities at low costs. In order to fill the containers under sterile conditions as efficiently as possible concepts are increasingly used according to which the containers are already packaged in a transport or packaging container at the manufacturer of the containers under sterile conditions, which are then unpackaged and further processed at a pharmaceutical company under sterile conditions, in particular in a so-called sterile tunnel.

For this purpose, various transport and packaging containers are known from the prior art, in which a plurality of medication containers are concurrently arranged in a regular arrangement, for example in a matrix arrangement along rows and columns extending perpendicular thereto. This has advantages in the automated further processing of the containers since the containers can be transferred to processing stations at controlled positions and in a predetermined arrangement, for example to processing machines, robots or the like. For this purpose, holding structures are used, in which a plurality of containers can be supported concurrently in a predetermined regular arrangement. For the transfer to a processing station it is just required to properly position and open the transport and packaging container. The downstream processing station will then know at what position and in what arrangement the containers to be processed further are arranged.

Such a transport and packaging container and a corresponding packaging concept are disclosed for example in U.S. Pat. No. 8,118,167 B2. The further processing of the containers is, however, always performed such that the holding structure will be removed from the transport and packaging container, that the containers will be removed from the holding structure and isolated and then individually placed on a conveyor, in particular a conveyor belt, and transferred to the processing stations for further processing. This limits the speed of processing that can be achieved. Particularly in the isolation of the containers by means of cell wheels or the like, it always occurs that individual containers abut uncontrolled, which results in an undesired abrasion and subsequently in a contamination of the interior volume of the containers or of the processing station and in an impairment of the outer appearance of the containers which is undesirable.

U.S. Pat. No. 8,100,263 B2 discloses a portable transport and packaging container that can be packaged in a sterile manner, in which a plate-shaped holding structure can be inserted in which a plurality of medication containers are held in a regular arrangement. Firstly, the individual medication containers are placed loosely in receptacles, which are formed in the holding structure. Then, the holding structure is placed in the transport and packaging container, which is then surrounded by a gas-impermeable plastic tube. Upon subsequent evacuation of the packaging unit thus formed, the plastic tube is pressed into the spaces between the medication containers due to the negative pressure prevailing in the tube, which, on the one hand, results in a stabilization of the positions of the medication containers in the holding structure and, on the other hand, in a prevention of further uncontrolled collisions of adjacent medication containers. During the evacuation and the subsequent opening of the plastic tube, however, the medication containers may slip sideways, increasing the efforts required for automation for processing further the medication containers. In addition, the medication containers may still collide uncontrollably after opening of the plastic tube, resulting in the aforementioned disadvantages. The medication containers cannot be processed further while being in the transport or packaging container or in the holding structure, but must be isolated in the conventional manner first and handed over to downstream processing stations.

Other comparable transport and packaging containers and supporting structures are disclosed in WO 2011/135085 A1 and WO 2009/015862 A1. However, for the further processing the medication containers always need to be isolated. A further processing of the medication containers in batches while being accommodated in a holding structure as outlined above is not possible.

FIGS. 1 to 4 of WO 2009/015862 A1 disclose a holding structure, wherein resilient holding tabs press firmly against the constricted neck portions at the upper ends of the vials to retain the vials by friction. Thus, the holding structure is of very limited use for vials having high tolerances or having different outer diameters. Furthermore, the vials cannot be retained free of tension in the holding structure, which may result in an undesired bulging of the holding structure, in particular during the processing. The vials can also not be inserted from above into the receptacles of the holding structure.

In the aforementioned holding structures the outer diameter of the vials is used basically as an auxiliary contour for fixing the vials on the holding structure. Therefore, the use of such holding structures is not flexible enough for vials having larger tolerances and/or different outer diameters.

In any case, a direct contact of the bottoms of the medication containers, in particular of the bottoms of vials, is not possible for the conventional holding structures. However, this complicates the further processing of the medication containers particularly when their content is to be subjected to a freeze-drying process (also known as lyophilization or sublimation drying). Furthermore, a further processing of the medication containers directly in the holding structures is not possible, because they are either retained there rigidly or not accessible to a sufficient degree for further processing, for which reason the medication containers conventionally always need to be taken out of the holding structure for a further processing, which is time-consuming and expensive.

SUMMARY

It is an object of the present invention to provide a simple and reliable process for the treatment or processing of containers, in particular of vials, at or in a processing station, particularly using a holding structure for concurrently holding a plurality of containers. Here, the containers are to be held in a simple and reliable manner and are to be sterile packaged, unpackaged and processed cost efficiently. According to a preferred further aspect of the present invention there are to be provided a corresponding apparatus and a displacement device for this purpose.

According to the present invention these problems are solved by the process, apparatus, and vertical displacement device disclosed herein.

Thus, a process for the treatment or processing of containers is provided, which serve for storing, or contain, substances for medical, pharmaceutical or cosmetic applications, wherein the containers are conveyed automatically, by means of a conveyor, past at least one processing station or pass it for the treatment or processing. In the process, a plurality of containers, in particular vials (vials), is conveyed by the conveying device while being supported together on a carrier or supporting structure, as described by way of example hereinafter, in a regular array configuration, the containers held on the carrier are displaced to a raised position for the treatment or processing at or in the respective processing station and the containers held on the carrier are lowered after the treatment or processing, to be supported again in the regular array configuration on the carrier.

Thus, according to the invention it is possible to act on the containers exclusively from their bottom sides and/or side surfaces to ensure a desired axial displacement for the processing of the containers and their stored substances. Thus, the risk of intrusion of contamination from above into the interior of the containers can be minimized according to the invention. Since the containers can be guided and displaced more reliably while acting on their bottom sides and/or side surfaces, the process of the invention is also particularly suitable to be performed in sterile process environments, for example in a sterile tunnel or the like, where maintenance and installation work would interrupt the operation of the system and thus can be avoided as far as possible.

Because the containers are held together on the carrier in a predetermined array configuration, the effort to automate the process is lower. In particular, a plurality of containers can be handled or processed simultaneously, particularly in rows or batches. For raising the containers to the raised position, according to the invention a touching contact of a vertical displacement device with the bottom sides and/or side surfaces of the containers is sufficient to displace the containers mechanically. Lowering the containers to the initial position may be effected by suction, i.e. by means of a negative pressure, by appropriately gripping of the containers at their bottom edges, for example by clamping the containers effected temporarily mechanically or pneumatically, or by pressing down the containers.

According to a further embodiment, the vertical displacement device prevents a lateral displacement of the containers at least during raising of the containers to the raised position. This can in particular be implemented in that the vertical displacement device performs a motion only in exactly vertical direction (which can be implemented by a simple straight-line guide of the vertical displacement device) for raising the containers, but thereby retains the containers such that the containers are prevented from slipping on the vertical displacement device, e.g. by gripping or clamping of the bottom side and/or side surface of the containers.

According to a further embodiment, the vertical displacement device embraces bottom edges of the containers temporarily for raising the containers, which can be effected, for example, by a simple mechanical gripper or by a pneumatically operated sleeve.

According to a further embodiment, the bottom edges of the respective containers are embraced by a plurality of holding arms during the raising. Since these holding arms normally project laterally from the vertical displacement device, apertures or receptacles, in which the containers are held in their initial position on the carrier and through which the vertical displacement device extends during raising of the containers to the raised position, are formed in the carrier preferably correspondingly. In particular, they may have corresponding recesses, which can also serve for a further centering and guiding of the vertical displacement device during raising of the containers.

According to a further embodiment, the vertical displacement device comprises a plurality of lifting rods that are aligned along a line and can move a row of containers simultaneously to the raised position. Thus, a batch-wise or row-wise handling or processing of the containers is possible in the raised position. Here, the lifting rods may be displaced mechanically, pneumatically or hydraulically. A vertical displacement device thus configured may be disposed particularly inside the processing station, i.e. in particular in a sterile process environment.

According to a further embodiment, the process further comprises positioning the carrier or the supporting structure together with the containers held thereon relative to the vertical displacement device. For this purpose, a relative positioning of the carrier or of the supporting structure and/or of the vertical displacement device is carried out, for example by means of members that cooperate positively and are formed correspondingly.

According to a further embodiment, for lowering the containers these are retracted to the carrier by means of a negative pressure acting on a bottom portion of the containers. Thus, during the entire process it is acted on the containers exclusively from below, which minimizes the risk of intrusion of contamination into the containers as far as possible.

According to a further embodiment, the containers are laterally clamped for lowering, to be retracted to the regular arrangement on the carrier after the treatment or processing.

According to a further embodiment, the containers are pushed downwards for lowering. This can be implemented for example by means of grippers, which act on the side walls or on the constricted neck portions of the containers.

According to a further embodiment, on the carrier, which is preferably planar, particularly of rectangular shape, at least two holding tabs are provided as holding devices, which are provided at the rim of a respective aperture or receptacle and protrude from an upper side of the carrier for holding the respective container in the aperture or receptacle. Here, according to the present invention the holding tabs are configured such that these are resiliently pivoted or folded back as the containers are inserted into the apertures or receptacles and further they are matched to the containers such that these are held by the holding tabs with a radial clearance. The radial clearance allows that containers having different radial tolerances and/or outer dimensions can be retained reliably by one and the same holding structure. Conveniently, the radial clearance is designed and adapted to the outer contours and dimensions of the containers in such a manner that all holding tabs never touch the constricted neck portions at the upper ends of the containers, in particular of the vials, at the same time. At the same time the radial clearance also prevents an undesired tensioning or even bulging of the carrier when holding containers having different radial tolerances and/or outer dimensions, which provides considerable advantages, particularly in the concurrent processing of a plurality of containers while these are held by the holding structure, for example in the freeze-drying and processing at very low temperatures.

Even if the carrier should nevertheless warp or bulge during the processing, nevertheless a uniform contact to the bottoms of all containers held by the holding structure can be accomplished, particularly when these are additionally held by the holding tabs on the holding structure with a sufficient axial clearance, because the axial clearance also allows for a compensation of length tolerances.

The holding tabs are formed or supported resiliently to a sufficient degree so that the containers can be inserted axially, i.e. in the direction of the longitudinal axis of the containers and perpendicular to the plane of the carrier, into the apertures or receptacles from the upper side or from the lower side of the carrier, in particular with resilient deformation of the holding tabs, for example by bending them back. Thus, the loading of the carrier with containers can be automated easily, which is further favored by a regular arrangement of the apertures or receptacles, preferably in a two-dimensional matrix.

The underside of an expanded upper rim portion of the containers has proven to be a preferred location at which the containers are held or supported on the holding tabs, which is typically provided at vials particularly as the so-called rolled edge or as a shoulder. In this region a supporting or bearing surface for holding or supporting the containers is available with a sufficient extension in the radial direction of the apertures or receptacles in order to easily implement the above-mentioned radial clearance for the holding of the containers.

Because the containers can be raised or moved, for example, rotated, in the apertures or receptacles with very little expenditure of force, they can be processed further easily while they are disposed in the holding structure and held or at least guided by it. This type of support has turned out to be of advantage e.g. for closing the containers by means of crimping a metal lid. The process steps required for this purpose can be performed on the metal lid while the container is held in or at least guided by the aperture or receptacle of the holding structure. This type of support has turned out to be of advantage also in the processing of containers while they are held or accommodated in the holding structure. For example, the holding structures together with the containers accommodated or held by them may be inserted into a freeze-dryer. Because of the holding of the containers in the holding structures with a certain clearance it can be ensured that the bottoms of all containers evenly rest on a cooling base, such as a cooling finger of the freeze-dryer. Or the containers may be raised without too much effort in the apertures or receptacles of the holding structure and handled for the processing.

According to a further embodiment, the containers are completely raised out of the apertures or receptacles, which are provided in the carrier and define the array in order to be treated or processed at or in the processing station. The containers are thus completely released from the holding devices of the holding structure which causes a different positioning of the containers, to prevent a lateral slipping of the containers during the treatment or processing of the containers. This positioning can be implemented particularly by a suitable arrangement of the vertical displacement device, for example by embracing the bottom edges of the containers by portions of the vertical displacement device.

According to a preferred embodiment, the holding tabs are formed as resilient holding tabs, but have a sufficient resiliency to be pivoted back or folded back resiliently to a sufficient extent as the containers are inserted into the apertures or receptacles to make clear the way for the containers into the apertures or receptacles. This can be accomplished easily by a proper dimensioning, selection of the materials and design of the material thickness of the holding tabs. The holding tabs are thus preferably formed from a plastic material.

According to an embodiment, the holding tabs are preloaded resiliently towards a holding position, preferably by means of a resilient return member, for example a return spring or a plastic plate or a resilient plastic structure, which cooperates suitably with the associated holding tab and is disposed or formed on the upper side of the carrier.

According to an embodiment, the holding tabs are matched to the containers such that the containers rest loosely on upper sides of the holding tabs with an expanded rim, which is formed at an upper end of the containers, particularly with the above-mentioned rolled edge. Thus, the containers can be removed from the apertures or receptacles upward without resistance.

According to an embodiment, the holding tabs embrace the expanded rim in such a manner that the containers are held by the holding tabs with a radial clearance or with radial and axial clearance. In this way, the containers may be securely retained in axial direction in the apertures or receptacles. For removing the containers from the apertures or receptacles the tabs only need to be pivoted back or folded back again in the same way as for inserting the containers.

According to an embodiment, the holding tabs are disposed and distributed on the upper side of the carrier such that these do not contact each other directly as they are pivoted or folded back and that they do not obstruct a directly adjacent aperture or receptacle. Thus, the packing density of the containers at the carrier can be increased further. In particular, the holding tabs are configured such that directly adjacent holding tabs do not contact each other when they are pivoted or folded back towards the carrier upon insertion of the containers into the associated apertures or receptacles.

According to an embodiment, slanted insertion surfaces are formed at upper ends of the holding tabs each of which passing into a holding nose protruding radially inwards for holding the containers. The containers can thus be inserted into the apertures or receptacles more easily and with less expenditure of force. Upon insertion of the containers from above into the apertures or receptacles initially the bottoms or bottom ends of the containers get in contact with the slanted insertion surfaces. Upon further insertion of the containers, the bottom ends or bottoms of the containers slide downward along the slanted insertion surfaces and spread the holding tabs apart or fold or pivot them back. Upon further insertion of the containers finally the cylindrical side wall gets in contact with the holding noses and slides there along, until eventually the bottom side of the aforementioned rolled edge rests loosely on the holding noses of the holding tabs.

According to an embodiment, the holding tabs or their slanted insertion surfaces associated with a respective aperture or receptacle are twisted in the same direction and by an angle of less than 90°, so that the holding tabs are pivoted or folded back radially and with a movement component in the circumferential direction upon insertion of the containers from the upper side of the carrier into the apertures or receptacles, if viewed in a plan view. Depending on the configuration and distribution of the holding tabs, this may allow that directly adjacent holding tabs do not touch each other, when they are pivoted or folded towards the carrier upon insertion of the containers into the associated apertures or receptacles.

According to a further embodiment, the apertures or receptacles on a lower side of the carrier opposite to the upper side are limited at least in sections by a respective side wall in order to prevent a contact of containers in directly adjacent apertures or receptacles, wherein the side walls are preferably formed such that the containers are freely accessible from the lower side of the carrier. The side walls of adjacent apertures or receptacles are preferably connected to each other, which contributes to a further advantageous stiffening of the carrier. The side walls are preferably formed integrally with the carrier, which can be implemented easily for example by means of plastic injection molding technology.

The bottoms or bottom ends of the containers accommodated in the apertures or receptacles preferably protrude from the lower ends of the side walls, so that the bottoms of the containers are freely accessible from the lower side of the carrier. This allows a processing of the containers, while they are held on the carrier in the apertures or receptacles, as discussed below.

According to a further embodiment the holding tabs are integrally formed with the carrier which allows a cost effective production, for example by injection molding from a plastic material. The resilient holding tabs protrude arcuately from the upper side of the carrier and preferably protrude a little into the associated aperture or receptacle, if viewed in a plan view. Thus, the containers may be held in particular in the region of a constricted neck portion and near the upper open end of a container or vial, as explained in more detail below. The arcuate configuration of the holding tabs facilitates inserting the containers into the apertures or receptacles of the carrier or their removal again.

According to a further embodiment, the holding tabs associated with an aperture or receptacle are disposed and formed symmetrically about a respective center line of the aperture or receptacle. The containers are thus automatically held centered in the respective apertures or receptacles of the carrier. The symmetry also prevents an accidental tilting or twisting of the containers when inserted into or held in the apertures or receptacles of the carrier.

According to a further embodiment, the resilient holding tabs each form a three-point bearing for holding the container in the respective aperture or receptacle of the carrier, whereby an automatic centering of the containers in the associated apertures or receptacles and a very precise and stable definition of the positions of the containers on the carrier is favored even more.

According to a further embodiment, the side walls are disposed distributed in a regular hexagonal arrangement on the lower side and/or upper side of the carrier. Overall, a honeycomb structure is formed in this way, which can contribute advantageously to a further stiffening of the carrier. Here, the side walls of adjacent apertures or receptacles are preferably connected with each other.

According to a further embodiment, the side walls of a respective aperture or receptacle are each formed circumferential and form a hexagonal honeycomb structure on the lower side of the carrier. The side walls of directly adjacent apertures or receptacles merge in the corner regions of the apertures or receptacles and are connected with each other or formed integrally, resulting in a further stiffening of the carrier.

According to a preferred further embodiment, respective three holding tabs protrude from a connecting region of the side walls in a configuration with a threefold-symmetry into the respectively associated apertures or receptacles, so that advantageously a cancellation of forces can be accomplished in the connecting region. Thus, the carrier can hold the plurality of containers with low stress.

According to a further embodiment, the side walls of a respective aperture or receptacle are each formed circular and circumferential. Preferably, the side walls of directly adjacent apertures or receptacles are connected with each other or formed integrally, which also results in a further stiffening of the carrier.

According to a further embodiment, the apertures or receptacles are arranged in a regular arrangement of rows and columns distributed on the carrier, wherein the rows and columns are each offset to one another and form a periodic array. This array is advantageous for an automated treatment of the containers.

According to a further embodiment, the base area of the holding structure can be reduced by removing or folding back the members that can be removed or pivoted back and that are formed along the edges. This allows a higher packing density during the processing of the containers that are accommodated in the holding structures, for example in a sterile tunnel or in a freeze-dryer.

According to a further embodiment, a high packing density and at the same time a mutual stabilization of the positions of the carriers can be implemented as a result of the positive engagement of recesses and/or protrusions, which are formed either on the aforementioned members of the carrier that can be removed or pivoted back or directly in the edge of the carrier, with protrusions and/or recesses of a corresponding shape of a directly adjacent carrier.

According to a further aspect of the present invention directly adjacent holding structures can be coupled directly with each other so that these are immovable relative to each other in the longitudinal direction and/or in the transverse direction. In other words: the directly adjacent holding structures can be handled together, as a kind of unit consisting of several (of at least two) holding structures, without the need for significantly changing their position relative to each other. According to the invention a releasable, temporary coupling of the directly adjacent holding structures is chosen for this purpose, wherein in principle any form-fitting or frictional coupling technique can be used, as long as the coupling force that can be achieved by the coupling is larger than the forces typically encountered during handling or processing of the holding structures, which seek again to separate the directly adjacent holding structures from each other.

A further aspect of the present invention relates to a process for the treatment or processing of containers that serve for storing, or contain, substances for medical, pharmaceutical or cosmetic applications, wherein the containers can be weighed in an even simpler and more economical manner. Herein, a plurality of containers is conveyed by the conveyor while being held all together in a regular arrangement by a carrier, as described herein, and the containers held on the carrier are raised to a raised position for the treatment or processing at or in the respective processing station. According to the invention, the containers are weighed by a weighing device between two process steps, in particular while these are held on a carrier or at least guided in the apertures, receptacles or holding devices, as described below.

For this purpose the weighing device is preferably integrated into a vertical displacement device used for raising and lowering of the containers, as described below.

A further aspect of the present invention relates to an apparatus which is configured for carrying out a process, as described herein, for the treatment or processing of containers that serve for storing, or contain, substances for medical, pharmaceutical or cosmetic applications.

A further aspect of the present invention relates to a vertical displacement device for such an apparatus, as described below.

BRIEF DESCRIPTION OF THE DRAWINGS

The invention will now be described by way of example and with reference to the accompanying drawings, from which further features, advantages and problems to be solved will be-come apparent. In the drawings:

FIG. 1a shows a holding structure according to a first embodiment for use of a process according to the present invention in a perspective plan view;

FIG. 1b shows the holding structure of FIG. 1a in a plan view;

FIG. 1g shows a holding structure according to a further variant of FIG. 1a in a perspective plan view;

FIG. 1h shows the coupling of two directly adjacent holding structures of FIG. 1a in a schematic plan view;

FIG. 2b shows the transport or packaging container of FIG. 2a in a partial cross-section and in a plan view;

FIG. 2g is a further partial cross-section of the holding structure of FIG. 2a without containers;

FIG. 2h shows the holding of a container in a holding structure according to a further embodiment of the present invention in a greatly enlarged partial cross-section;

FIG. 2i shows a slanted insertion surface of a holding tab according to a variant of the holding structure of FIG. 2a in a greatly enlarged plan view;

FIG. 2j shows a further variant of the holding tabs for a holding structure of FIG. 2a;

FIG. 2l shows a further variant of a holding structure for use in a process according to the present invention;

FIG. 2m shows a further variant of a holding structure for use in a process according to the present invention;

FIG. 2n shows a first step of a motion sequence of the insertion of a container into a holding structure according to another variant;

FIG. 2o shows a second step of the motion sequence of FIG. 2n;

FIG. 2p shows a third step of the motion sequence of FIG. 2n;

FIG. 3c shows the holding structure of FIG. 3a in sectional view;

FIG. 3d shows a partial cross-section of the holding structure of FIG. 3a;

FIG. 3e shows the latching and engagement of protrusions and recesses on the edges of two holding structures of FIG. 3a in a greatly enlarged partial plan view;

FIG. 3f shows a partial cross-section along A-A of FIG. 3e;

FIG. 4b shows in schematic side view or partial section, a first step in a sequence of the process steps in a process according to the present invention in the processing station according to FIG. 4a, wherein the containers are in a starting position;

FIG. 4c shows a second step in the sequence of the process steps of FIG. 4b;

FIG. 4d shows a third step in the sequence of the process steps of FIG. 4b;

FIG. 4e shows a detail view of circle A in FIG. 4d;

FIG. 5b shows a perspective view of the first step in the sequence of the process steps of FIG. 5a;

FIG. 5c shows a side view of a second step in the sequence of the process steps of FIG. 5a;

FIG. 5d shows a side view of a third step in the sequence of the process steps of FIG. 5a;

FIG. 5e shows a side view of a fourth step in the sequence of the process steps of FIG. 5a;

FIG. 7b shows various a sectional view of the push rod of FIG. 7a;

FIG. 7d shows a sucker of the push rod of FIG. 7a;

FIG. 8b shows a plan view of the apertured plate with a guidance structure of FIG. 8a;

FIG. 9a is a schematic flow diagram of a process for processing or treatment of vials by means of a processing station according to FIG. 4a;

FIG. 9c is another example of the use of such a process for flanging or crimping a metal cap on an upper edge of vials;

FIG. 9d is a schematic flow diagram of a further process for the processing or treatment of vials by means of a processing station according to FIG. 4a;

FIG. 9e shows a further example for the use of such a process for the sealing of vials by means of sterile sealing caps, which are pushed directly onto the upper rims of the vials;

FIG. 9f shows a magnified view of circle A of FIG. 9e;

FIG. 9g shows a first step of another further example for the use of such a process for the sealing of vials by means of sterile sealing caps, which are pushed directly onto the upper rims of the vials;

FIG. 9h shows a second step of the example in FIG. 9fg

FIG. 9i shows a third step of the example in FIG. 9g;

FIG. 9j shows a fourth step of the example in FIG. 9g;

FIG. 9k shows a fifth step of the example in FIG. 9g;

FIG. 13a shows, a first step in a sequence, the use of a further vertical displacement device according to the present invention for displacing containers, which are held in a holding structure of the aforementioned type;

FIG. 13b shows a second step in the sequence of FIG. 13a; and

FIG. 13c shows a third step in the sequence of FIG. 13a.

In the drawings, identical reference numerals designate identical or substantially equivalent elements or groups of elements.

DETAILED DESCRIPTION

According to the present invention, a supporting structure as well as a transport and packaging container accommodating such a holding structure are used, as described below, for concurrently holding a plurality of containers for storage of substances for cosmetic, medical or pharmaceutical applications, preferably in an array configuration, in particular in a matrix configuration with regular intervals between the containers along two different directions in space, preferably along two mutually orthogonal spatial directions or in regular rows, which are offset to each other. Subsequently, at first the holding structure is described before the process and apparatus according to the present invention are described.

Figure 1C:
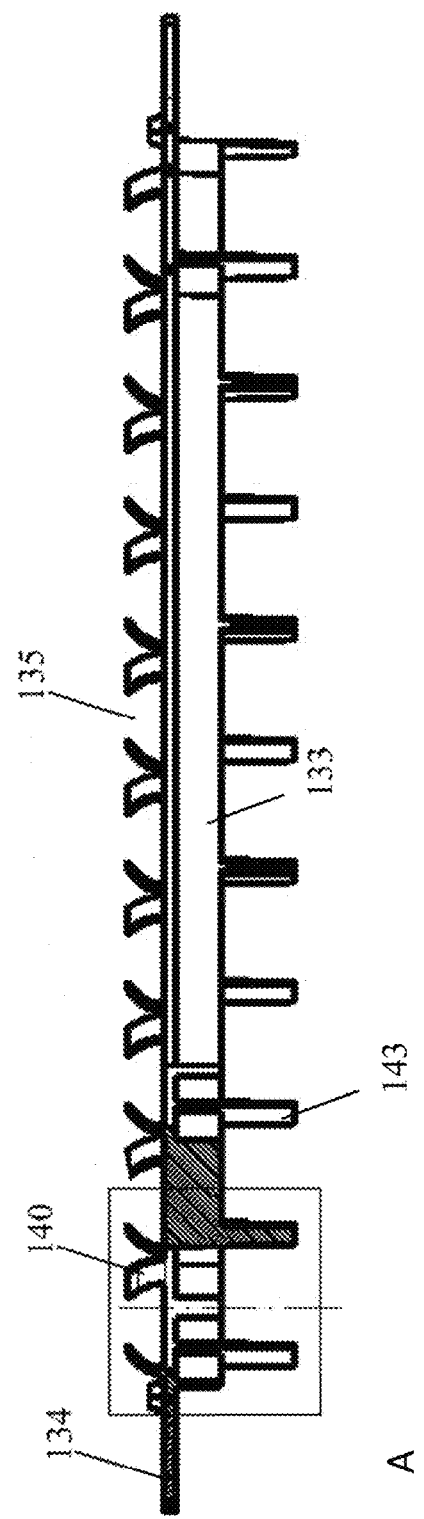
FIG. 1c is a partial cross-section along A-A of FIG. 1b.
Figure 1D:
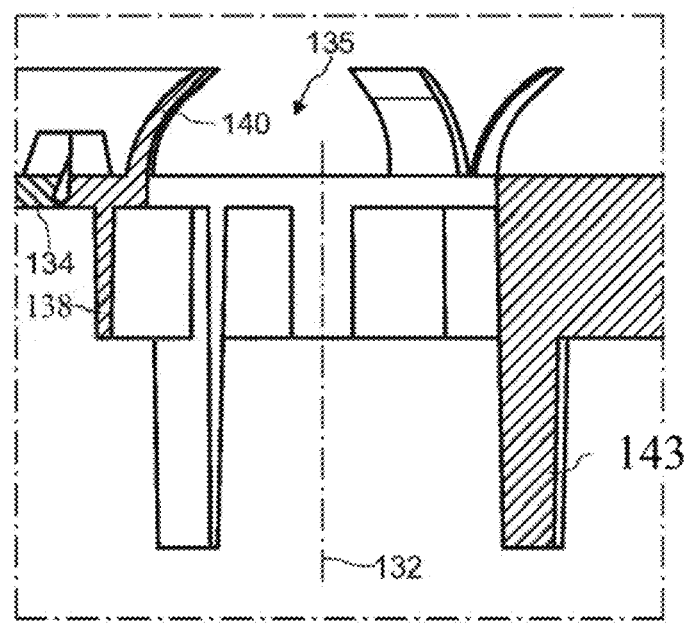
FIG. 1d shows a greatly enlarged partial cross-section in the insert A shown in FIG. 1c.
Figure 1E:
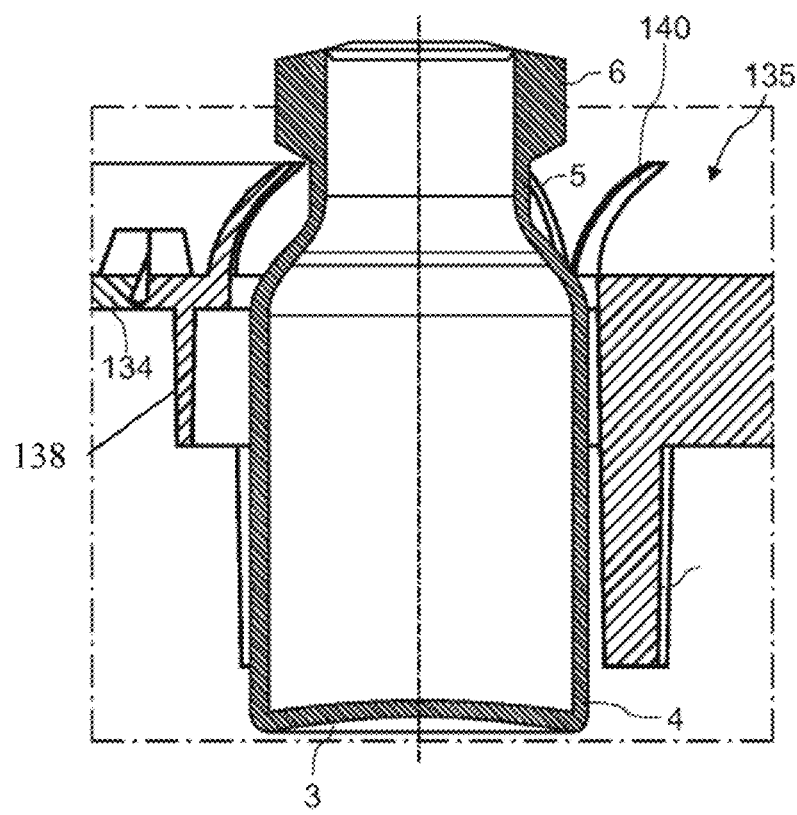
FIG. 1e shows the holding of a container in the apertures of a holding structure according to the first embodiment in the greatly enlarged partial cross-section of FIG. 1d.

An example of such medication containers embodied as vials is schematically shown in FIG. 1e in a longitudinal sectional view. These have a cylindrical basic shape, having a cylindrical side wall with—within tolerances—constant inner and outer diameters, which project vertically from a flat vial bottom 3, which merges in a constricted neck portion 5 of a relatively short axial length near the upper open end of the vial and then merges in an expanded upper rim 6 (so-called rolled edge), which has a larger outer diameter than the associated neck portion 5 and is configured for connection to a sealing member. As can be concluded from FIG. 1e, the underside of the rolled edge 6 is slanted and extends downward under an acute angle and towards the constricted neck portion 5. As shown in FIG. 1e, a gap in radial direction is formed between e.g. the left holding tab 140 (or a plurality of holding tabs or all holding tabs of an aperture or receptacle) and the constricted neck portion 5 of the container.

The neck portion 5 can be formed with smooth walls and without an external thread or may be provided with an external thread for screwing on a sealing member. For example, a stopper (not shown) may be inserted into the inner bore of the neck portion 5 and the upper rim 6, whose upper end is connected with the upper rim 6 of the vial in a gas-tight manner and protected against the intrusion of contaminants into the vial, for example by crimping a metal protective foil, which is not shown. Such vials are radially symmetric and are made of a transparent or colored glass or of a suitable plastic material by blow molding or plastic injection molding techniques, and in general can be internally coated so that the material of the vial emits minimal impurities to the agent to be received.

Another example of a medication container according to the present application are ampoules, cartridges, syringes or injection containers. Ampoules or cartridges are containers for medication agents for usually parenteral administration (injection), for cosmetics and other agents and are usually cylindrical in shape with an extended tip (spear or head) and a flat bottom or also with two extended tips at both ends. These may be formed in particular as snap-off ampoules with an annular predetermined breaking point around the ampoule neck or as an OPC cartridge (One-Point-cut ampoule) having a breaking ring inscribed into the glass. Syringes or injection containers, also known as injection flasks, vials or reusable ampoules, are cylindrical containers of glass or plastic shaped similar to a vial, usually having a relatively small nominal volume (e.g. 1 ml, 10 ml). They are sealed with a rubber plug with septum (puncture rubber). For protecting the septum and fixing the rubber plug an outer closure (beaded cap or crimp), often made from an aluminum sheet, is necessary. In a cartridge the liquid is stored in a cylinder, which is closed at one end by means of a thick rubber or plastic plug. This acts as a piston when the content is pressed out using a cartridge syringe. At the other end the cylinder is closed only by means of a thin diaphragm, which is pierced from the rear end of the cartridge syringe (a cannula sharpened on both sides) in the application. Cylindrical ampoules are often used in dentistry for local anesthesia. Special cylindrical ampoules with a specially shaped front part (e.g. thread) are used for insulin therapy in insulin pens.

In the sense of the present invention, such containers are used for storage of substances or agents for cosmetic, medical or pharmaceutical applications, which are to be stored in one or several components in solid or liquid form in the container. Especially in the case of glass containers storage periods can amount many years, notably depending on the hydrolytic resistance of the glass type used. While, in the following, cylindrical containers are disclosed, it should be noted that the containers, in the sense of the present invention, may also have a different profile, for example a square, rectangular or polygonal profile.

Inevitably such containers have tolerances due to the production which can be of the order of one or several tenths of a millimeter in particular for glass containers. To compensate for such manufacturing tolerances, while ensuring that all bottoms 3 of the vials can be disposed in a plane, according to the present invention the containers are fixed on a holding structure. Here, this holding of the containers is implemented in the transition region between the constricted neck portion 5 and the expanded upper rim 6. In particular, the underside of the rim 6 of the container is supported on the upper ends of holding tabs 140 in the transition region towards the constricted neck portion 5, as described below in more detail. The holding tabs 140 are preferably formed from a sufficiently flexible or resilient plastic. As an alternative, however, the holding tabs may also be designed to be relatively stiff but supported movably on the upper side of the carrier 134 so that they are pivoted or flapped back resiliently out of the aperture 135 as the containers are inserted, as described below. For this purpose, the holding tabs may be preloaded resiliently towards the holding position shown in FIG. 1e by means of resilient return members (not shown), such as return springs or resilient plastic structures or resilient plastic plates.

For concurrently holding a plurality of containers, according to a first embodiment, as shown in FIGS. 1a and 1b, a planar rectangular carrier 134 is provided that is formed of a plastic material, for example by punching or injection molding, and comprises a plurality of apertures 135 for accommodating the glass vials 2. The apertures 135 are arranged in a regular two-dimensional array, in the illustrated embodiment in a matrix array of rows and columns extending perpendicularly, which are arranged at equidistant intervals and regularly offset to each other in a periodic arrangement.

The apertures 135 are delimited by side walls 138 (see FIG. 1d) on the lower side of the carrier 134 to prevent a collision of the containers, which are accommodated in directly adjacent apertures 135. According to FIG. 1b, resilient holding tabs 140 protrude arcuately from the upper side of the carrier 134, if viewed in a plan view, into the associated apertures 135. The resilient holding tabs 140 and the side walls 138 are preferably formed integrally with the planar carrier 134, e.g. by means of a one-component or two-component plastic injection molding process.

According to FIG. 1b, the side walls 138 each merge in the corner regions of the apertures 135 and are there connected with each other or formed integrally. The resilient holding tabs 140 protrude into the adjacent apertures 135 in these corner regions in a configuration with a threefold point symmetry. This results in a symmetrical force distribution when holding the containers by means of the holding tabs 140. The holding tabs 140 thus result in an advantageous three-point bearing of the containers in the apertures, so that the containers are supported in a respective aperture 135 automatically centered with respect to a center line 132 (see FIG. 1d).

FIG. 1c shows a partial sectional view of the holding structure along A-A of FIG. 1b. It can be seen that the carrier 134 is delimited on the lower side by a circumferential rim 133 on which the carrier 134 can be supported on a circumferential step 13 (see FIG. 2a) of a transport or packaging container 1.

FIG. 1d shows a greatly enlarged partial sectional view of the insert shown in FIG. 1c. It can be seen that the containers can be inserted easily from below into the apertures 135 of the carrier 134. Upon insertion of the containers into the apertures 135 there is a resilient bending of the resilient holding tabs 140.

Depending on the specific configuration of the containers to be supported these can in principle also be inserted from above into the apertures 135 of the carrier 134 so that they are held on the carrier 134. This has the advantage of further reducing the risk that a liquid or other content of the containers from the inner volumes of the containers yet open can arrive uncontrollably on the holding structure, in particular on the carrier plate 134, during their insertion into the apertures and during the pivoting back of the holding tabs 140. For this purpose slanted insertion surfaces may be provided on the upper sides of the resilient holding tabs 140, such as those described in more detail below with reference to FIG. 2g for an alternative embodiment.

By means of the strength, material and design of the resilient holding tabs 140 the force required for inserting and removing a container can be specified easily.

According to a preferred embodiment, the containers are supported loosely on the holding tabs at least with a radial clearance and preferably both with radial and axial clearance. In this way, even large tolerances of containers and different outer diameters can be easily compensated for in the region of the neck portion 5. Namely, for supporting the containers it is sufficient if the rolled edge 6 still rests on the upper sides of the holding tabs 140. Basically thereby also containers of various types, e.g. with different diameters in the region of the neck portion 5, can be held by one and the same holding structure.

FIG. 1e illustrates this in the same greatly enlarged partial sectional view as shown in FIG. 1d and illustrates the holding of a container in an aperture 135 of the carrier 134. According to FIG. 1e the bottom of the expanded rim 6 rests loosely on the front ends of the resilient holding tabs 140 in the transition region between the constricted neck portion 5 and the rim 6 for fixing the position of the container. As can be seen in FIG. 1e, a gap exists between the holding tabs 140 (see left-hand side of the drawing) and the constricted neck portion 5, which enables a radial clearance. Due to this support with radial clearance, depending on the specific design of the container, the possibility exists to displace the container supported by the holding tabs 140 in axial direction, i.e. in the longitudinal direction of the container, for example until the bottoms 3 of all containers supported by the carrier 134 are held at the same distance to the carrier 134 to jointly span a plane.

According to FIG. 1e the container is inserted into the aperture 135 until the expanded rim 6 is supported on the front ends of the holding tabs exactly at the transition region between the constricted neck portion 5 and the expanded upper rim 6. This can be accomplished, for example, by inserting the containers from below into the apertures 135 of the carrier 134 and by subsequent pushing-down of the containers, namely until the front ends of the holding tabs abut exactly at the transition region between the constricted neck portion 5 and the expanded upper rim 6. In the holding position shown in FIG. 1e, a certain radial distance between the step-like transition region between the upper rim 6 and the constricted neck portion 5 and the front ends of the holding tabs 140 is provided in any case for the great majority of the fixed containers. In this way, manufacturing tolerances of the containers in the axial direction and also manufacturing tolerances in the radial direction can be compensated for, and thus also containers with different diameters can be supported in the region of the constricted neck portion 5 by one and the same carrier 134. In this way also potential tension in the plastic of the carrier 134 caused by the accommodation of containers with a too large outer diameter can be kept small.

According to alternative embodiments, as described below, the containers may also be supported on the carrier 134 in a positive-fit manner or by friction.

Figure 2A:
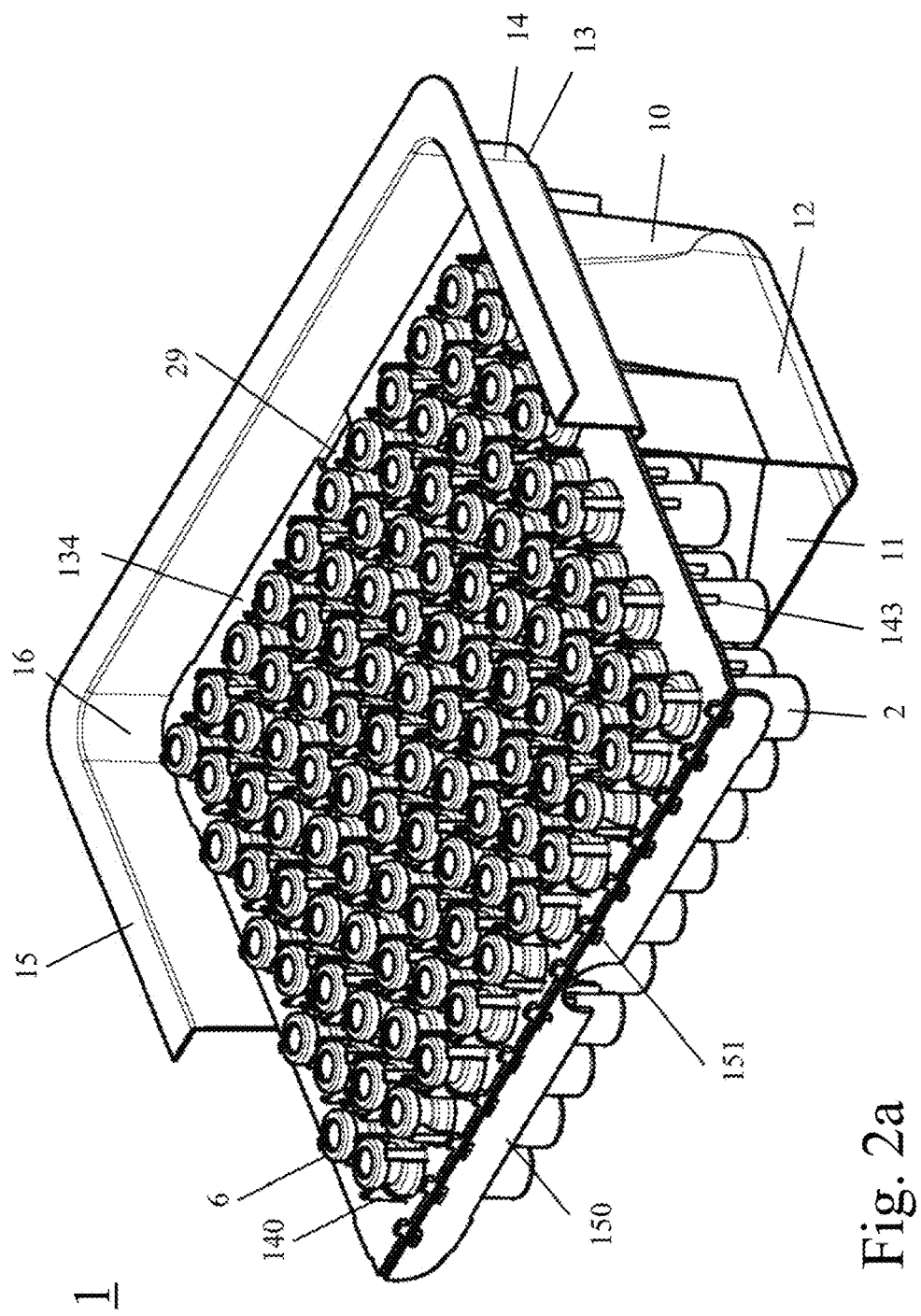
FIG. 2a shows a transport or packaging container with a holding structure according to a second embodiment for use in a process according to the present invention accommodated therein and with containers accommodated by it.

For the transport and packaging of the holding structure described above together with the containers accommodated therein, a transport and packaging container 10 is used, such as this is schematically shown in FIG. 2a for a holding structure or carrier 134 according to a second embodiment of the present invention. According to FIG. 2a the transport and packaging container 10 is substantially box-shaped or trough-shaped and comprises a bottom 11, a circumferential side wall 12 extending perpendicularly, a step 13 projecting substantially perpendicularly, a circumferential upper side wall 14 and an upper edge 15 on which a flange is formed. Conveniently, the corners 16 of the transport and packaging container 10 are rounded. The upper side wall 14 may be formed inclined at a slight angle of inclination relative to a line perpendicular to the bottom 11 in order to facilitate the insertion of the holding structure 134. Such a transport and packaging container 10 is preferably formed of a plastic material, in particular using plastic injection molding technology, and is preferably formed of a clear transparent plastic material to enable an optical inspection of the holding structure 134 accommodated in the transport and packaging container 10 and of the containers 2 supported by it.

For accommodating the holding structure 134 in the transport and packaging container 10, it may be surrounded by a circumferential peripheral web 133, as shown in FIG. 1c. Such a peripheral web may also be formed in sections continuously along the peripheral edge. For a reliable positioning of the holding structure 134 in the transport and packaging container 10, the holding structure 134 and the transport and packaging container 10 comprise positioning structures that are cooperating with each other, in particular in a positive-fit manner. Thus, positioning structures in the form of protrusions or recesses (or cavities) may be formed at an appropriate location, particularly on the step 13 or on supporting surfaces 18 (see FIG. 2b) of the transport and packaging container 10, which cooperate in a positive-fit manner with correspondingly configured recesses (or cavities) or protrusions of the holding structure for precisely positioning the holding structure 134 in the transport and packaging container 10. For this purpose a plurality of pin-like protrusions may be formed particularly on the step 13 of the transport and packaging container 10, which cooperate with corresponding centering apertures formed in a supporting surface of the holding structure 134. According to FIG. 2a, the step 13 of the transport and packaging container 10 is formed as a circumferential, planar supporting surface on which the holding structure 134 is directly supported. According to further embodiments, also supporting surfaces 18 or supporting members may be formed on the side walls 12 of the transport and packaging container 10, in particular in the form of protrusions. In this way, the holding structure 134 can be positioned precisely in the transport and packaging container 10 and in this way the plurality of vials 2 can be disposed and supported in a regular array and at precisely defined positions in a transport and packaging container 10 with standardized dimensions. Particularly, in this way it can be accomplished that all bottoms or bottom ends of the vials 2 are disposed in a plane jointly spanned and in parallel with the bottom 11 or upper edge 15 of the transport and packaging container 10.

Although, in FIG. 2a, the bottom 11 of the transport and packaging container 10 is shown to be closed and formed integral with the side wall 12, the lower end of the transport and packaging container 10 may also be open in the manner of the upper end, in particular provided with a flange-like bottom edge in the manner of the upper edge 15 so that the bottoms of the vials 2 are freely accessibly from the lower side of the transport and packaging container 10, e.g. for processing steps in a sterile tunnel or in a freeze-dryer, as explained hereinafter in more detail.

As explained below in more detail, according to the present invention the containers may also be processed all together inside the holding structure 134 or inside the transport and packaging container 10, in particular in a sterile tunnel or freeze-dryer.

For facilitating the insertion of the holding structure 134 into the transport and packaging container 10 and its removal therefrom, access apertures 29 are formed on two longitudinal sides of the holding structure 134, which are used by gripping arms or the like to grip the holding structure 134. As viewed in longitudinal or transverse direction of the holding structure 134, the access apertures 29 may be offset to one another, which further simplifies an unambiguous positioning of the holding structure 134 in the transport and packaging container 10.

Figure 2C:
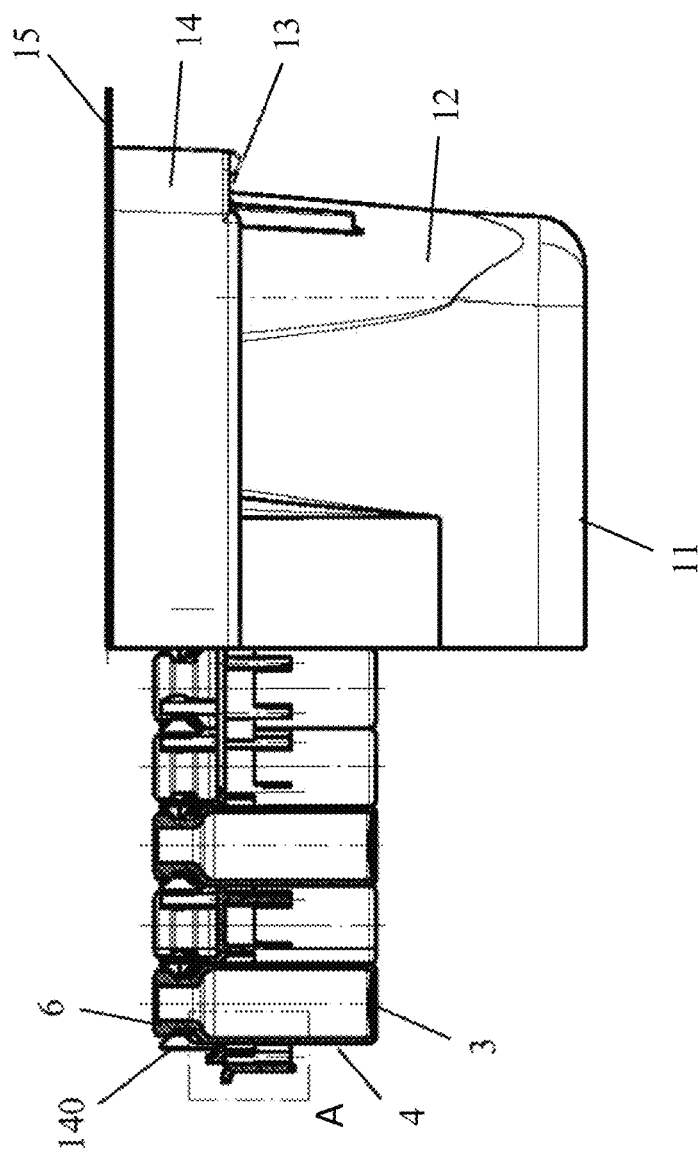
FIG. 2c shows the holding of containers in the holding structure according to the second embodiment.
Figure 2D:
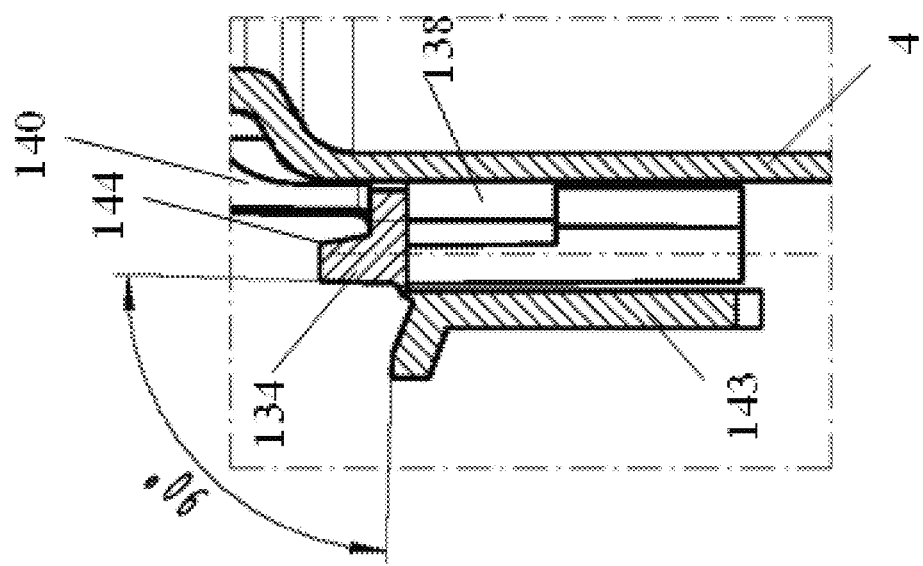
FIG. 2d shows a greatly enlarged partial cross-sectional view in the insert A shown in FIG. 2c.

FIG. 2c shows the holding of containers in the holding structure according to the second embodiment in a partial sectional view along A-A of FIG. 2b and FIG. 2d shows an enlarged partial sectional view from section A of FIG. 2c. Particularly, it can be seen that slanted stop noses 144 are provided on the upper side of the carrier, which limit the pivoting back of the resilient holding tabs 140 upon insertion of the containers.

Figure 2E:
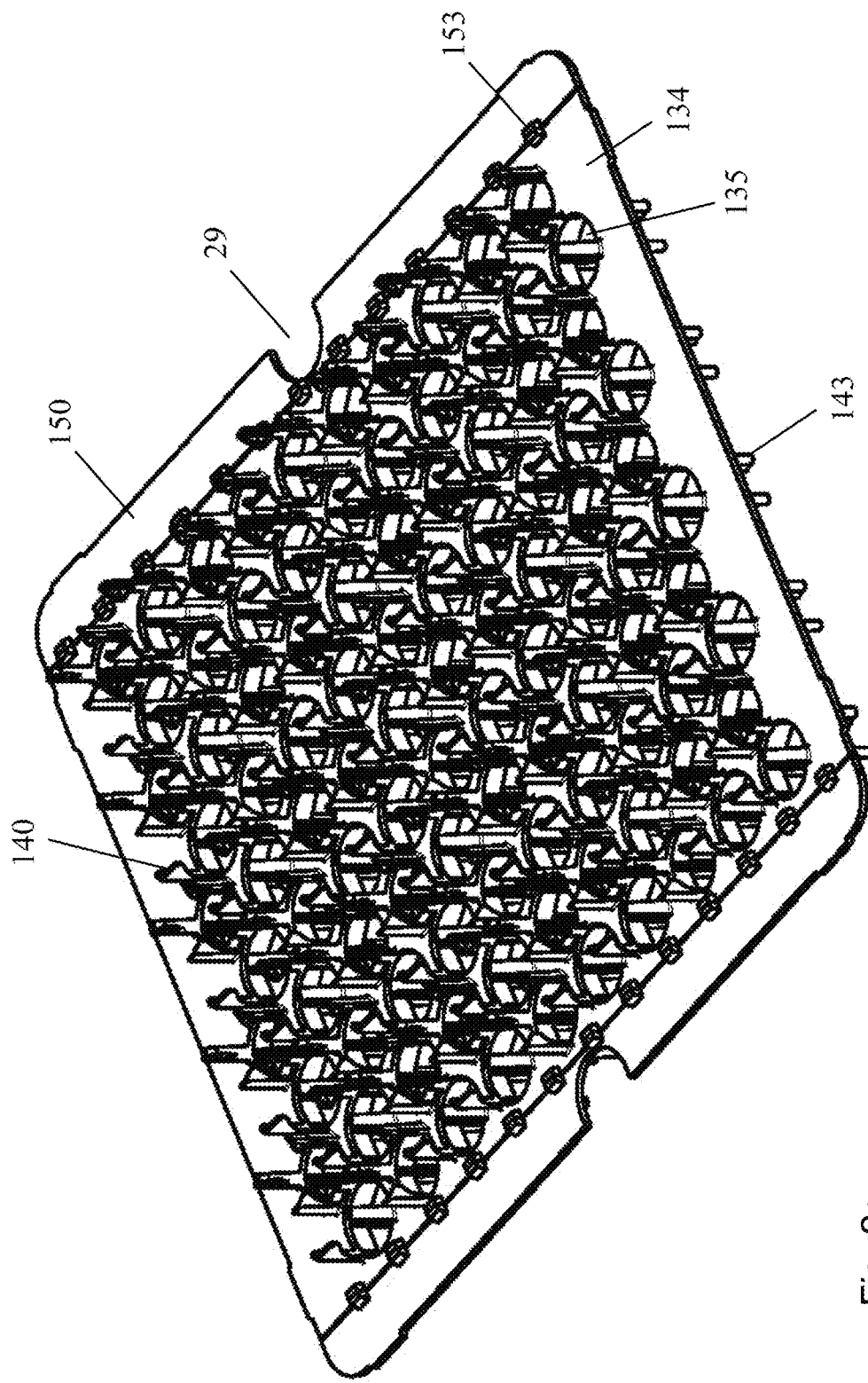
FIG. 2e shows the holding structure of FIG. 2a without containers in a perspective plan view.

FIG. 2e shows the holding structure of FIG. 2a without containers in a perspective plan view. As can be seen, the resilient holding tabs 140 are flag-like and formed with a holding nose protruding inward in radial direction, as shown in more detail in the greatly enlarged partial cross-section through this holding structure shown in FIG. 2g. According to FIG. 2g, the resilient holding tabs 140 are connected with the carrier 134 via a resilient base 140a protruding perpendicularly from the upper side of the carrier 134. The base 140a passes over into a portion 140b curved radially inward, which finally passes over into the holding nose 140c, on which the expanded rim 6 (see FIG. 1e) of the containers rests, as described above with reference to FIG. 1e for the first embodiment. Here, the holding nose 140c protrudes into the aperture of the carrier 134. The holding nose 140c passes over into a slanted insertion surface 140d extending slanted upward, which connects with the upper end of the holding tab 140. Due to the slanted insertion surface 140d on the upper side of the holding tab 140 and due to the curved portion 140b of the holding tab 140, which is open towards the bottom, the containers can be inserted selectively either from above or from below into the apertures of the carrier 134 and taken out again.

As the containers are inserted from above into the apertures, at first the bottoms or bottom ends of the containers get in contact with the slanted insertion surfaces 140d of the holding tabs 140. Upon further insertion of the containers the bottom ends or the bottoms of the containers slide downwards along the slanted insertion surfaces 140d and thereby resiliently spread the holding tabs 140 increasingly apart or flap or pivot them back. Upon further insertion of the containers finally the cylindrical side walls of the containers (see FIG. 1e) get in contact with the holding noses 140c and slide therealong, until eventually the undersides of the expanded rims of the containers rest loosely on the holding noses 140c of the holding tabs 140. Afterwards, the containers can be removed from the apertures of the carrier 134 either upward with reversed motion sequence of the holding tabs 140 and without resilient bending of the holding tabs 140 or downward with resilient bending of the holding tabs 140.

As the containers are inserted from below into the apertures, at first the upper ends of the containers get in contact with the curved portions 140b of the holding tabs. Upon further insertion of the containers the uppers ends of the containers slide upwards along the curved portions 140b and thereby resiliently spread the holding tabs 140 increasingly apart or flap or pivot them back. Upon further insertion of the containers the undersides of the expanded rims of the containers slide beyond the holding noses 140c of the holding tabs 140 and finally rest loosely on the holding noses 140c of the holding tabs 140. Afterwards, the containers can be removed from the apertures of the carrier 134 either downward with reversed motion sequence of the holding tabs 140 and with resilient bending of the holding tabs 140 or upward without resilient bending of the holding tabs 140.

Figure 2F:
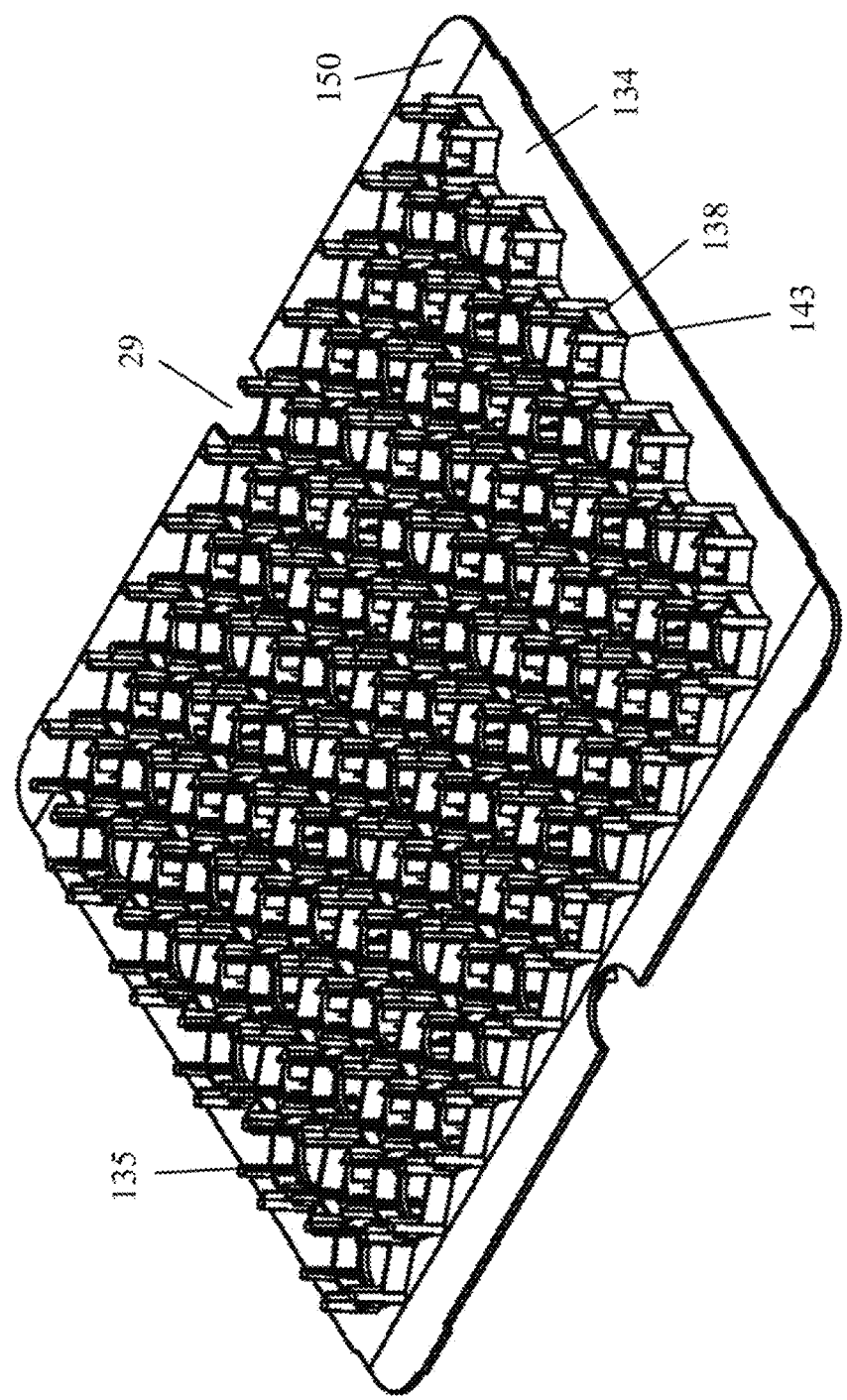
FIG. 2f shows the holding structure of FIG. 2a without containers in a perspective bottom view.

FIG. 2f shows the holding structure of FIG. 2a without containers in a perspective bottom view. The honeycomb-like, hexagonal configuration of the circumferential side walls 138 can be seen, and in their corner regions pins 143 protrude perpendicularly from the lower side of the carrier 134. These pins 143 serve as spacers when placing the carrier 134 on a supporting surface, for example on the bottom 11 of a transport and packaging container (see FIG. 2a), but at the same time prevent the contact of the containers with each other.

Figures 2H, 2I, 2J:
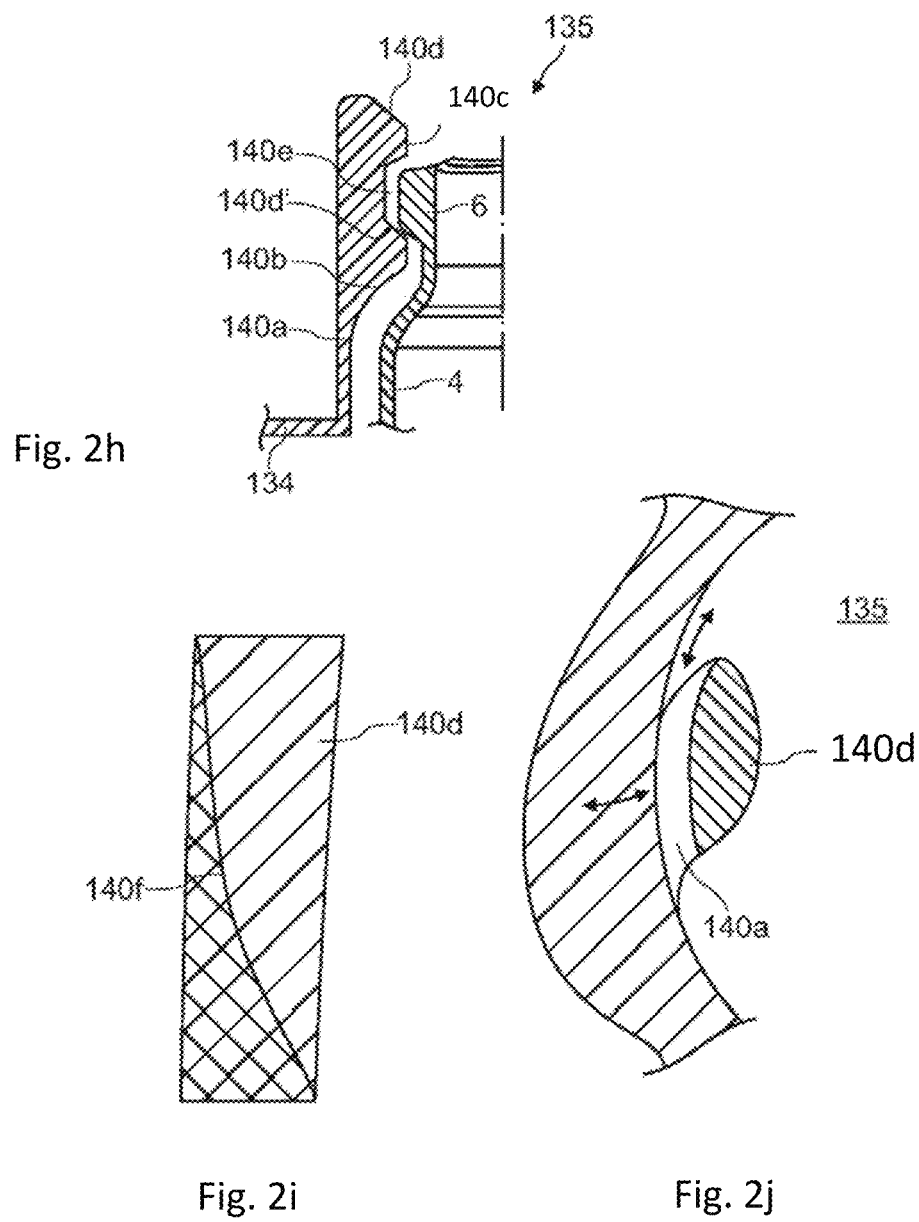

FIG. 2h shows the holding of a container in a holding structure according to a further embodiment of the present invention in a greatly enlarged partial sectional view. In contrast to the second embodiment, here the containers 6 are embraced in a positive-fit manner at their expanded upper rim portions 6 (rolled edge), wherein a sufficient radial clearance, as described above, is ensured, as indicated in FIG. 2h by the gap in the radial direction. As an alternative, in addition to this radial clearance a sufficient axial clearance may be ensured, as indicated in FIG. 2h by the gap in the axial direction. To this end, a C-shaped recess 140e is provided at the front end of the holding nose 140c (see FIG. 2g), which passes over into the holding nose 140c via slanted surfaces 140d'. In the holding position of FIG. 2h, the expanded rim portion 6 rests loosely and with radial clearance on the lower slope 140d' of the recess 140e. As shown in FIG. 2h, a sufficient axial clearance may be provided between the upper end of the expanded rim portion 6 and the upper slope 140d' of the recess. Overall, the expanded rim portion 6 is embraced by the holding tab 140 like a clamp and in a positive-fit manner. The slanted insertion surface 140d', the curved portion 140b and the slopes 140d' of the recess thereby allow insertion of the containers into the receptacles and their removal without too much effort by a resilient bending back of the holding tabs 140.

FIG. 2i is a greatly enlarged plan view of a slanted insertion surface of a holding tab according to a variant of the holding structure of FIG. 2a. According to FIG. 2i the slanted insertion surface 140d is overall twisted due to an arcuate ridge 140f formed thereon. This spiral slanted insertion surface 140d is formed in the same manner on all holding tabs of the apertures or receptacles. Overall, the slanted insertion surfaces are curved by an angle of less than 90°, if viewed in a plan view. In cooperation with the container, this causes that the holding tabs are not only pivoted back or folded back radially outward but at the same time rotated back with a movement component in the circumferential direction in correspondence to the geometry of the slanted insertion surfaces 140d, namely by an angle of less than 90°, as the containers are inserted into the apertures. Depending on the geometry of the arrangement of the holding tabs on the carrier, thus a collision of the holding tabs of directly adjacent apertures or receptacles can be prevented during the pivoting back or folding back of the holding tabs. In this way, the packing density of the containers on the holding structure can be further increased.

Figure 2K:
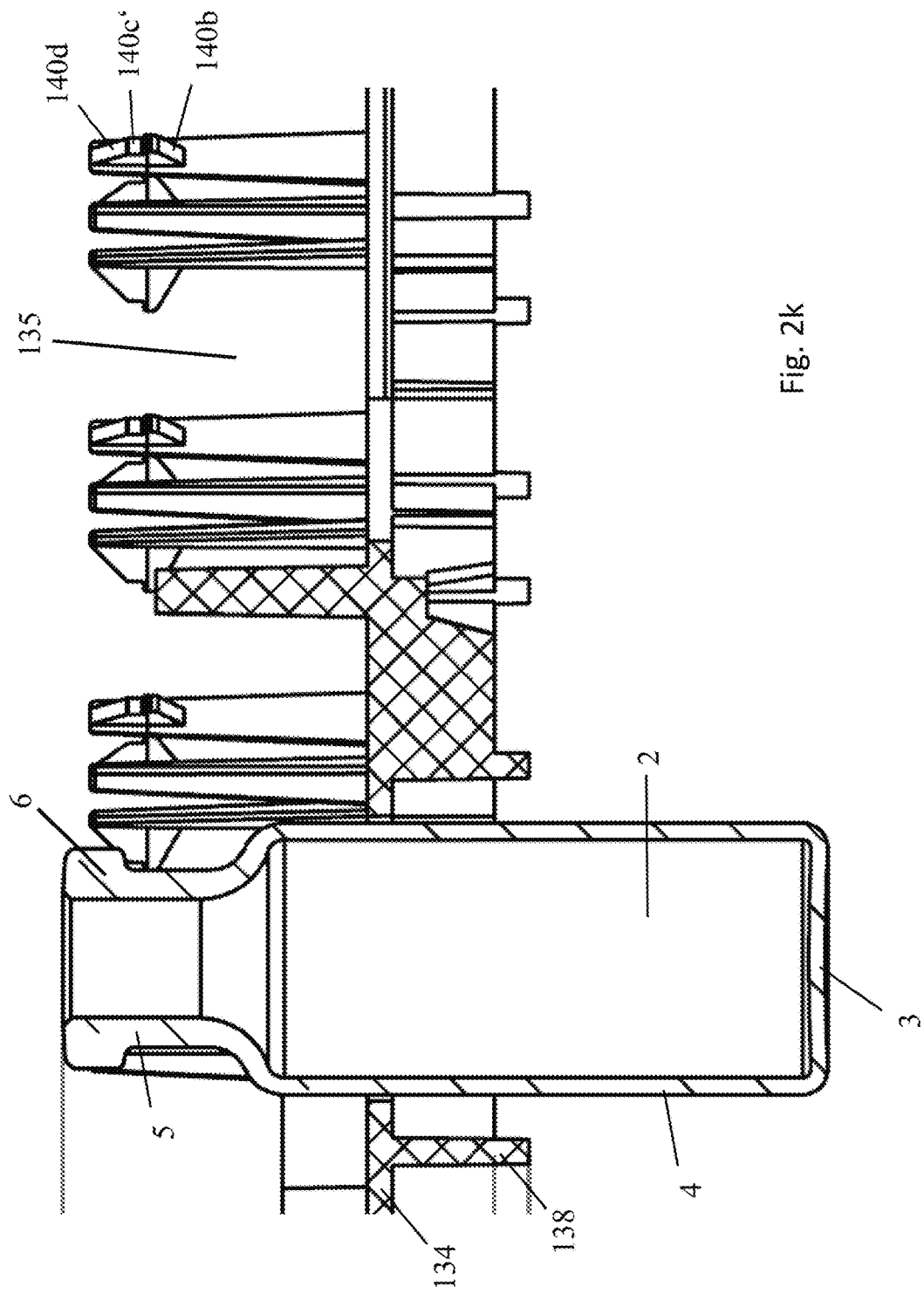
FIG. 2k shows a partial cross section through a further variant of a holding structure of FIG. 2a with containers retained therein.

FIG. 2j shows a further variant of the holding tabs for a holding structure according to FIG. 2a in a plan view, wherein the base 140a is twisted, if viewed in the axial direction, which causes both a radial component and a component in the circumferential direction upon the resilient pivoting back of the holding tabs as the containers are inserted from above into the aperture or receptacle as a result of the interaction of the slanted insertion surface 140d with the container, as schematically indicated by the two double arrows. FIG. 2k schematically shows the support of a container 2 in a holding structure, as shown in FIG. 2g.

FIG. 2m shows a further variant of the embodiment according to FIG. 2g with a modified configuration of the flag-like resilient holding tabs 140. While in the embodiment of FIG. 2g the transition region between the two slanted insertion surfaces 140b and 140d is flat or protrudes outward, in the embodiment of FIG. 2l the lower insertion surface 140b protrudes further into the aperture 135 than the upper slanted insertion surface 140d. The transition region 140c' extends substantially in vertical direction or is inclined relatively steeply downward. The upper rolled edge 6 of the vial 2 can rest loosely on this sloped transition region 140c' or on a step, which is formed by the upper side of the lower slanted insertion surface 140b. In any case, the resilient holding tabs 140 are configured such that a certain radial clearance exists between the front ends of the holding tabs 140 and the vials 2 held by them, so that in particular manufacturing tolerances of the vials 2 can be compensated.

FIGS. 2n to 2p show the insertion of a container into a holding structure according to a further variant of a holding structure in a motion sequence. According to FIG. 2n a notch 140g is formed at the front end of the upper insertion 140d facing the associated aperture, which connects to a projection 140h, which is relatively thin and thus is relatively easy to bend. In the holding position according to FIG. 2n the bottom of the rolling edge 6 of the vial rests loosely on this projection 140h. Here, between the rolled edge 6 and the front end of the upper slanted insertion surface facing the aperture a radial clearance may exist, as described above. FIG. 2p shows how the bottom 3 of the vial slides downwards along the upper insertion 140d during insertion from above into the associated aperture until the protrusion 140h is finally reached, as shown in FIG. 2o. Once the bottom 3 with its chamfered peripheral edge contacts the protrusion 140h, the contact force causes a depression of the protrusion 140h, thereby changing the contact angle (it becomes steeper) and the further sliding of the vial over the front region of the upper slanted insertion surface 140d is encouraged. When pressing the rolling edge 6 it exerts a force on the protrusion 140h so that a torque acts on the whole holding tab 140, which would turn the holding tab 140 to the inside. However, the protrusion 140h bends in the direction of the vial and the contact angle is changed so that the force now acts more in the direction of the base of the holding tab, so that the torque, which bends the holding tab 140 to the inside, can be advantageously reduced.

Figure 1F:
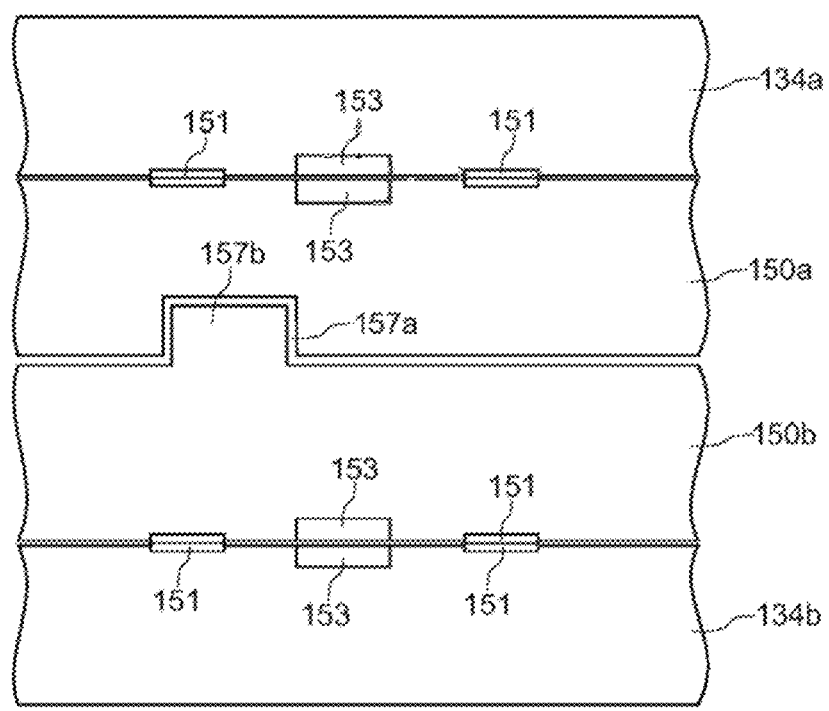
FIG. 1f shows a variant of the holding structure of FIG. 1a, which has protrusions and recesses of the members that can be removed or pivoted back, which serve to further enhance the packing density of the holding structure.

FIG. 1f shows in a greatly enlarged partial sectional view and in a plan view a further variant of the holding structure of FIG. 1b, wherein edges 150a, 150b of the planar carrier 134a, 134b can be pivoted back to further reduce the base area of the respective carrier, for example if this is to be transferred together with the containers to a processing station with constricted space, such as a freeze-dryer with limited floor space. For this purpose, the edges 150a, 150b are connected with the respective carrier via hinges 151. In particular, the hinges 151 can be formed as film hinges or snap hinges or spring hinges from a plastic material and integrally with the carrier 134.

According to FIG. 1f recesses 157a and/or protrusions 157b are formed on the members 150a, 150b that can be removed or pivoted back. The recesses 157a and/or protrusions 157b of the members 150a, 150b of a carrier that can be removed or pivoted back are formed corresponding to the recesses 157a and/or protrusions 157b of the members 150 of a directly adjacent planar carrier that can be removed or pivoted back so that a positive-fit between the recesses 157a and/or protrusions 157b can be established to define and stabilize the mutual positions of the carriers.

On the upper side of the carrier 134a, 134b and of the edges 150a, 150b, block-shaped stops 153 are provided at corresponding positions, which define in mutual abutment a coplanar alignment of the edges 150a, 150b and of the carrier 134 and prevent a folding-up of the edges 150a, 150b. The carriers can therefore also be placed in a transport and packaging container only at the edges (see FIG. 2a).

According to a further embodiment (not shown), the edges 150 can also be removed from the carrier 134. The edges 150 may of course be provided along all four longitudinal sides of the carrier 134.

FIG. 1g shows a further variant of the above holding structure of FIG. 1f, wherein the aforementioned protrusions 157a and recesses 157b are formed directly on the edge of the planar carrier 134.

FIG. 1h shows the cooperation of two adjacent holding structures 134 of FIG. 1g in a schematic plan view. The undulating protrusions 157b and recesses 157a of two adjacent carriers 134 are formed corresponding to each other so that the edges of the carriers 134 may directly engage each other by a positive-fit, which enables a mutual stabilization of the positions of the carrier 134 during the processing or handling. According to this embodiment, the carriers 134 may also be displaced further by one protrusion 157b along the edges and placed again in a positive-fit engagement so that the two carriers are then offset to each other by one protrusion 157b.

Figure 3A:
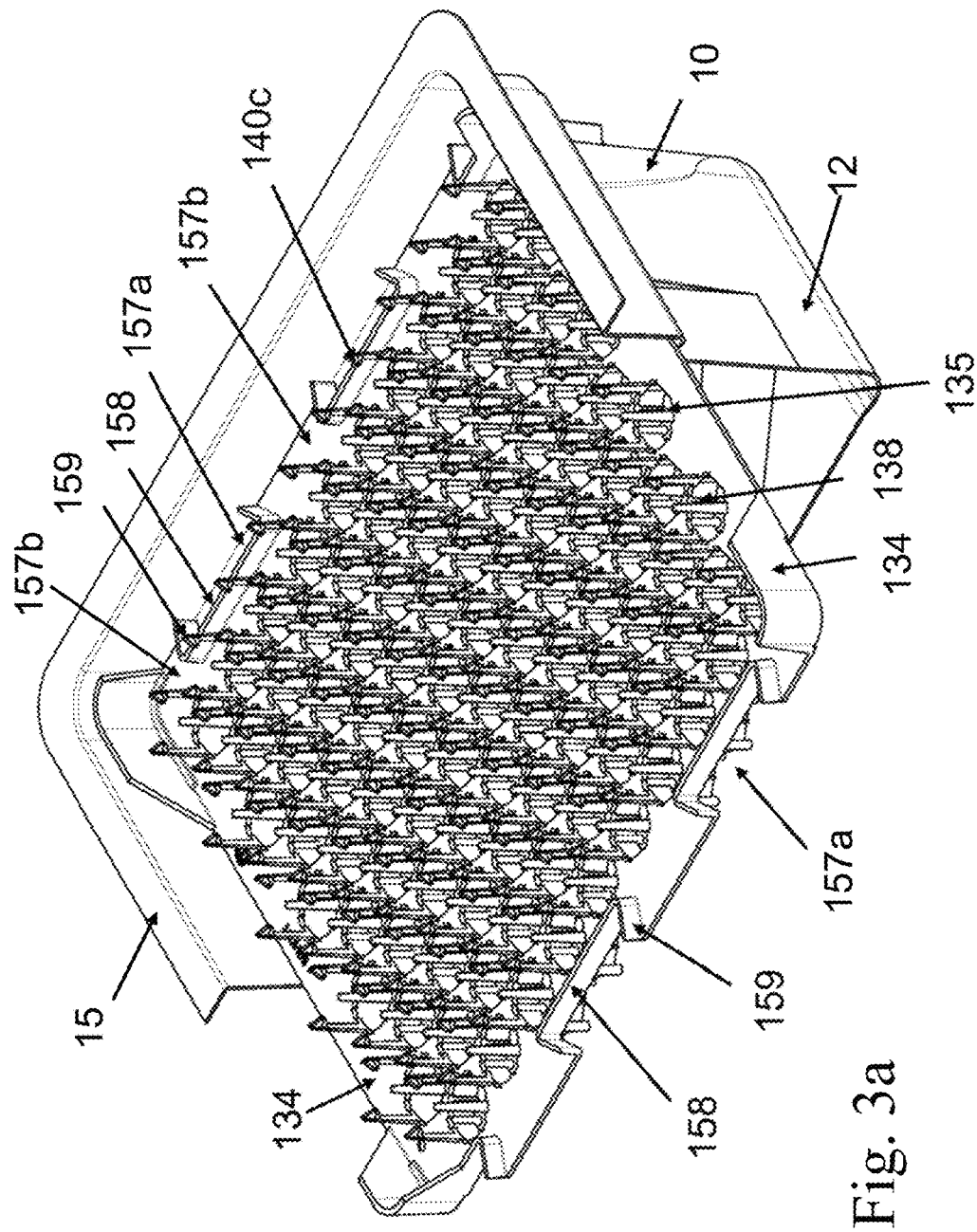
FIG. 3a shows a holding structure according to a further embodiment for use in a process according to the present invention in a perspective plan view.

FIG. 3a shows a holding structure according to a further embodiment of the present invention in a perspective plan view that may also be claimed independently. According to FIG. 3a a plurality of protrusions 157b and recesses 157a are formed along the two longitudinal sides of the holding plate 134 alternately and at regular intervals to each other. If viewed in a plan view, these comprise a base area basically of a triangular or polyhedral shape and are configured to correspond to each other, so that they can be latched directly to one another.

Figure 3B:
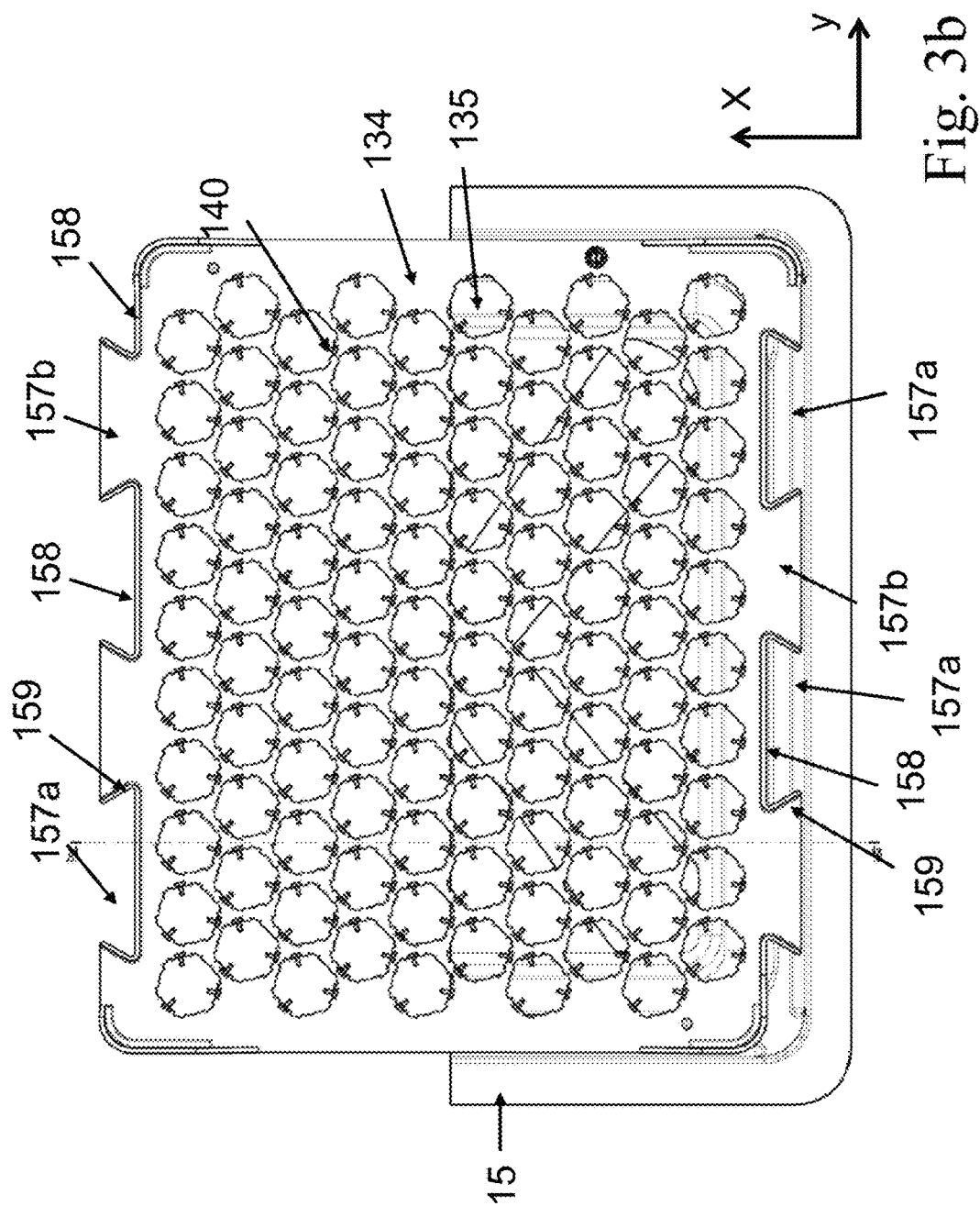
FIG. 3b shows the holding structure of FIG. 3a in plan view.

As can be concluded from the plan view of FIG. 3b, two holding structures can be latched together so that these are aligned in the transverse direction (x). For this purpose, the recess 157a is formed only half in the lower right-hand corner region of the holding plate 134. In the opposite upper right-hand corner portion of the holding plate 134, however, the corresponding protrusion 157b is also formed only half and passes over into a rounded corner of the hold plate 134.

Due to the aforementioned configuration of the protrusions 157b and recesses 157a, however, two holding structures may in principle also be latched with each other so that these are offset to each other in the transverse direction (x), i.e. so that these are not aligned.

For latching two holding structures, one of the holding structures may be raised by means of a raising device in a direction perpendicular to the plane of the holding plate 134. Subsequently, the two holding structures are moved towards each other until finally, if viewed in a plan view, the protrusions 157b and recesses 157a of the adjacent holding structures overlap each other. By a subsequent lowering of the holding plate 134 perpendicular to the plane of the holding plate 134, finally, the protrusions 157b and recesses 157a engage with each other in a positive-fit manner. This procedure may be performed manually but also fully or semi-automatically. Here, the holding plates 134 may be pre-loaded with vials. In general, however, the loading of the holding plates 134 with vials may be performed only after the holding plates 134 have been coupled with each other.

Due to the above configuration of the protrusions 157b and recesses 157a overall a latching effect in the manner of a dovetail coupling is implemented. As will be readily apparent to the person skilled in the art when studying the above description, in general any other positive-locking or frictional coupling techniques may be used for a temporary, releasable coupling of two holding structures.

As can be concluded from the perspective plan view of FIG. 3a, side walls 158, 159 are formed at least in sections along the edges of the protrusions 157b and recesses 157a, which protrude perpendicularly from the surface of the holding plate 134. These side walls 158, 159 follow the contour of the associated recess 157a or of the associated protrusion 157b and act as a stop and guiding surface, which prevents that the holding plates 134 slide or slip one above the other. More specifically, according to FIG. 3b a side wall 158 is formed along the front side of the protrusions 157b on the upper edge of the holding plate 134, which is followed by a side wall 159 in the region of the adjacent recesses 157a but which do not extend over the entire depth of the recesses (in x-direction). At the opposite bottom edge of the holding plate 134, however, the side walls 158 are formed along the base of the recesses 157a, while the angled side walls 159a extend along the angled sides of the recesses 157a but not over their entire depth (in the x-direction). According to FIG. 3c the side walls 158, 159 further protrude from the upper side of the holding plate 134 as the holding devices 140, in case the holding plate 134, if no containers are held by the holding devices 140, can be stacked on top of each other.

As shown in the greatly enlarged partial plan view of FIG. 3e in the latched state the side walls 158a of the lower plate 134a abut directly the side walls 158b of the upper holding plate 134b. Furthermore, also the angled side walls 159b of the upper holding plate 134b abut directly the angled side walls 159a of the lower holding plate 134a.

FIGS. 3e and 3f show as a further example of a form-fitting coupling of two holding plates 134a, 134b according to a further embodiment in a greatly enlarged partial plan view and in a partial section along the line A-A, according to FIG. 3e. According to FIG. 3e a resilient holding tab 148 protrudes perpendicularly from the rectangular protrusions 157b of the lower holding plate 134a towards the associated recess of the upper holding plate 134b. At the front end of the resilient tab 148, a spherical protrusion 149a is formed, which engages in a corresponding receptacle 149b on the upper side of the upper holding plate 134b. For a coupling with each other the holding plates 134a, 134b may be pushed towards each other, until the front end of the resilient tab 148 with the protrusion 149a finally gets in contact with the upper side of the upper holding plate 134b. For preventing a sliding of the two holding plates 134a, 134b one above the other, also according to this embodiment stop and guiding surfaces may be provided, particularly as side walls protruding perpendicularly from the upper side of the holding plates 134a, 134b, as described above with reference to FIG. 3a. Particularly, in the embodiment of FIG. 3d such side walls would have to be provided laterally adjacent to the resilient tabs 148.

Figure 4A:
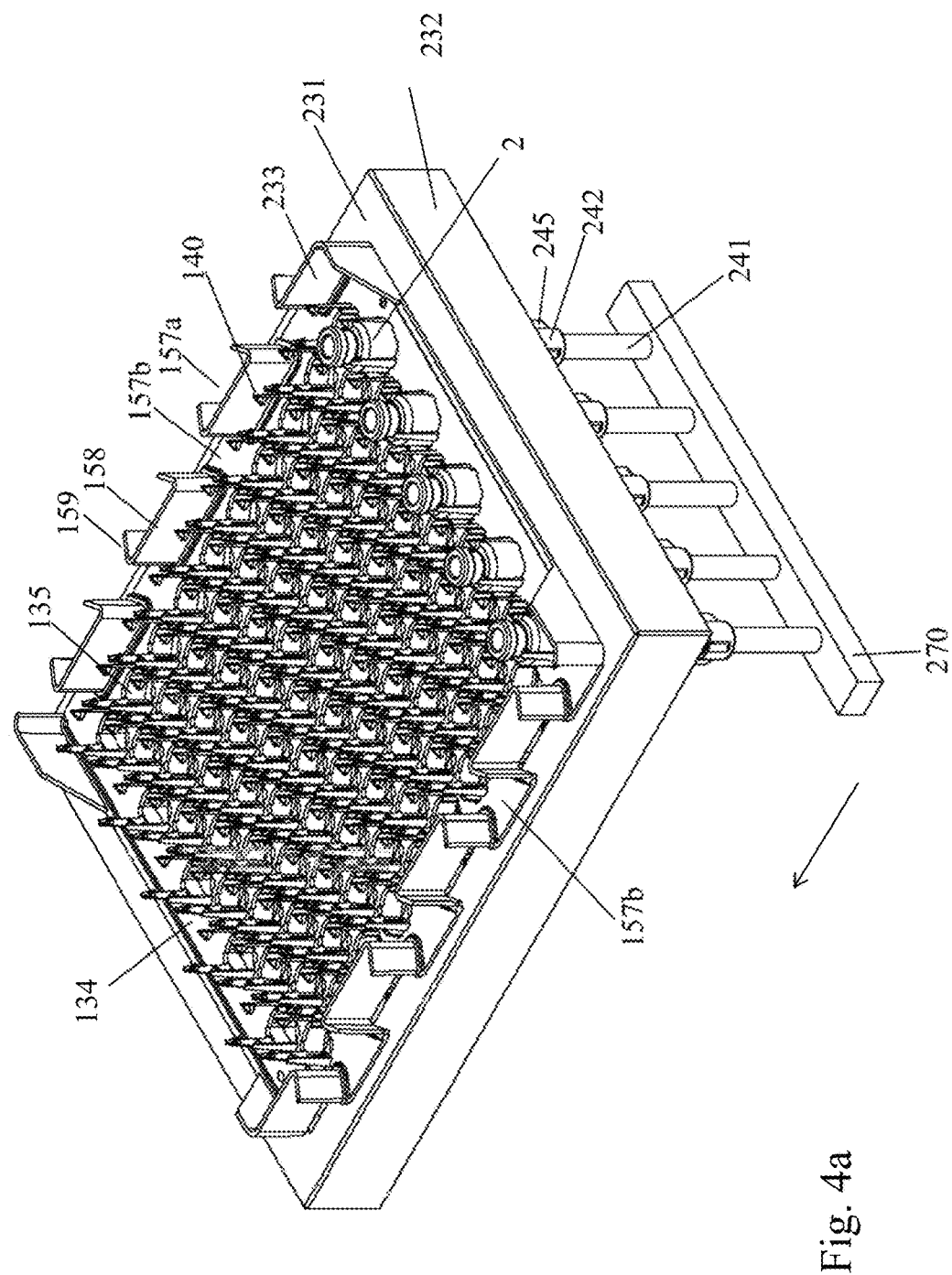
FIG. 4a shows a section of a processing station for the treatment or processing of vials according to the present invention, while the vials are held in a raised position in a holding structure according to FIG. 2d.

FIG. 4a shows a section of a processing station for the treatment or processing of vials while being held in a raised position in a holding structure according to FIG. 2d. The processing station comprises a displacement device 230 having a lifter 270 which carries and guides a plurality of push rods (see FIG. 7a). The supporting plate 134 together with its projections 157a and recesses 157b formed on the edge is accommodated in the correspondingly formed guiding plate 231. In the receptacle formed by the side wall 232 an apertured plate, as shown in FIG. 8a, may be accommodated precisely positioned in order to precisely position the push rods relative to the holding plate with the vials 2 held thereon.

Figure 6C:
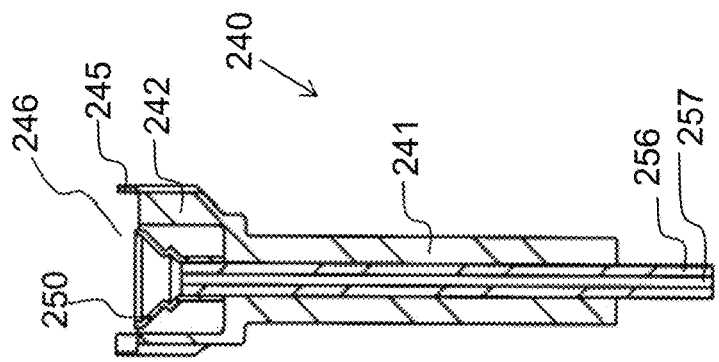
FIG. 6c shows a cross section along B-B of FIG. 6b.
Figure 6B:
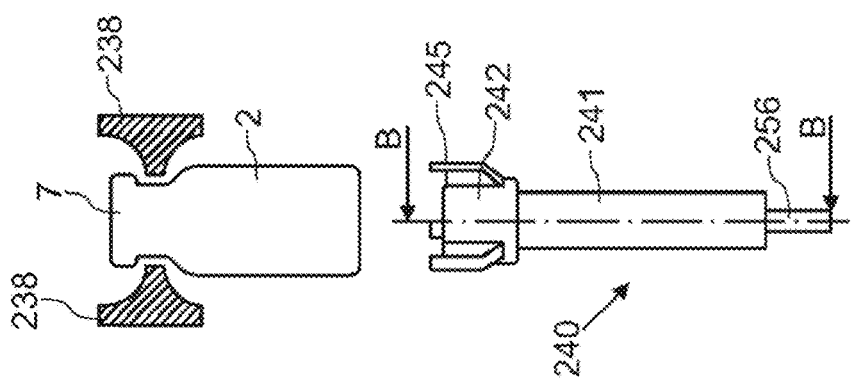
FIG. 6b the push rod according to FIG. 6a prior to its engagement with the vial, wherein the negative pressure sucker, guided in the push rod, is visible.
Figure 6A:
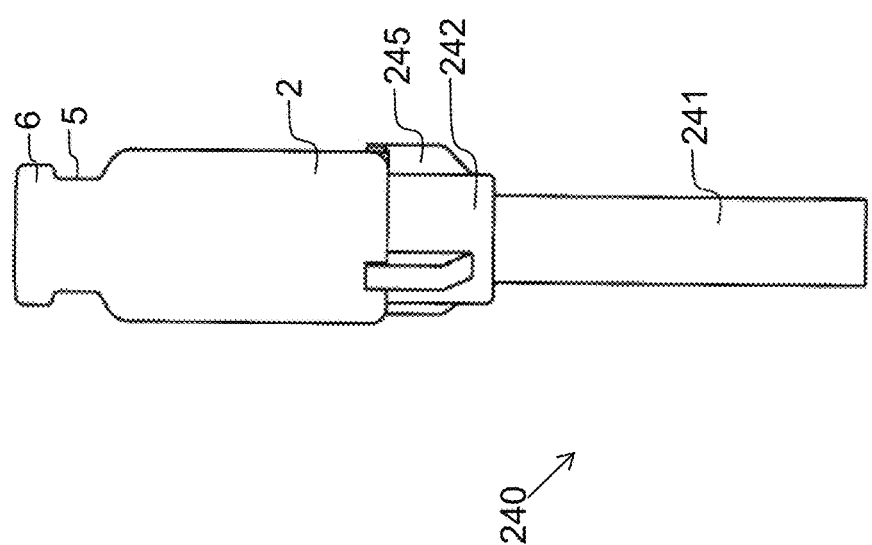
FIG. 6a is a side view of the cooperation of a push rod of the processing station according to FIG. 4a and a vial held by it.
Figure 7A:
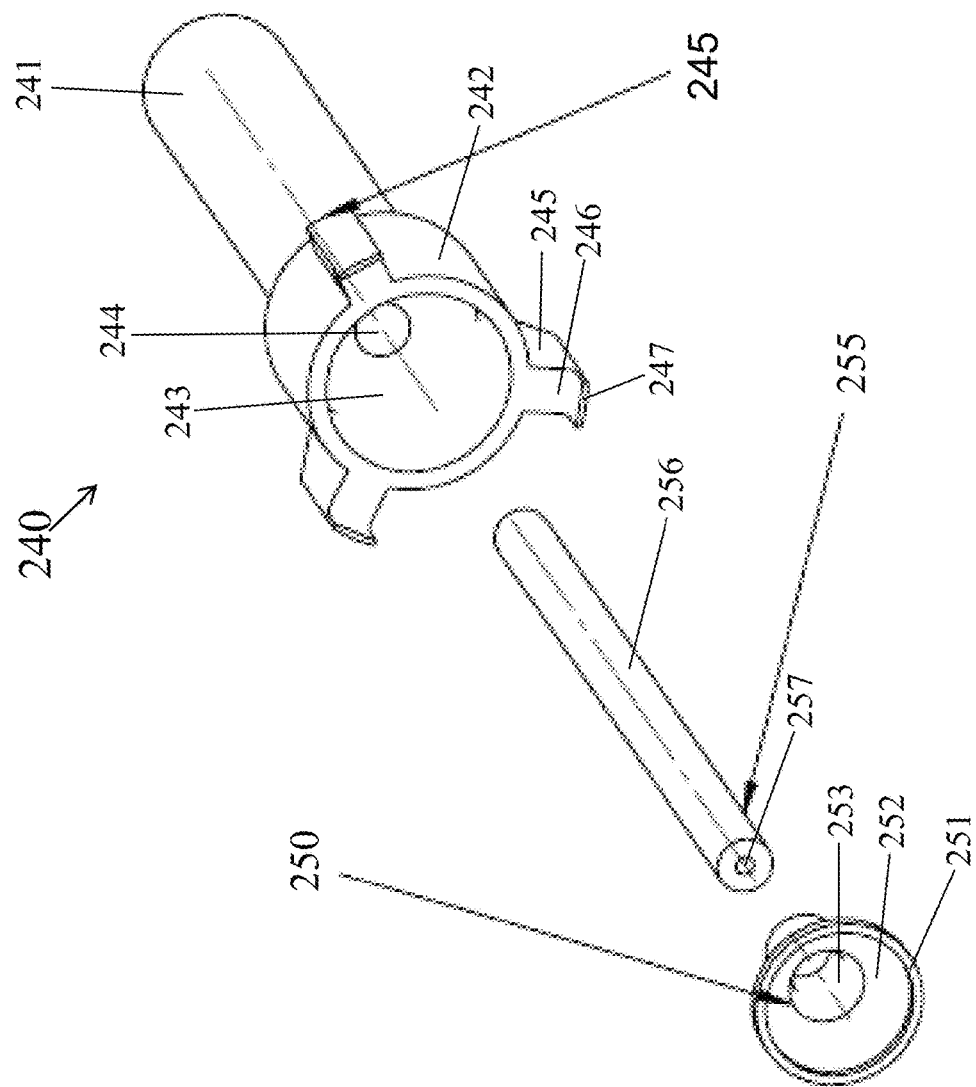
FIG. 7a is an exploded view of the push rod of FIG. 6b and the negative pressure sucker.
Figure 8A:
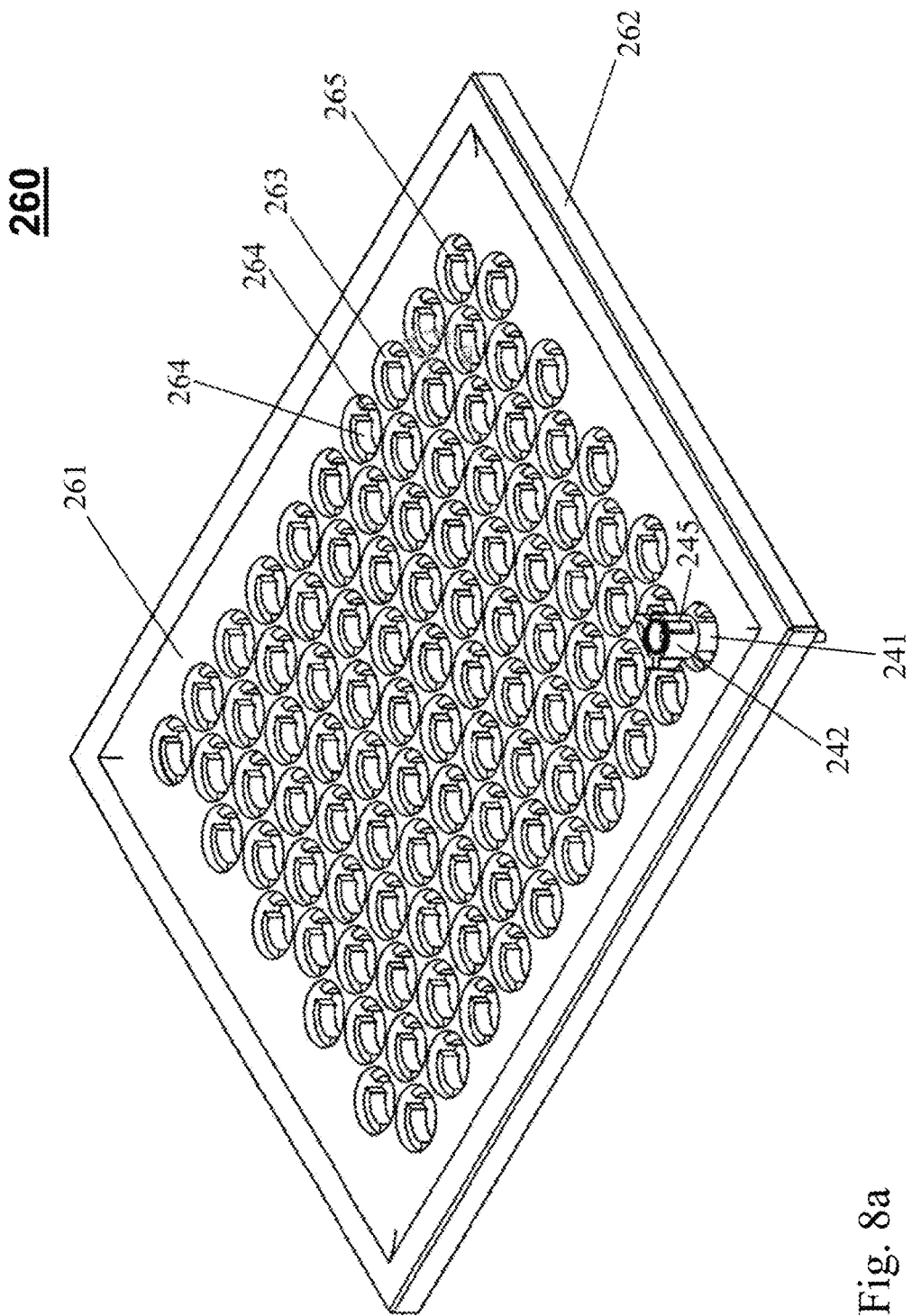
FIG. 8a is an apertured plate with a guidance structure for guiding and positioning of the push rod according to FIG. 7a in a perspective view.
Figure 8B:
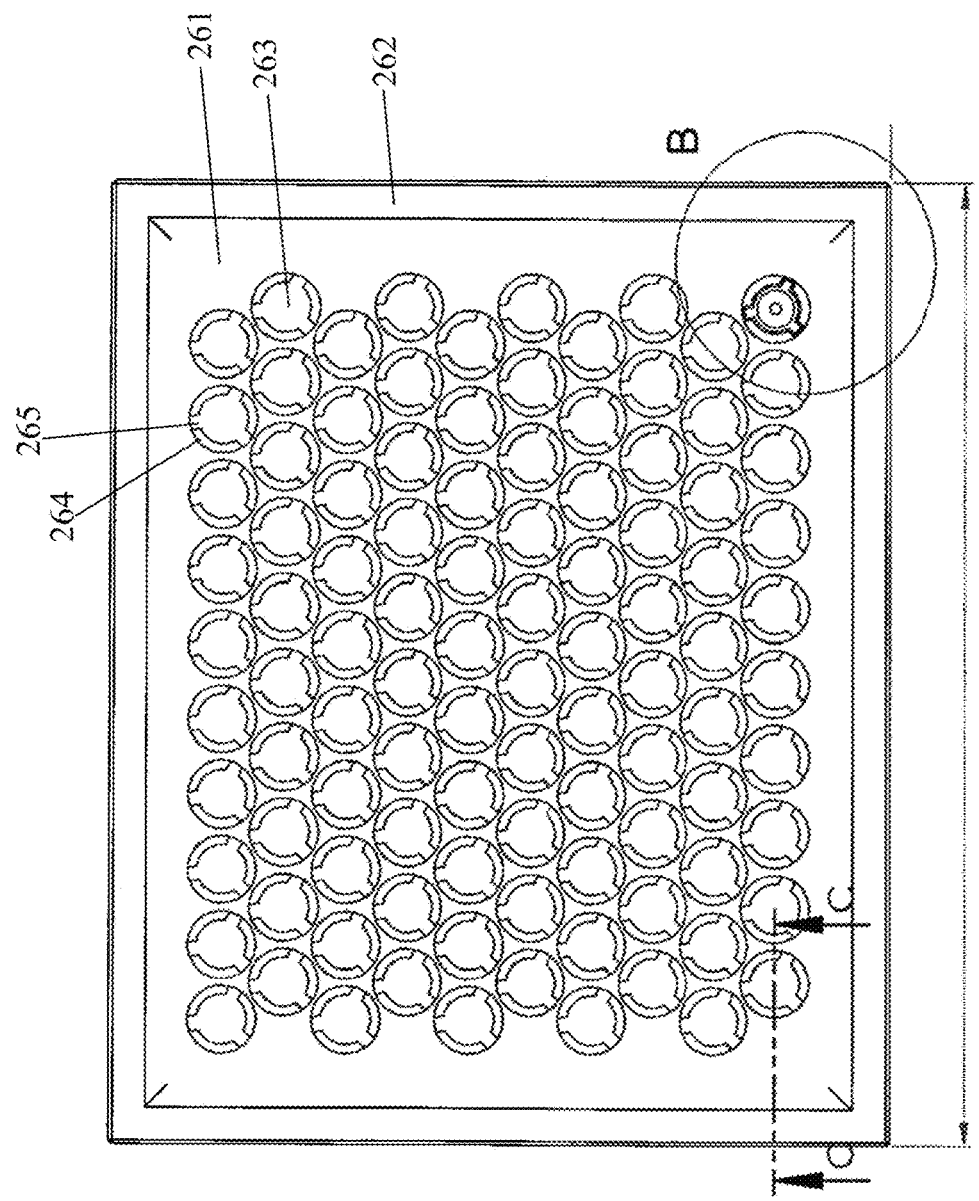
Figure 8D:
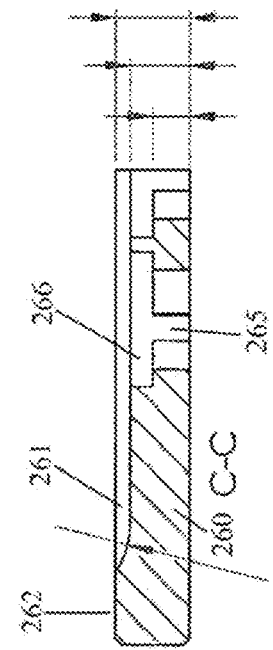
FIG. 8d is a sectional view taken along C-C of FIG. 8b.
Figure 8C:
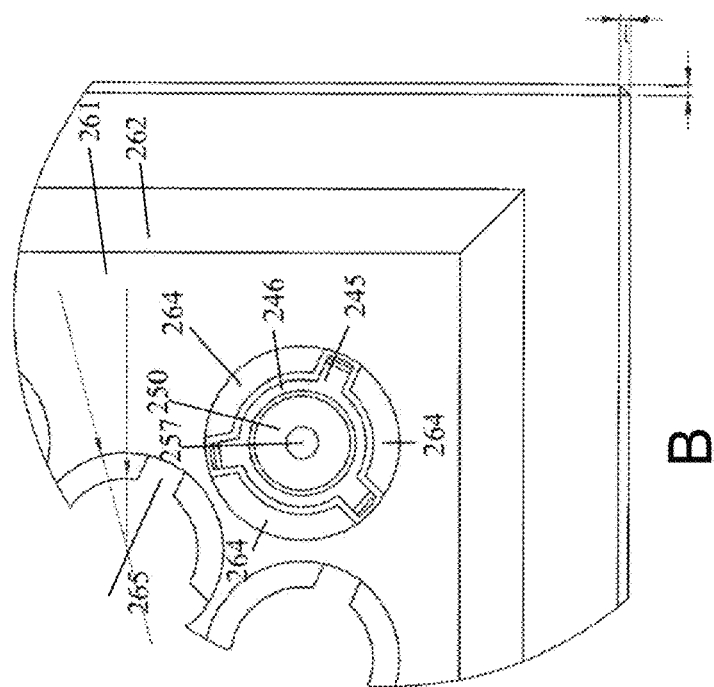
FIG. 8c shows a detailed view from the plan view of FIG. 8b.

According to FIG. 7a, each push rod 240 acting as a vertical displacement device has a shaft 241 with a holding ring 242, from whose peripheral edge three holding arms 245 protrude at equidistant angular spacing to each other, whose upper surfaces all together define a plane, which serves as a bearing surface 246 on which the bottom of the vial to be held rests, as shown in FIG. 6a. The vials are supported by the projections 247, which protrude perpendicularly from the holding arms 245. Here, the bottom edge of the vial 247 is embraced by the projections, whereby the position of the vials on the associated push rod can be precisely defined and whereby a lateral slipping of the vials can be prevented while they are supported by a push rod.

For this purpose, the projections 247 may respectively embrace the bottom edge of a vial tightly, in particular by clamping. Suitably, the holding arms 246 and/or protrusions 247 are sufficiently flexible for this purpose, for example, formed from a plastic material so that tolerances at the lower end of the vials can be readily compensated.

Such a push rod can adjust a vial against the holding force exerted by the holding arms of the holding plate and in vertical direction relative to the holding plate, for displacement to a raised position for the treatment or processing in a processing station.

As shown in FIG. 7a, an axial through-hole 244 is formed in the shaft 241, which serves as an axial guide for the tubular rod 256 of a sucker 250. An axial through-hole 257 is formed in the rod 256, which is connected to a negative pressure generating device, for example a suction pump. The rod 256 can be displaced in axial direction in the shaft 241.

Figure 7B:
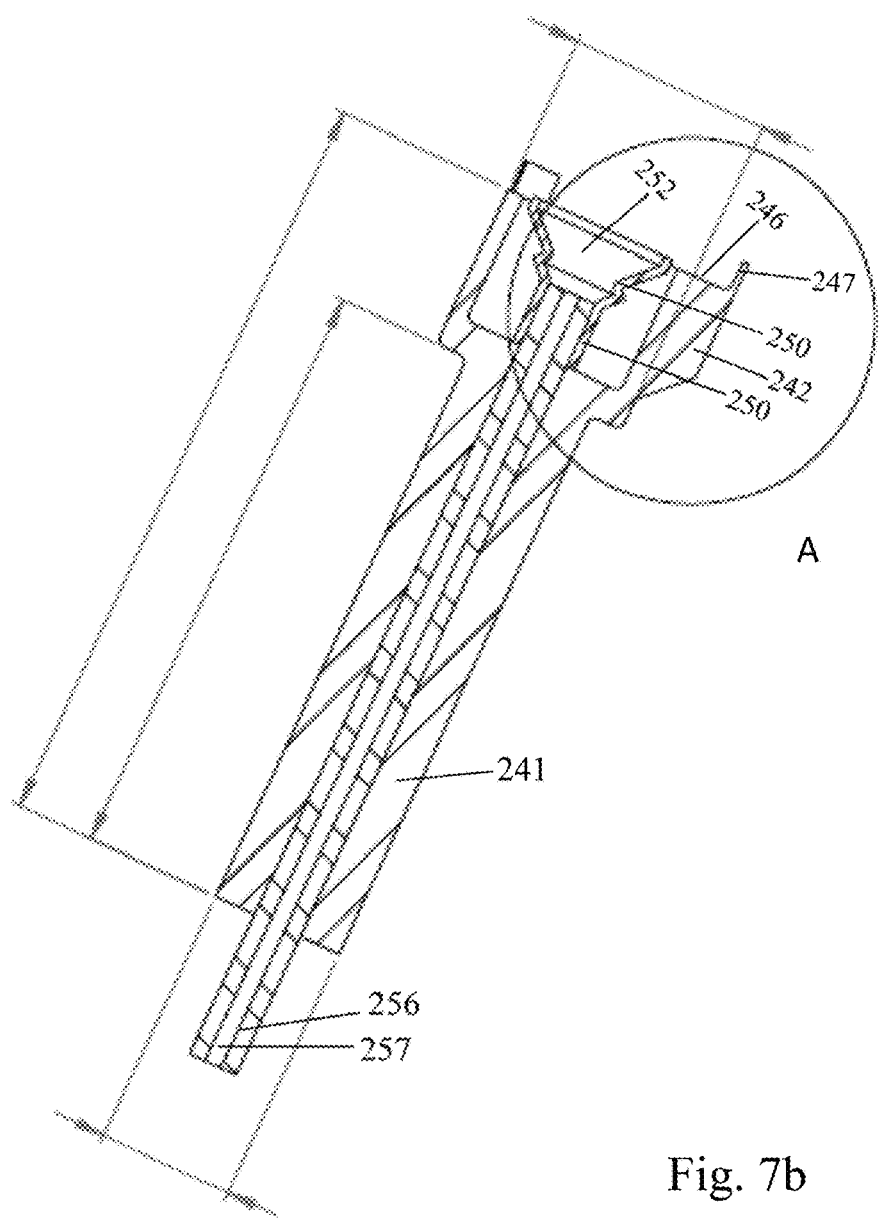
Figure 7C:
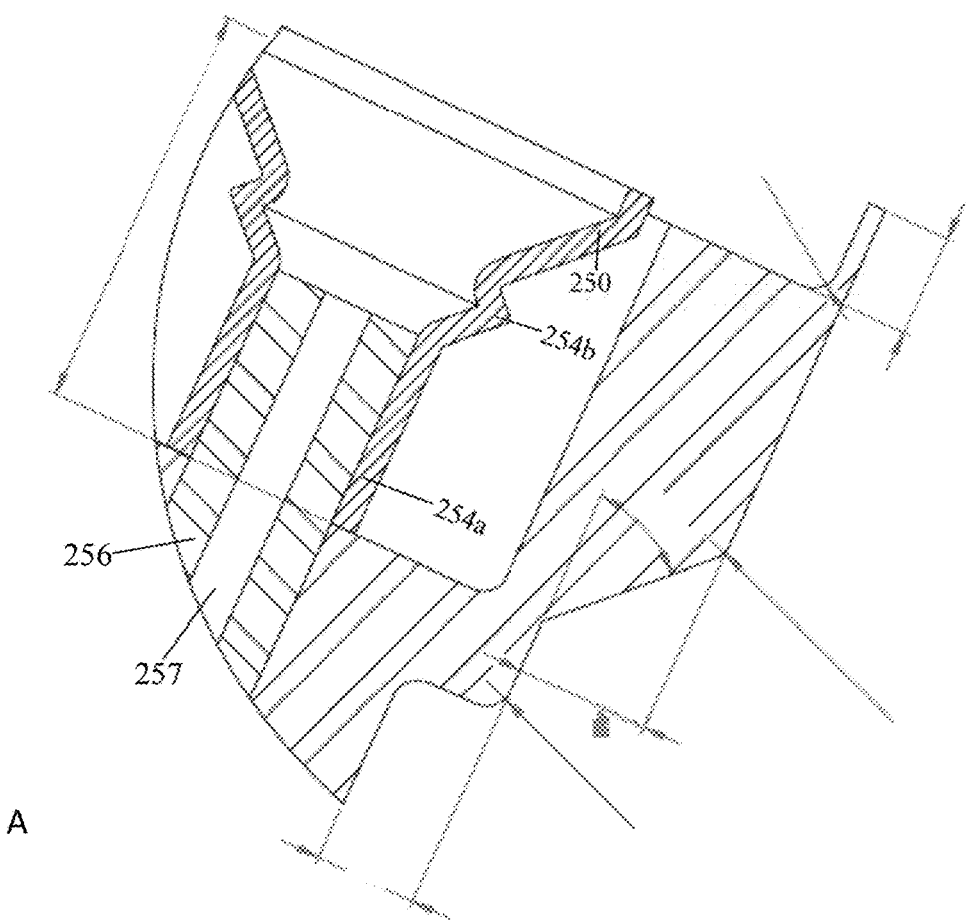
FIG. 7c shows a magnified sectional view of circle A in FIG. 7b.
Figure 7D:
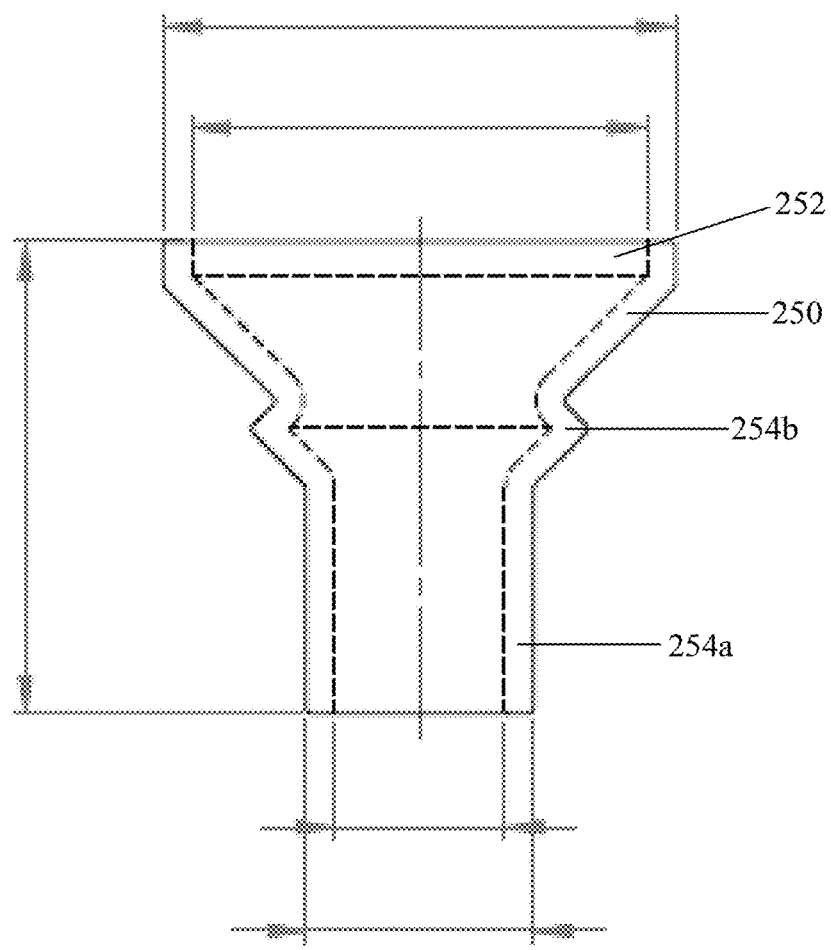

A suction cap 250 made of a resilient material such as rubber or silicone is clipped on the free front end of the rod 256. A funnel-shaped cavity 252 is formed in the suction cap 250, which communicates with the negative pressure generating device (not shown) via the aperture 253 and the through-hole 257 of the rod 256. The suction cap 250 is provided with one or plural corrugations 254b (see FIGS. 7c and 7d) and can snuggle tightly to the bottom of the associated vial by pushing-up the rod 256. As can be concluded from FIG. 7b, the suction cap 250 can be accommodated completely in a receptacle which is formed in the holding ring 242 at the front end of the push rod. The suction cap 250 can be fully submerged in this receptacle, so that it does not protrude beyond the supporting surface 246 of the holding ring 242. However, the suction cap 250 may be moved by pushing-up the rod 256 so far until it eventually gets in contact with the bottom of a vial to be displaced. This requires a certain degree of mobility of the rod 256 relative to the shaft 241 of the push rod 240.

Hereinafter, the basic principles of a process according to the present invention for the treatment or processing of vials is first described with reference to FIGS. 6a to 6c.

For raising a vial to a raised position, according to FIG. 6a, the shaft 240 is raised from the home position (comparable to the position shown in FIG. 6b) until the holding ring 242 at the front end of the shaft 241 gets in contact with the bottom of a vial 2. In this position the bottom of the vial is supported on the supporting surface at the front end of the holding ring 242 and the bottom edge of the vial is embraced by the holding arms 245 and the protrusions 247 (see FIG. 7a) formed thereon. In this position the suction cap 250 may be retracted back into the receptacle 243 in the holding ring 242.

In the raised position the vial is either transferred to another conveyor (not shown) or remains in the immediate vicinity of the push rod 240. For the treatment or processing of the vials, generally these may be held at or in a processing station by means of separate holding devices 238, as shown schematically in FIG. 6b. In such a case, the push rod can release the vials 2 for the treatment or processing as shown in FIG. 6b, it can, for example, be displaced or pivoted away laterally or downwards.

Of course, however, the push rod 240 may be also used solely for holding or supporting the vial 2 during the treatment or processing. In such a case, the push rod then remains at a suitable height position for the treatment or processing at or in the processing station and thereby secures the position of the vials 2 relative to the processing station. During the treatment or processing the push rod may be used additionally for an appropriate displacement of the vials 2 in axial direction and/or for rotating the vials (the push rod 240 acts also as a turntable) and/or for tilting or pivoting of the vials (the push rod 240 is tilted). For this purpose, a suitable holding force of the holding ring 242 for holding the vials 2 must be provided.

During the treatment or processing of the vials 2, those may in principle be continuously accommodated or at least guided in the apertures or receptacles of the holding structure, for example for stabilizing their position during the treatment or processing. In general, however, the vials 2 may also be completely raised out of the apertures or receptacles of the holding structure and released during the treatment or processing.

After the treatment or processing in or on a processing station, the vials need to be retracted back into a lower position, particularly into the apertures or receptacles of a holding structure as described above. For this purpose, as shown in the partial sectional view according to FIG. 6c, the suction cap 250 is positioned such that it is flush with the supporting surface 246 of the holding ring 242 or extends slightly beyond it or is retracted to it. For lowering the vial 2, the push rod 240 is positioned such that the supporting surface 246 again gets in contact with the bottom of the vial 2. If the push rod 240 was not retraced during the treatment or processing of the vial 2, an anew displacement is not required for this purpose. By applying a negative pressure to the suction cap 250, it snuggles to the bottom of the vial 2 and the bottom can be sucked toward the supporting surface 246 of the push rod. If necessary, the holding devices 238 of the processing station (see FIG. 6b) can now release the vial 2. Subsequently, the push rod 240 is lowered. The vial follows the downward displacement of the push rod 240.

Figure 4F:
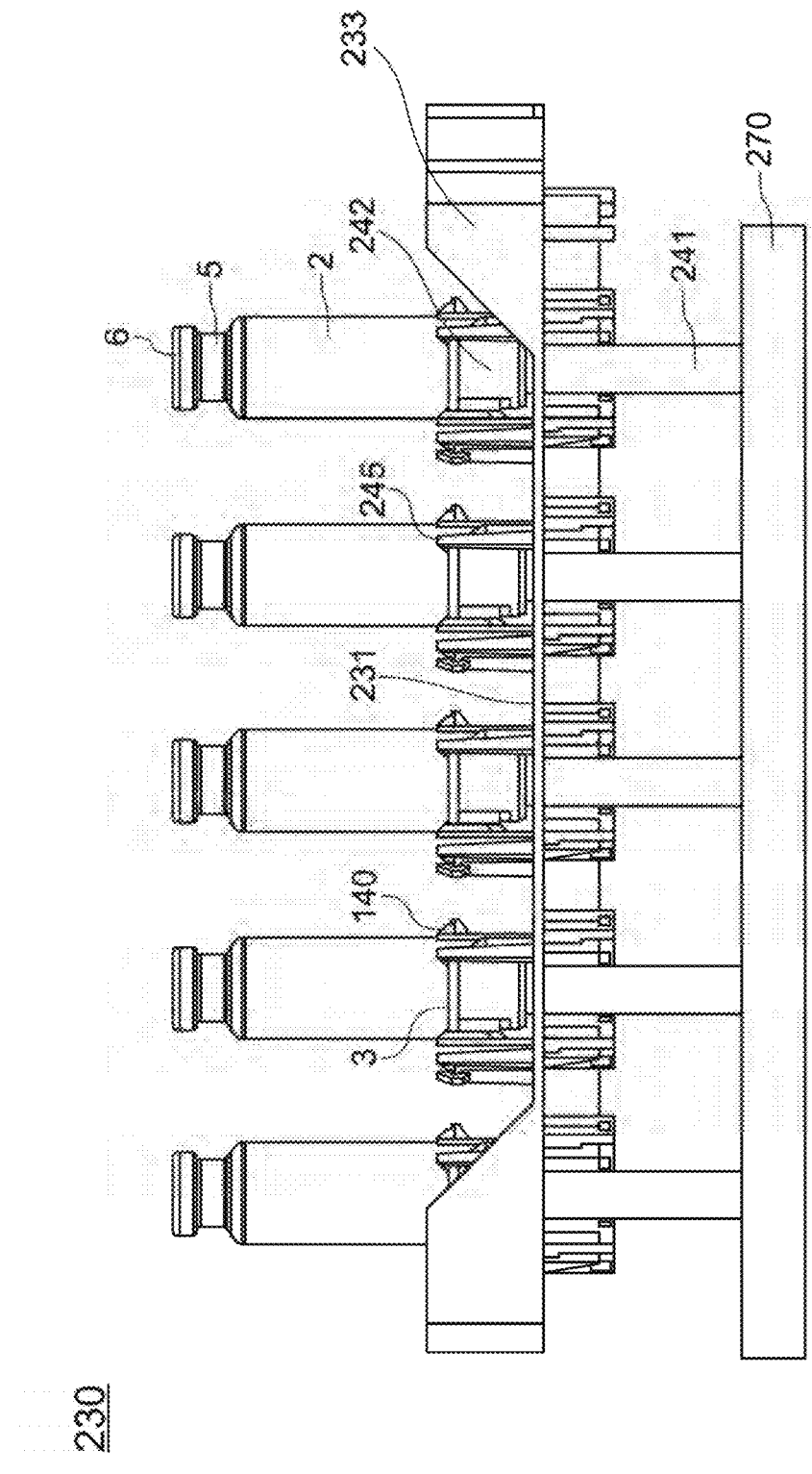
FIG. 4f shows a fourth step in the sequence of the process steps of FIG. 4b.
Figure 4G:
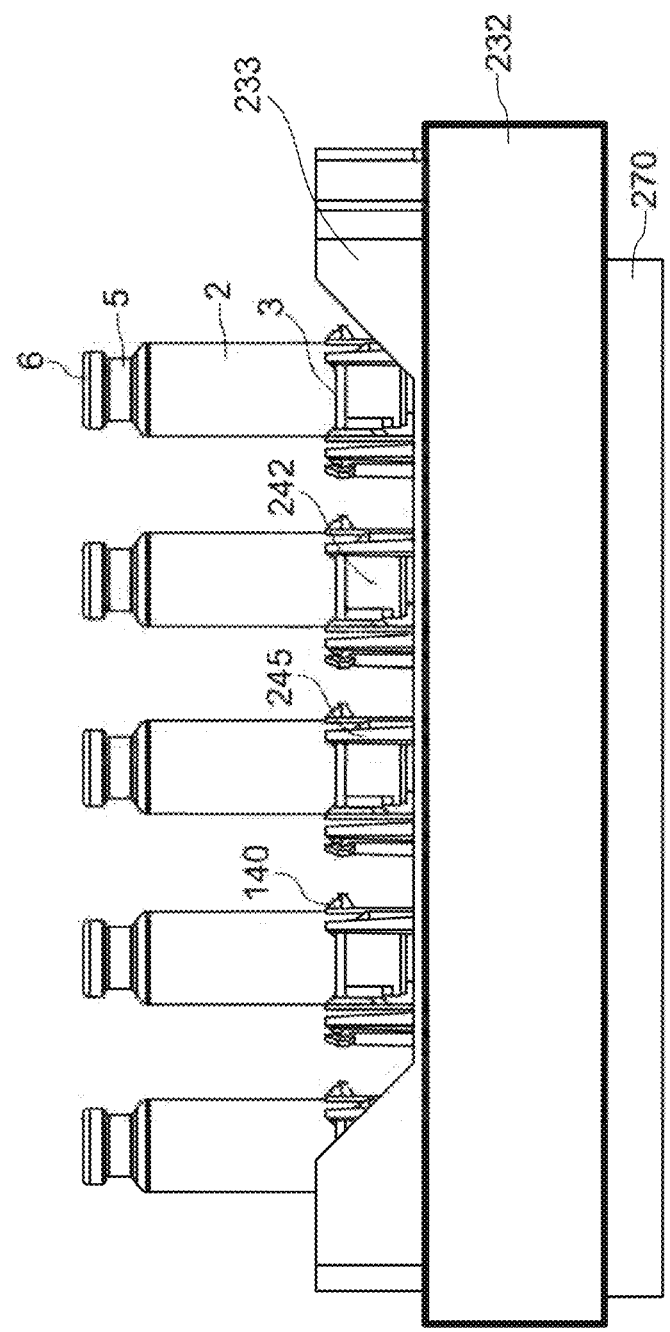
FIG. 4g shows a fifth step in the sequence of the process steps of FIG. 4b, wherein the containers are in a raised position.
Figure 5A:
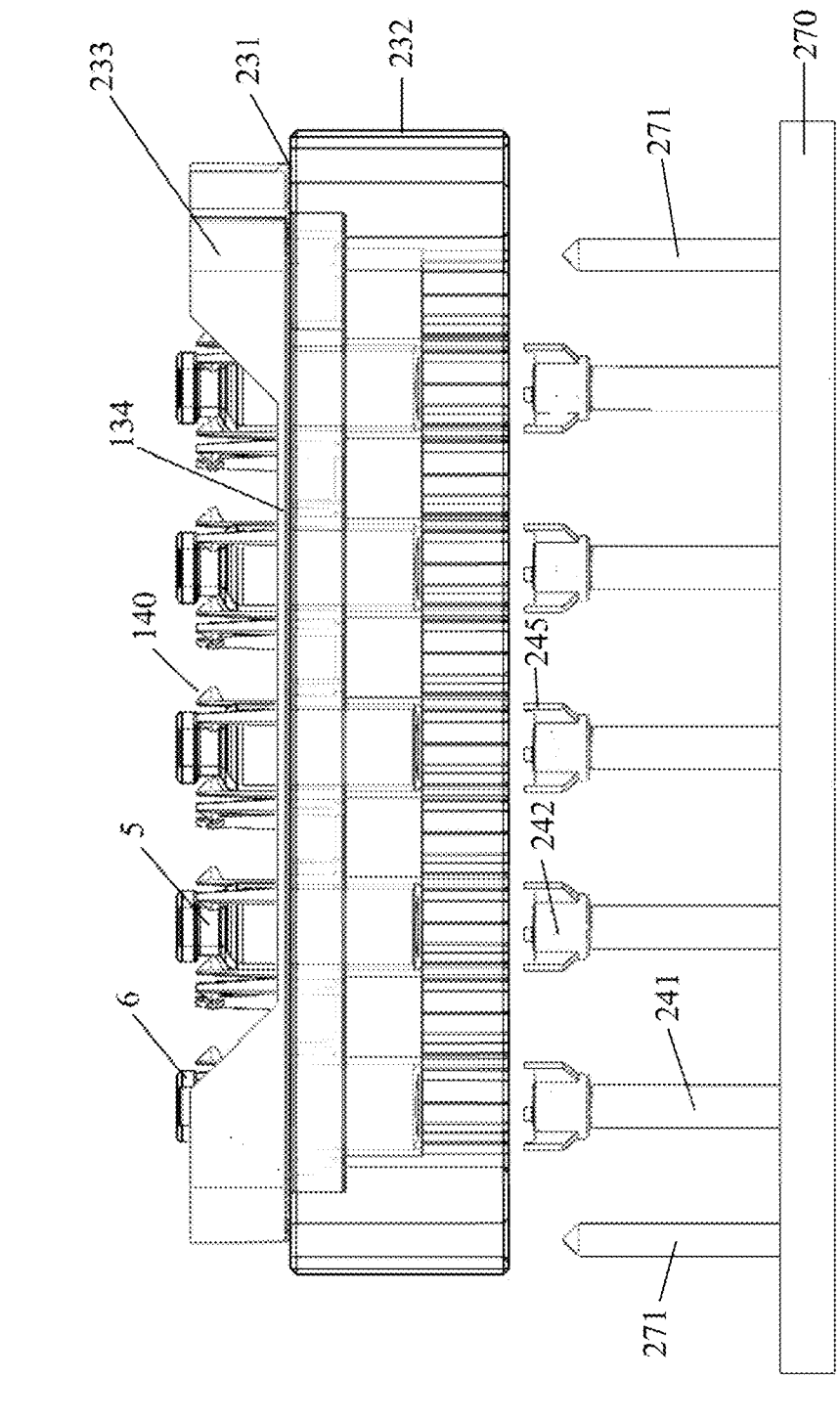
FIG. 5a shows a side view a first step in a corresponding sequence of process steps according to a further variant of the process according to the present invention.
Figure 5B:
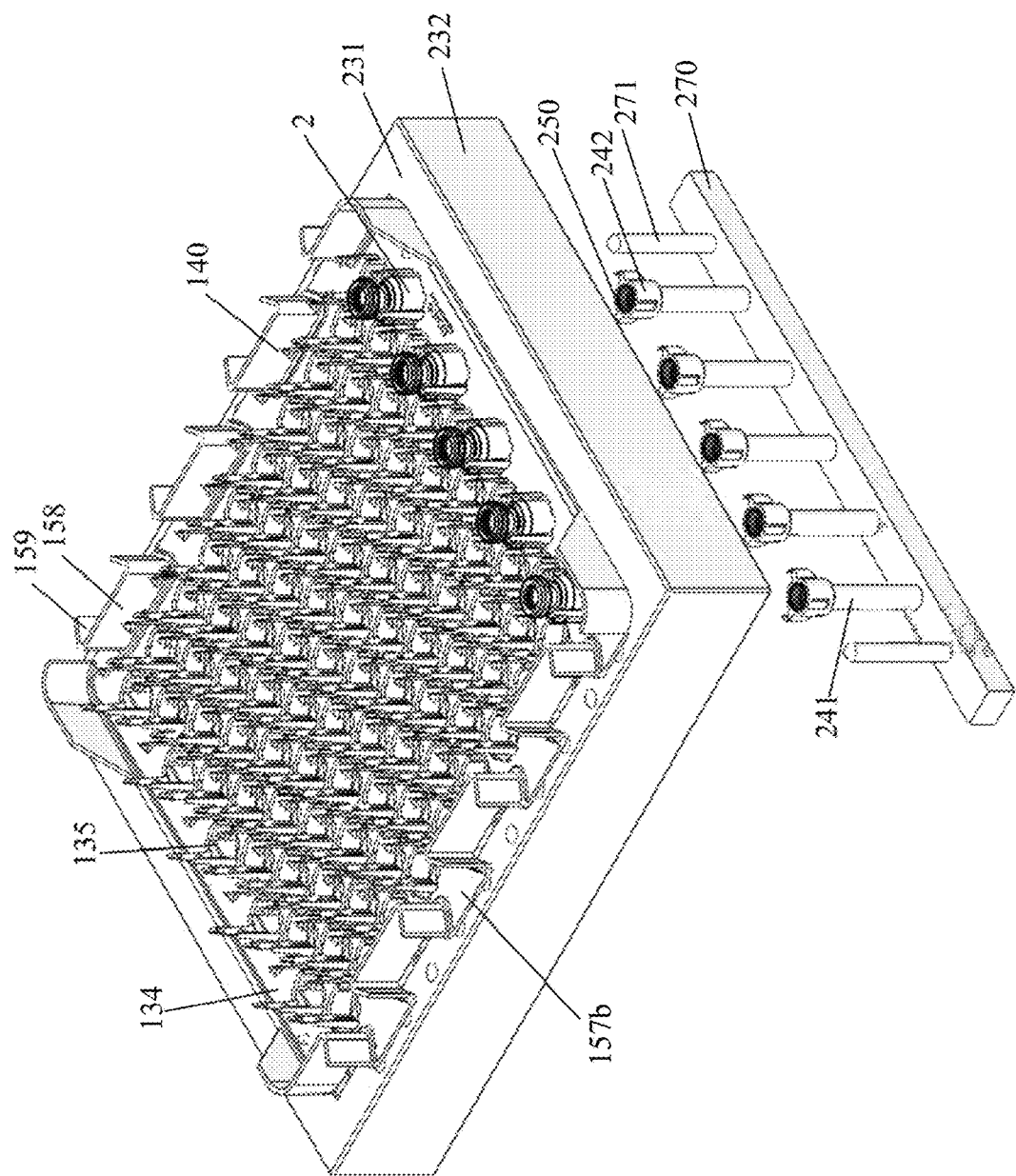
Figure 5C:
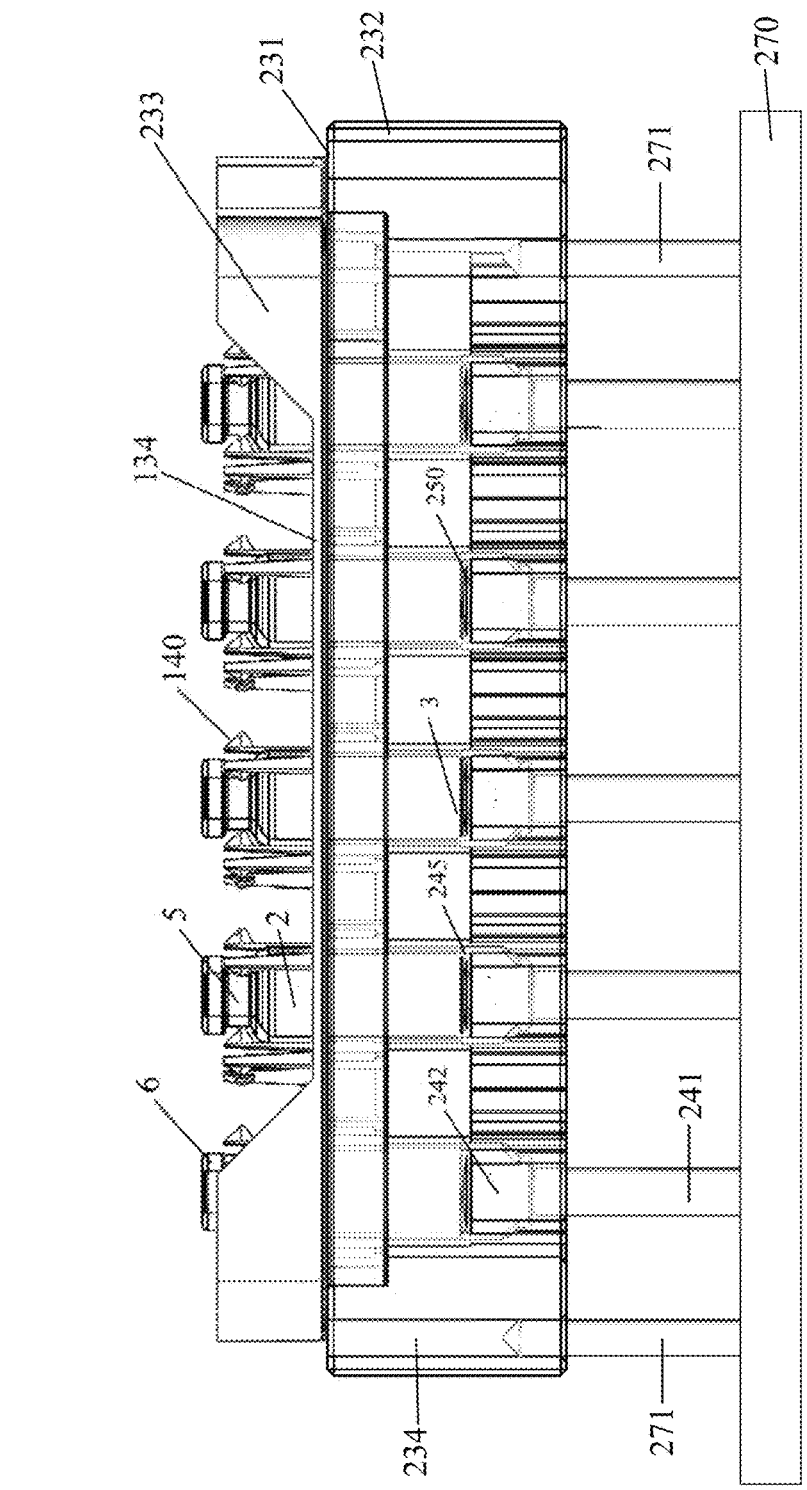

FIGS. 4b to 4g show the sequence of process steps described above for transferring the vials in the processing station of FIG. 4 from a lowered initial position (FIG. 4b) to a raised position (FIG. 5h), and vice versa. FIGS. 4b to 4g are based on a vertical displacement device 270 which comprises a plurality of push rods 241, as described above, which are arranged in correspondence to the regular arrangement of the vials 2 in the holding structure. According to FIG. 4b a total of five push rods are disposed at equidistant spacing to each other and extending in parallel with a longitudinal side of the holding structure, in association with the five vials 2 supported in the holding structure. Thus, the vials 2 supported by the holding structure can be displaced row-wise by simultaneously raising all push rods.

First, the vials are gripped above the supporting plate and held there by a gripper, such as for example shown in FIG. 2k or 2l. Or the vials are plugged or inserted loosely into the apertures of the supporting plate, as shown in FIG. 4b. The push rods 240 now drive up vertically from the bottom, as shown in FIGS. 4c and 4d (without side wall 232) and in the greatly enlarged illustration according to FIG. 4e. Here, the holding arms 245 of the push rod 240 in cooperation with the recesses 265 of an apertured plate 260 (see FIG. 8a), as described below, can ensure a centering of the bottoms of the vials 2 on the push rods 240. Subsequently, the push rods 240 are moved further vertically upward in order to raise the vials 2 in vertical direction. Starting from the position according to FIG. 4c, in which the vials 2 are held by the resilient holding arms 140 below the upper rim 6, as described above, the resilient holding arms 140 are spread apart or pivoted away laterally and then slide along the side wall of the vials 2 while pushing-up the vials 2. As described above, for the treatment or processing in a processing station the vials 2 may be raised entirely beyond the holding arms 140, but may in principle be still in engagement with these.

Applying a negative pressure to the suction caps of the push rods causes the suction of the associated vials 2 toward the push rod 240 after the treatment or processing of the vials 2. By pulling down the push rods 240, the holding force or restoring force exerted by the holding arms 140 can be overcome and the vials 2 can thus be transferred again to the lowered holding position in the holding plate. By suitable design of the corrugations of the suction cap (see FIG. 7b) and an appropriate choice of the materials, a breaking of the contact between the suction cap and bottom of the vial can be effectively prevented. Thus, during the lowering of the push rod it acts as a resilient sucker. The gripper (see FIGS. 2k and 2l) can now be removed; the vials may be moved downward into the holding structure (nest) and may be held there again by the holding devices on the holding structure, as described above.

FIGS. 5a to 5e show a corresponding sequence of process steps for a further embodiment in which additionally a plurality of cylindrical positioning pins 271 is provided on the vertical displacement device 270, which, in cooperation with a correspondingly formed positioning sleeve 234 in the side wall 232 of the processing station 230 or of holding structure 134, ensure an accurate positioning of the vertical displacement device 270 relative to the holding structure 134. In the raised position of the push rod 240 according to FIG. 5d, the front ends of the positioning pins 271 come into abutment with the carrier 134, whereby a further raising of the push rods 240 may also be prevented at the same time.

Figure 5D:
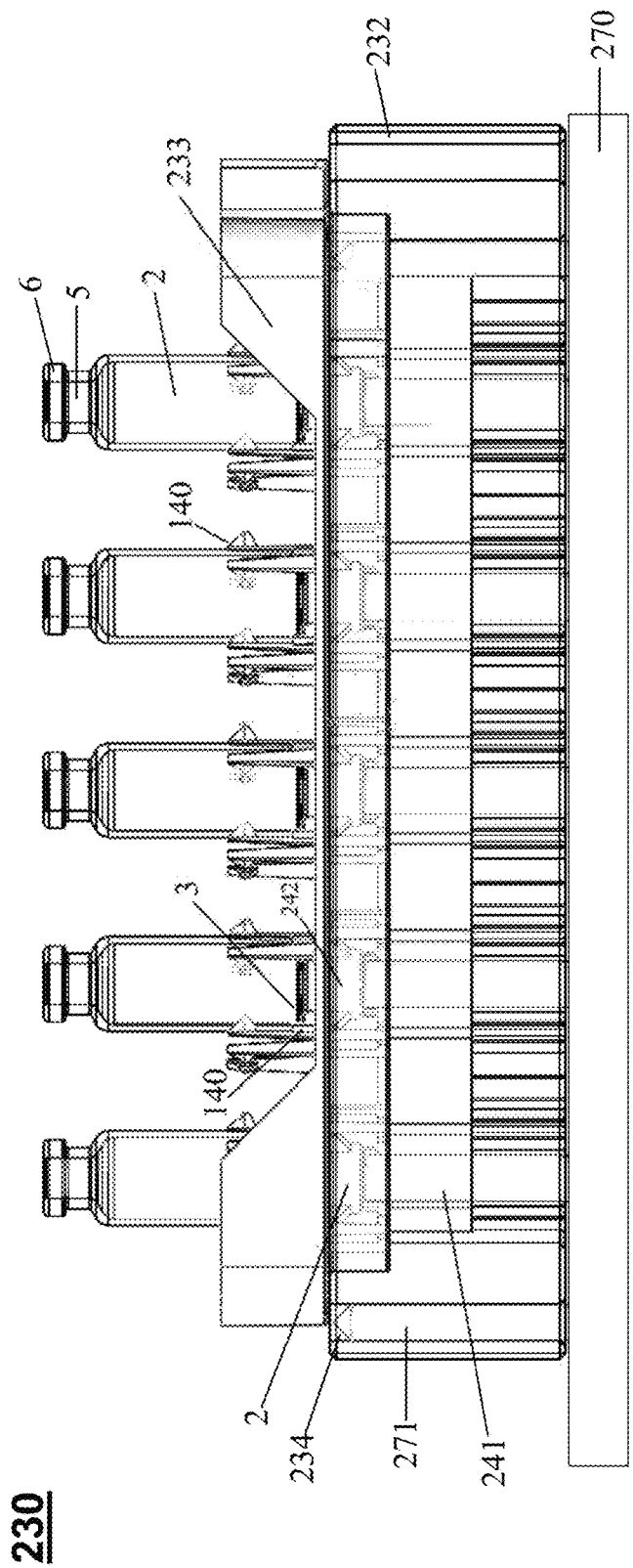
Figure 5E:
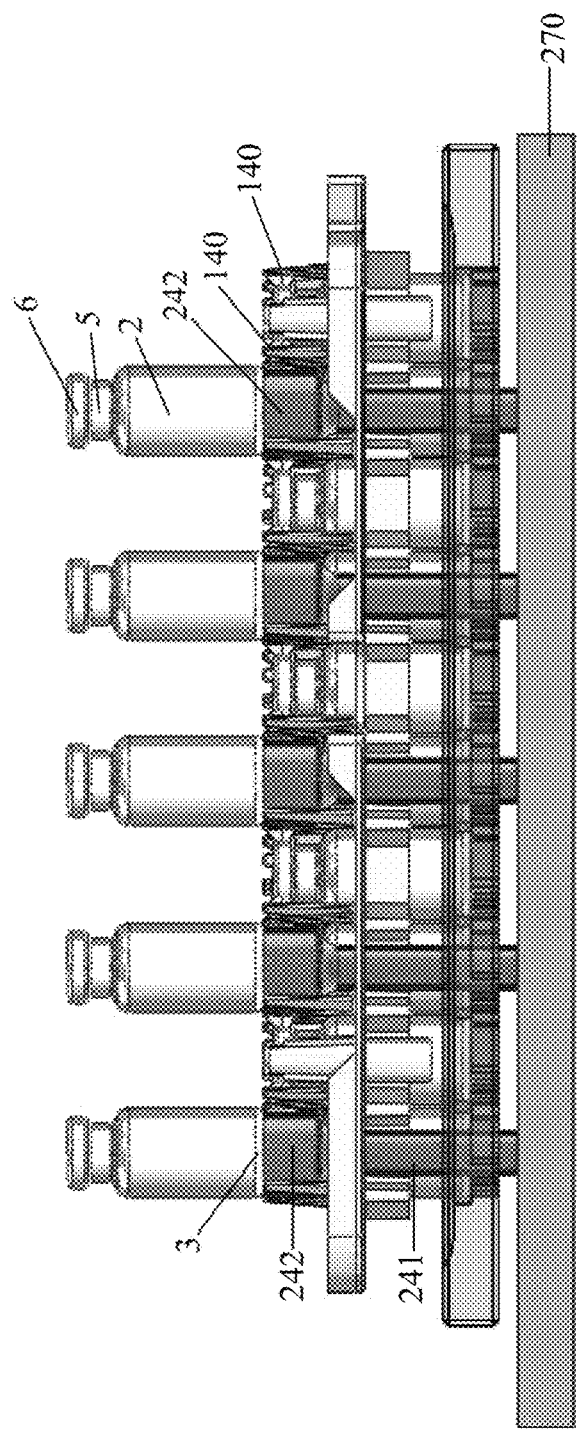
Figure 5F:
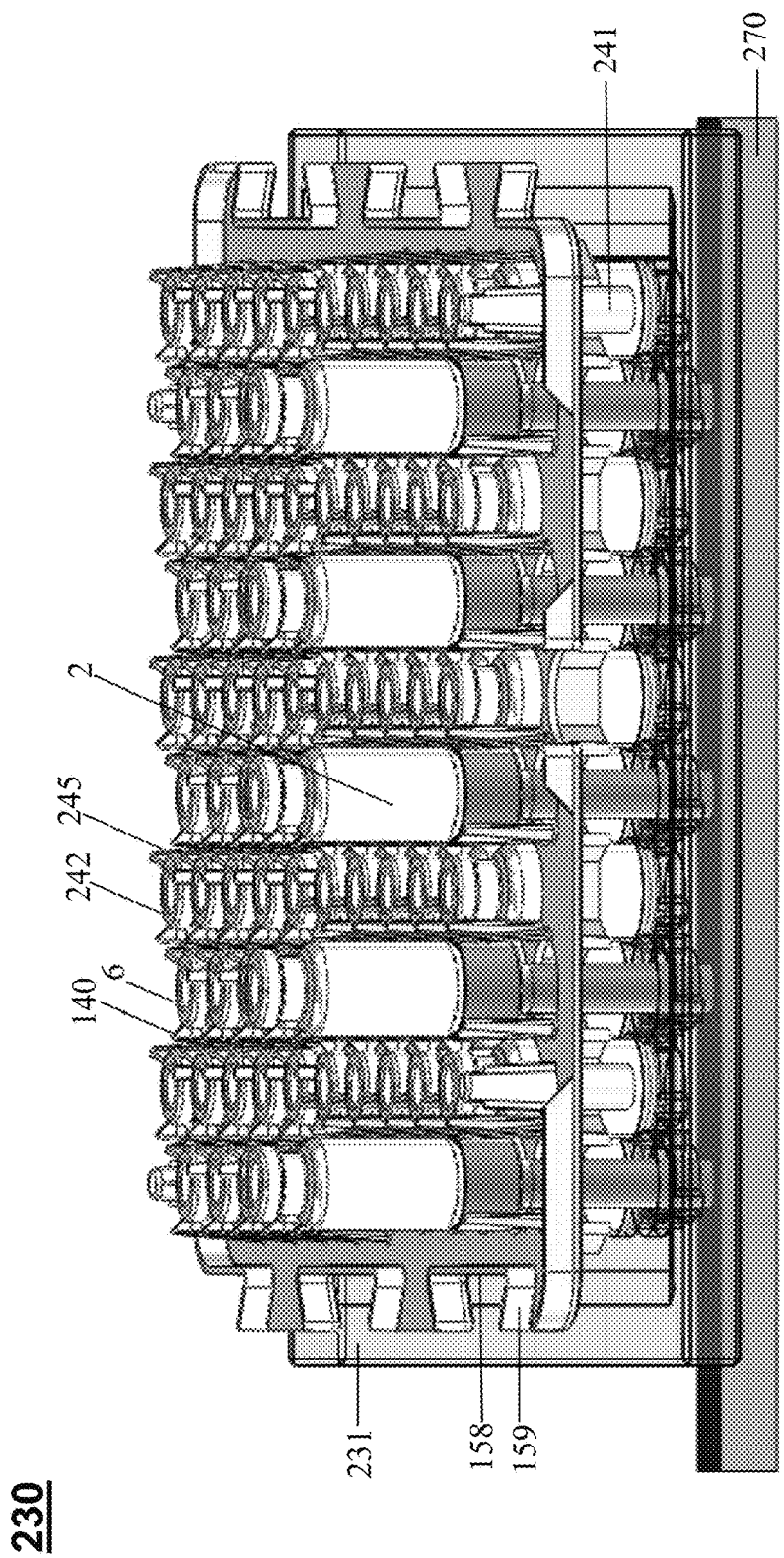
FIG. 5f shows a perspective view of the fourth step of FIG. 5e.

FIG. 5e shows the processing station 230 in the position according to FIG. 5d, but without a view onto side walls obscuring the vials and push rods. Finally, FIG. 5f shows the processing station in a position of the vertical displacement device 270, in which the engagement of all the containers 2 with the holding arms 140 of the holding structure is released completely. Here, in FIG. 5f every second row of vials 2 is not shown in order to enable a view onto the upper ends of the push rods 241 with the holding ring 242 and the holding arms 245 in the raised position of the push rods 241.

For lifting the vials it is not necessary to apply a negative pressure to the suction caps of the push rods. When in fully extended position (topmost position) of the push rods, however, a further securing of the vials may be accomplished by a negative pressure.

For positioning the push rods 240 exactly in accordance with the arrangement of the vials in the holding plate, an apertured plate 260, which is shown in FIG. 8*a*, may be provided. In the apertured plate 260 one hole for each vial 263 is provided with an annular support 266 that is formed by a plurality of curved holding members 264 that are disposed in the hole 263 spaced apart from each other at equidistant angular spacings and that are interrupted by recesses 265 through which the respective holding arms 245 of the push rods 240 can be guided upwards. This apertured plate 260 may be suitably disposed below the holding structure with the vials held by the latter and may guide the push rods and the holding arms during the raising in such a way that the holding arms precisely embrace the bottom edges of the vials.

According to a further embodiment, the apertured plate 260, as shown in FIG. 8*a*, may also be used as a holding structure for holding the vials (not shown), in which case the bottoms of the vials are accommodated in the circular recesses 265 and rest directly on the curved holding members 264 to be supported on the apertured plate.

Figure 9A:
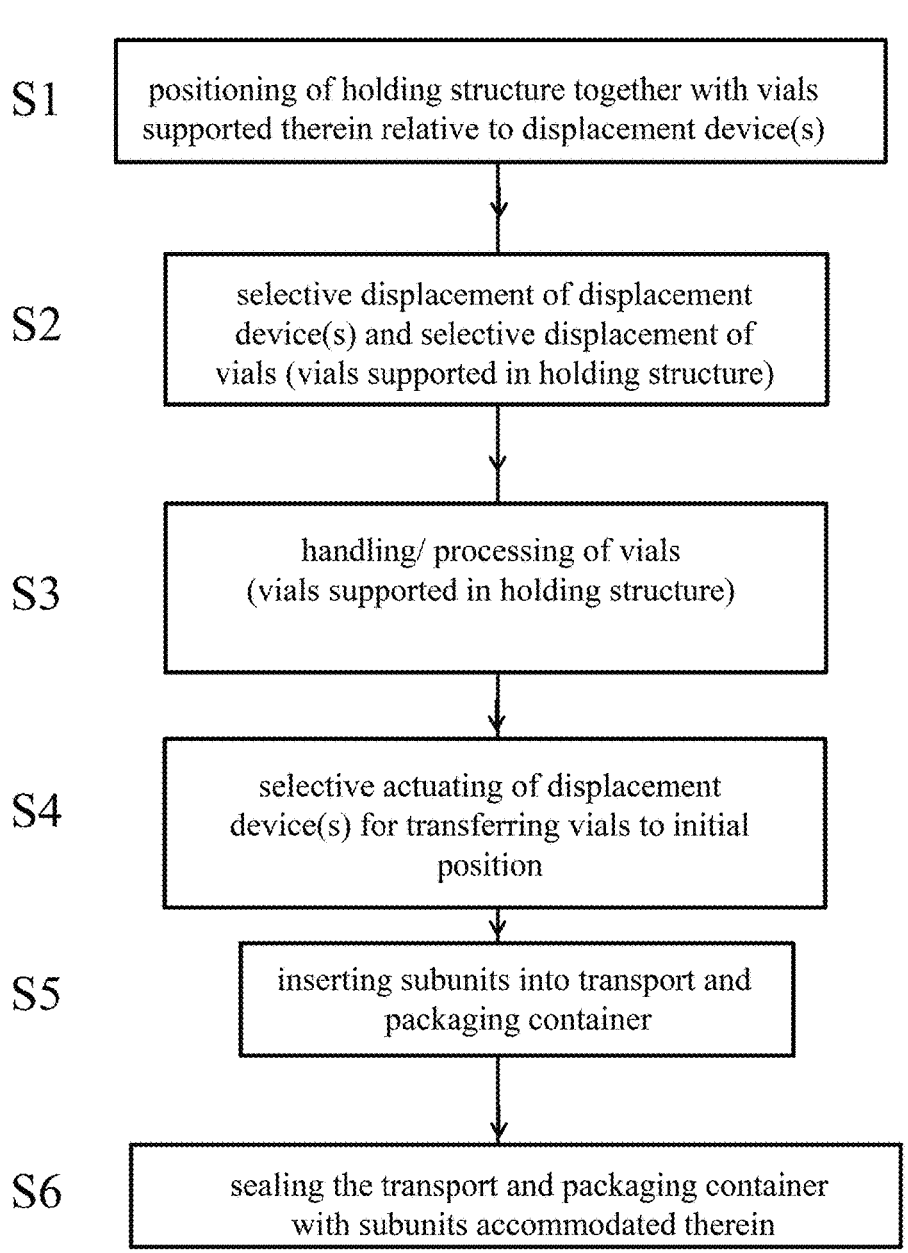

The schematic flow diagram of FIG. 9*a* summarizes the steps for the processing or treatment of vials by means of a processing station according to FIG. 4*a*.

Thus, the respective holding structure together with the containers held thereon, in particular vials, ampoules, cartridges or syringe bodies, are suitably positioned relative to the vertical displacement device in process step S1. This positioning can already take place when the holding structure is still accommodated in the transport and packaging container, as exemplified in FIG. 2*a*. In such a case, the holding structure 134 may be gripped and fixed via the access openings 29 (see plan view according to FIG. 2*b*), e.g. by means of a gripper or the like, and then the transport and packaging container 1 may be pulled downward. Subsequently, the vertical displacement device may raise the containers row-wise to the raised position (process step S2), e.g. as shown in FIG. 4*a*, in which the containers are then treated or processed further (process step S3).

This treatment or processing may involve any kind of process steps. Examples include: filling the containers with a substance or solution containing a substance; sterilization or heat treatment of the containers; a washing process; a heat treatment or other treatment of the contents of the containers, for example irradiation; sealing of the containers, for example with a plug; applying a metal lid on a closure at the upper rim of the containers, for example by beading or crimping a metal cap; a marking or labeling of the containers; a weighing of the containers. This treatment or processing of the containers in the raised position in the process step S3 may take place when the containers are completely released from the holding devices of the holding structure, but may in principle also be carried out, while the containers continue to be accommodated in the apertures or receptacles of the holding structure or are at least guided or fixed in their position.

Subsequently, a vertical displacement device, which may be identical to the vertical displacement device used previously but which may also be a different vertical displacement device, is operated in the process step S4 in order to transfer the containers to their lowered initial position, thus in particular by pulling down into the apertures or receptacles of the holding structure, as described above. In the lowered initial position, the containers may be again in engagement with the holding devices of the holding structure to be held or supported by these once again, but this is not absolutely necessary.

Then, the holding structure with the containers held thereon optionally may be inserted into the transport and packaging container used previously or into another transportation and packaging container and this may be closed or sealed in the customary manner (process step S6), for example by bonding a sterile protective film, for example, a Tyvek® film.

Figure 9B:
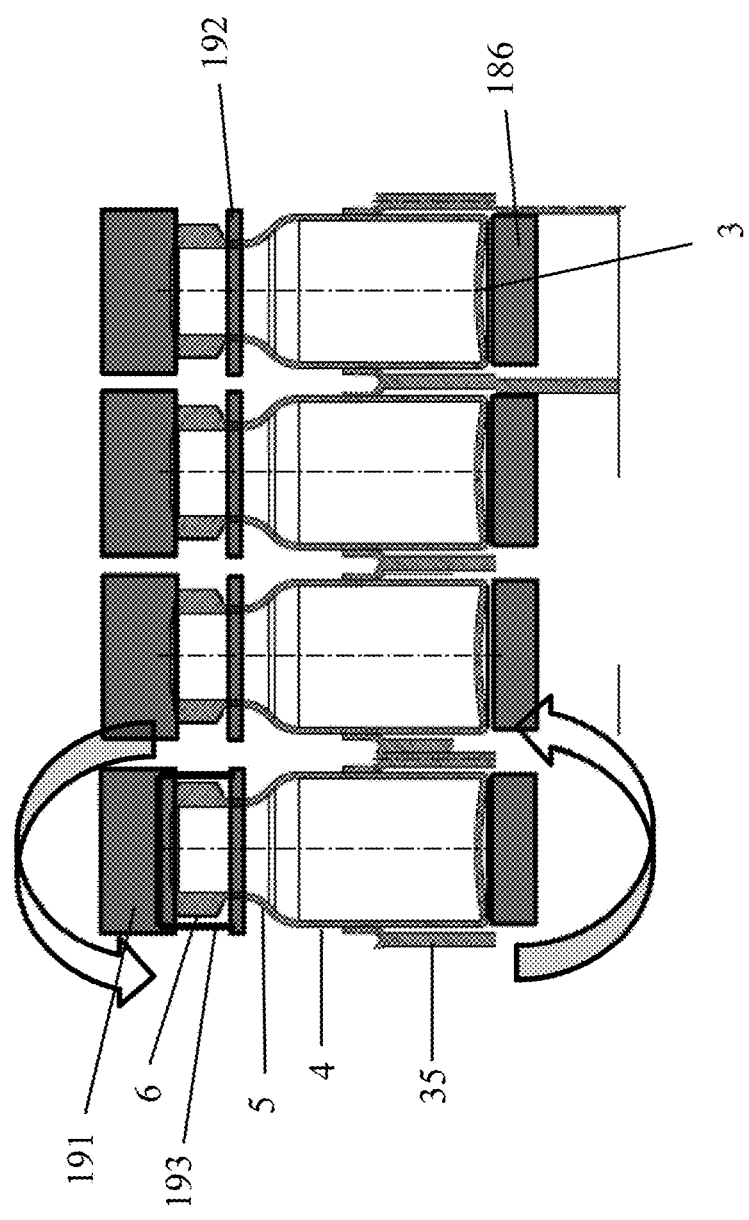
FIG. 9b is an example of the use of such a process for flanging or crimping a metal cap on an upper edge of vials.

As an example for a processing of the containers in the raised position, FIG. 9*b* shows the application of a metal lid onto the upper rims of the containers. As can be seen in the enlarged view of FIG. 9*b*, in the raised position, the upper rims of the containers 2 together with the plugs inserted therein and metal lids 193, e.g. aluminum caps, are accommodated in associated centering discs 191 in order to center the rotary movement of the containers when rotating the turntable 186. This turntable 186 may be a component of the aforementioned vertical displacement device, or may be brought into engagement with the latter only after raising the containers to the raised position. During rotation of the containers 2 a beading disk 192 mounted on the arm 190 gets in contact with the metal lid 193 and suitably crimps it by plastic deformation, so as to seal the container sterile. When all containers 2 of a carrier have been processed in the manner described above, the carrier is removed from the region of the crimping station 180 (see FIG. 9*c*) and further conveyed in the processing plant (not shown). For this purpose the containers may again be retracted into the apertures or receptacles of the carrier into their normal position and the carrier may be transferred again to the position shown in FIG. 2*b*, for example by insertion into a transport and packaging container, to be conveyed further. The processing in the crimping station thus takes place in batches, in any case without the need to remove the containers completely from the carrier.

The cap, which is placed on the upper rim of the vial, as shown in FIG. 9*b*, may also be a so-called pre-fit cap, as described below.

Figure 9D:
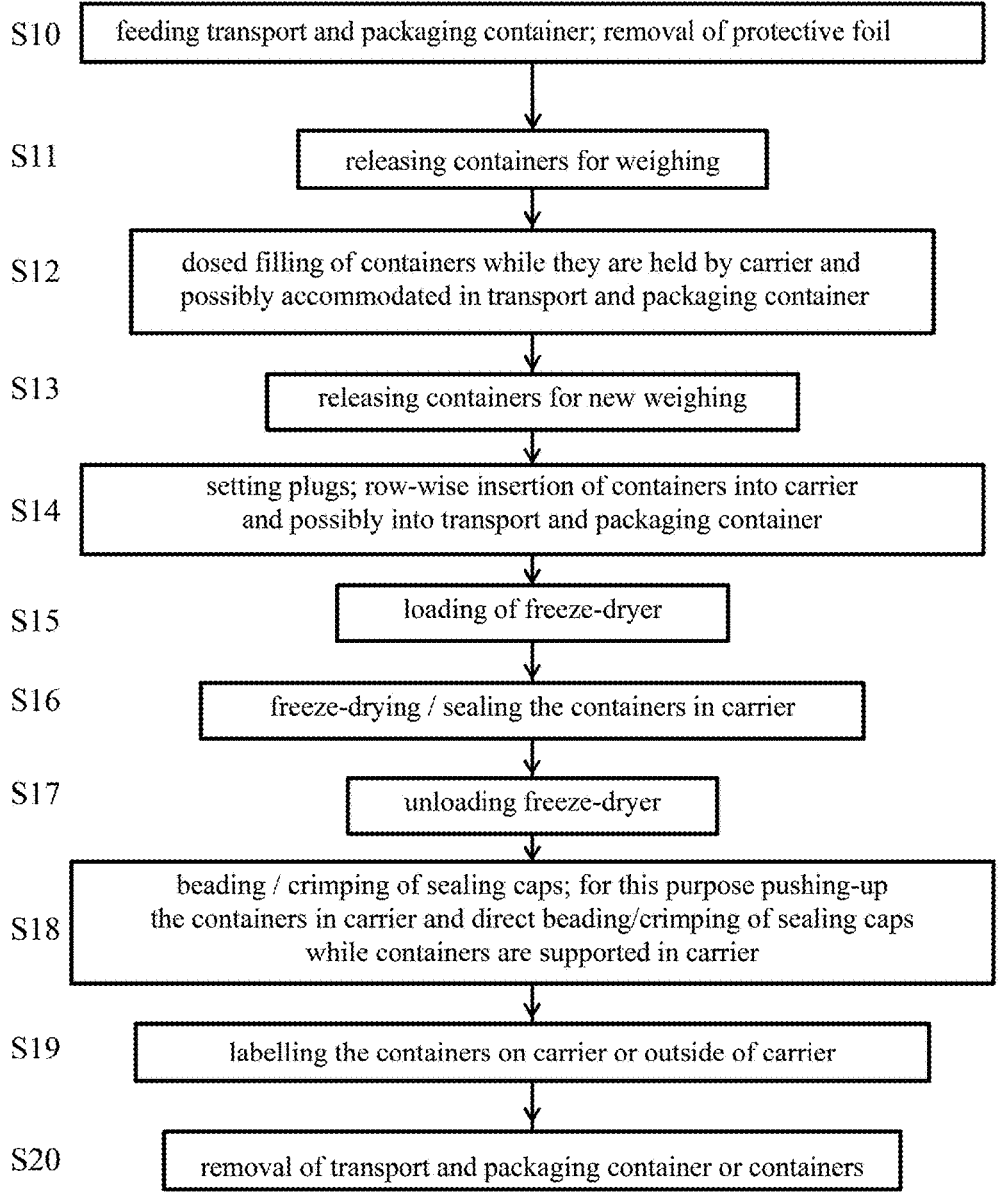
Figure 10A:
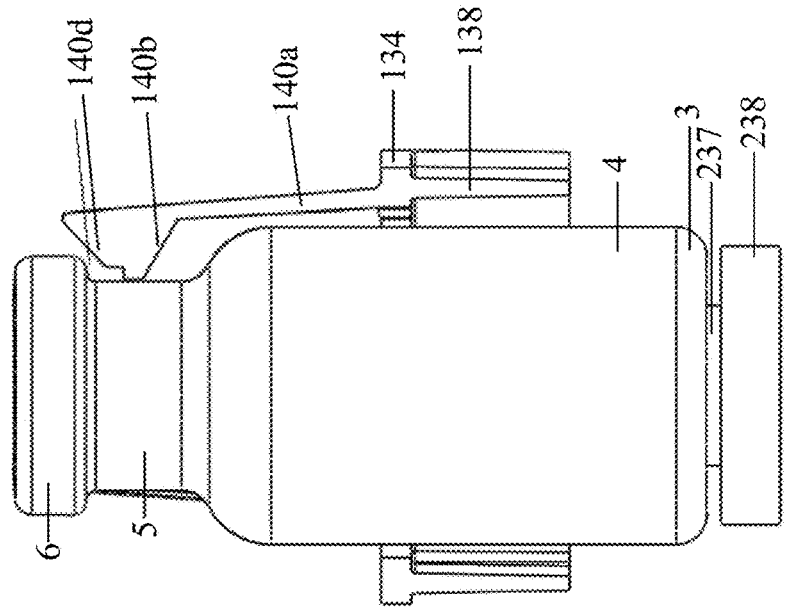
FIG. 10a shows details of an apparatus according to the present invention for weighing a container while it is being accommodated or guided in a holding structure.

As another example, FIG. 9*d* shows a schematic flow diagram of a process according to a further embodiment of the present invention. In this process, the containers are weighed before the filling (process step S11) and after the filling (process step S13), so that accurate information on the amount filled-in is obtained, which can be associated to the individual containers and traced back, e.g. by means of a software or by inscription or marking. For weighing of the containers, a weighing cell may be used, of which an example is illustrated in FIGS. 10*a* and 10*b*.

The weighing cell includes a supporting surface 238 and a weight sensor 237 provided thereon. The weighing cell is positioned underneath the containers in process steps S11 and S13, so that the weight sensor 237 can measure the weight of the respectively associated container. In general, this supporting surface 238 may be identical with the supporting surface 246 at the upper end of the vertical displacement device (see FIG. 7*a*) and the weight sensor 237 may also be integrated into the supporting surface 246 of the vertical displacement device, i.e. the weighing cell may be integrated into the vertical displacement device. Alternatively, the weighing cell may also be displaced as a separate measuring unit underneath the containers at an appropriate time in order to measure them.

Figure 10B:
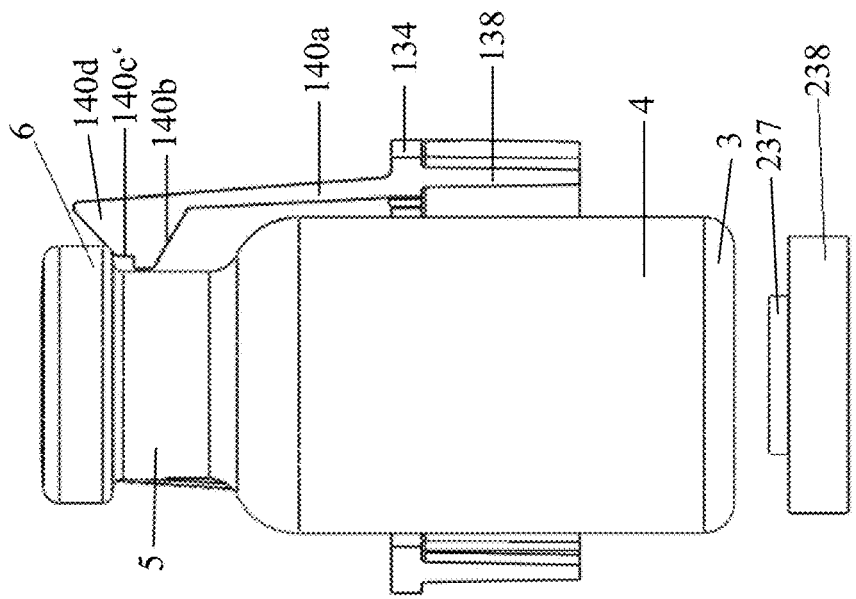
FIG. 10b shows details of the apparatus of FIG. 10a with the container accommodated in the holding structure.

As shown in FIG. 10b, in principle the weighing of the containers may be performed while the containers are accommodated in the apertures or receptacles of the holding structure, namely when they are supported by the holding arms 140a with radial and axial clearance or with radial clearance and axially freely displaceable, as described above with reference to FIGS. 2a to 2p, and the containers thus rest only loosely on the holding arms 140, but are not clamped in any way by the holding arms, as this would distort the results of the weight measurement. Of course, the weighing in the process steps S11 and S13 may also be carried out when the containers are removed completely from the apertures or receptacles of the holding structure.

From FIGS. 2c and 2k it can be seen that in most embodiments of a holding structure according to the present invention the bottoms of the containers are freely and completely accessible from the underside of the holding structure. This enables a direct contact between the bottoms of the containers with a cooling surface or with a cooling finger of a freeze-dryer to carry out a freeze-drying on the containers in process step S16. For this purpose, unlike the prior art, no time-consuming removal of the containers from the holding structure and no separation of the containers is required. Rather, the freeze-drying may be performed while the containers are supported on the holding structure.

FIGS. 9e, 9f and 9g to 9k illustrate a further example of the use of such a process according to the present invention for sealing vials by means of sterile closing caps which are pushed directly onto the upper rims of the vials. While the vials 2 can be filled via the cap 198 already put onto the upper rim of the vial 2 in a raised position of the cap 198, namely as shown for the vial 2 on the right-hand side in FIG. 9e, or can at least be processed or handled, for example, by freeze-drying, because the internal volume of the vials 2 communicates with the environment, the vials 2 are sealed sterile after pushing down the caps 198, namely as shown for the vial 2 on the left-hand side in FIG. 9e, without the need for an additional beading or crimping of a metal lid. For this purpose, in particular so-called pre-fit caps are suitable. The enlarged partial view in FIG. 9f shows the supporting of the vial 2 on the resilient holding tabs 140a of the carrier. As shown here, in the raised position the bottom edge of the cap 198 is supported with radial clearance on the bottom rim of the holding receptacle 140e, i.e. it rests loosely on the resilient holding tab 140a. In this position, the weight of the vial 2 can be measured, for example by means of a weighing cell, as described with reference to FIGS. 10a and 10b.

As can be seen from the illustration of the supporting of the left vial 2 in FIG. 9e, the bottom edge of the cap 198 is still supported with radial clearance on the bottom rim of the holding receptacle 140e in the pushed-down position of the cap 198. Even in this position the weight of the vial 2 can be measured, for example by means of a weighing cell, as described with reference to FIGS. 10a and 10b.

For sterile closure of the vials 2, it is therefore important that the caps 198 and vials 2 can be displaced relative to each other in axial direction. According to the invention, this axial displacement can be performed while the vials 2 are supported on a carrier ("nest") or are at least accommodated and guided in the apertures or the receptacles. Furthermore, according to the invention also a weighing of the vials 2 may be carried out while they are supported on the carrier.

FIGS. 9g to 9k summarize five consecutive process steps for sealing the vials according to a further variant of the process of FIG. 9d. First, the vials 2 are filled in a first process step shown in FIG. 9g. while they are supported on the carrier 134. After the filling, the caps 198 are pressed onto the upper rim of the vials 2 in a second process step shown in FIG. 9h. In this raised position of the caps 198 a freeze-drying of the contents of the vials 2, or also any other handling or processing of the vials 2, may be performed. By way of example, this is indicated in a third process step shown in FIG. 9i by reference numeral 225, which is to indicate the cooling trays of a freeze-dryer, not shown in more detail. In a fourth process step shown in FIG. 9j, the cooling trays 225, or other supporting surfaces on which the bottoms of the vials 2 are directly supported, are pressed against each other, as indicated by the arrows. As a result, the caps 198 are pressed down onto the vials 2 and these are thus sealed sterile. The aforementioned process steps may be carried out while the vials 2 are supported on a carrier ("nest") or at least accommodated and guided in the apertures or receptacles thereof. Subsequently, in fifth process step shown in FIG. 9k the carrier 134 together with the vials 2 supported thereon is removed from the processing station.

Figure 11A:
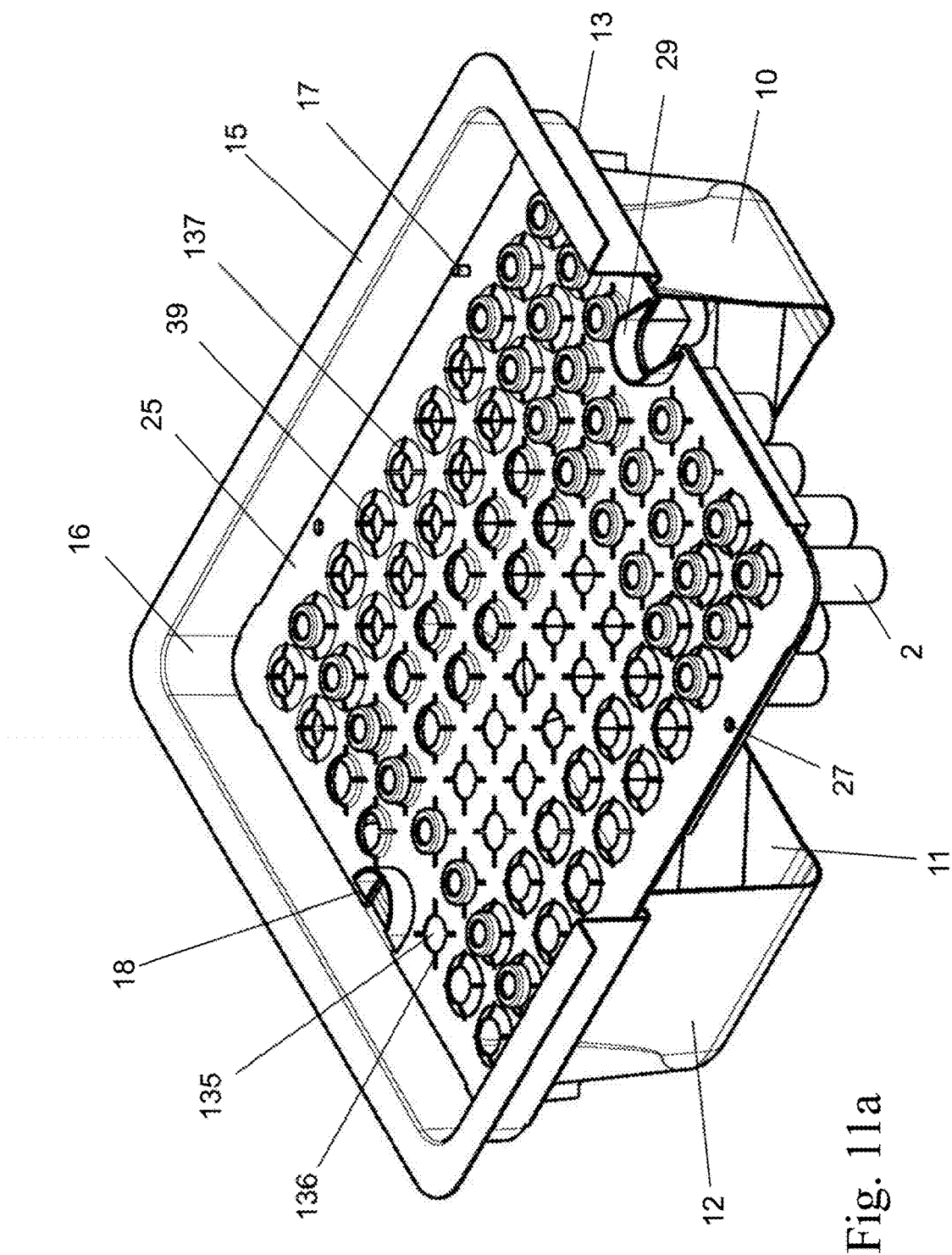
FIG. 11a shows a further variant of a holding structure for use in a process according to the present invention.
Figures 11B, 11C:
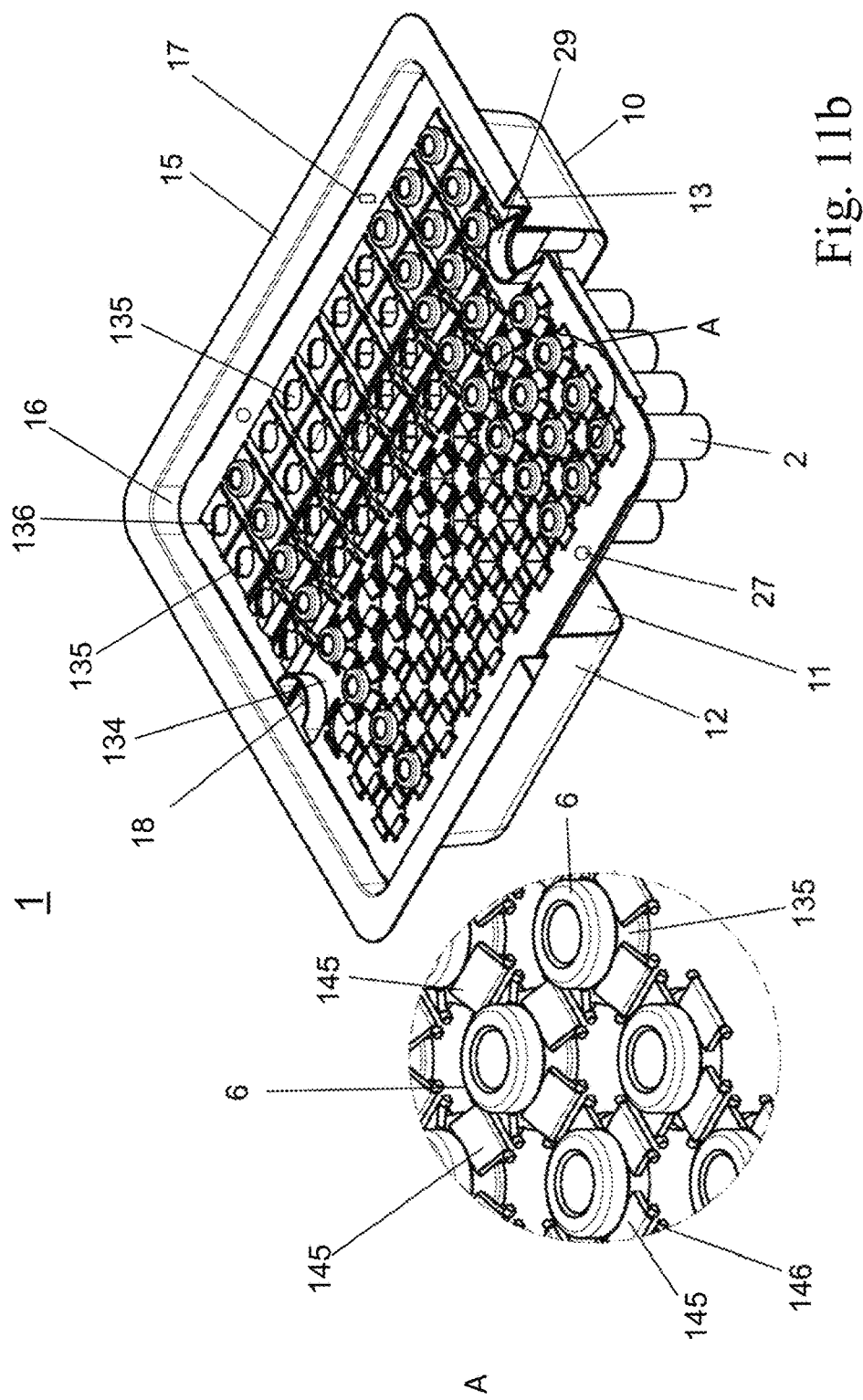
FIG. 11b shows another further variants of a holding structure for use in a process according to the present invention.
FIG. 11c shows a magnified view of circle A of FIG. 11b.

FIGS. 11a and 11b show two further examples of holding structures which can be generally used in a process according to the present invention.

According to FIG. 11a, a planar transport plate 25 is used for concurrently holding a plurality of containers, which is formed of a plastic, for example punched out or by injection-molding, and which has a plurality of apertures 39 for accommodating the vials 2. The apertures 39 are formed in annular positive-fit members 137 which act as flaps that are either inserted into the apertures 39, particularly latched or clipped into its peripheral edge, or which are formed integrally with the planar carrier 25, for example by a 1-component (1K) or 2-component (2K) plastic injection molding process. The containers 2 may be inserted into the apertures 39 of the positive-fit members 137 from above or from below. This allows a plurality of containers 2 to be fixed positively in the region of their constricted neck portions 5.

FIG. 11b shows a further embodiment of a holding structure in which the fixing of the containers 2 is implemented by means of pivotable holding tabs or flaps 145, which are pivotally mounted on the planar carrier 134. At their lower ends, the holding tabs 145 have pins 146 respectively projecting laterally, which are clipped or pressed into a correspondingly formed receptacle of the carrier 134. Thus, the holding tabs or flaps 145 can be pivoted between a first position, in which the apertures 135 of the carrier are released and the containers can be freely inserted, and a second position, in which the containers are secured in a positive-fit manner. The force required to pivot the flaps or holding tabs 145 particularly may be defined suitably by the mounting of the pins 146 in the receptacles provided for this purpose. It may also be provided that the holding tabs 145 are resiliently biased toward the second position. In such a holding structure, the containers 2 can be introduced easily into the apertures 135 from underneath the carrier 134, until the upper rims 6 of the containers 2 respectively rest on holding tabs 145 associated with a respective aperture 135. In general, however, the containers 2 may be inserted into the apertures 135 also from above the carrier 134, without the risk of intrusion of impurities into the containers via their filling openings. For this purpose, e.g. the vertical displacement device may be configured such that the holding tabs 145 are jointly spread to such an extent, for example in a raised position of the vertical displacement device, that the containers 2 are inserted into the apertures 135 from above, e.g. to be respectively supported on a supporting surface at the upper end of the vertical displacement device. When lowering the vertical displacement device, the spreading of the holding tabs 145 may then be released.

Referring to FIGS. 12a to 13c, further embodiments of a vertical displacement device and of the interaction of such a vertical displacement device with holding devices on a holding structure will be described hereinafter, as they can be used in a process according to the present invention.

Figure 12A:
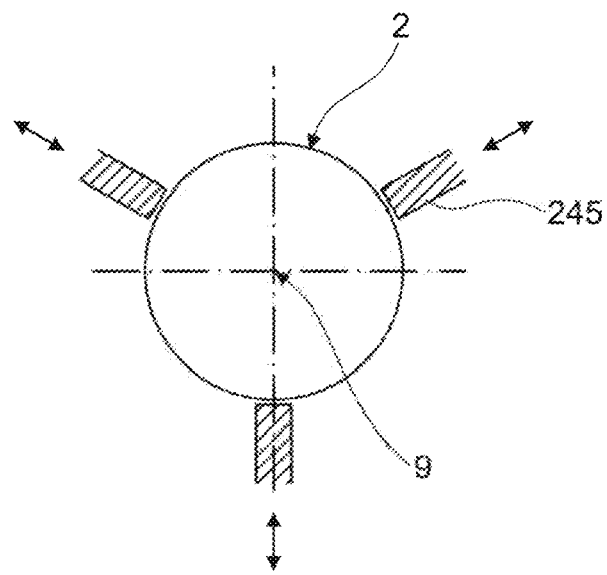
FIG. 12a shows a further variant of a vertical displacement device for use in a process according to the present invention illustrating radial movement of the arms.

FIG. 12a shows a container 2 in a plan view, of which the bottom edge is gripped by the holding arms 245 of a vertical displacement device not shown in more detail, as described above with reference to FIG. 6a, in order to grip the container 2 and to fix it on the vertical displacement device. For releasing the containers, the holding arms 245 may be displaced radially outward, as indicated by the double arrows. This displacement can be performed actively, for example driven electrically, magnetically, pneumatically or mechanically, for which purpose a suitable drive may be provided at the upper end of the vertical displacement device. Or the holding arms are resiliently biased radially inward or outward and are released or pushed together or apart when a predetermined height of the vertical displacement device is reached. For this purpose, a control cam or the like may cooperate with the vertical displacement device. In order to grip the containers reliably, attention has to be paid to a common and coordinated displacement of the holding arms 245, wherein the displacement needs to be centered to the center 9 of the container bottom. After spreading apart of the holding arms 245, the container 2 is released by the vertical displacement device and can then be transferred to a holding device or to a processing station.

Figure 12B:
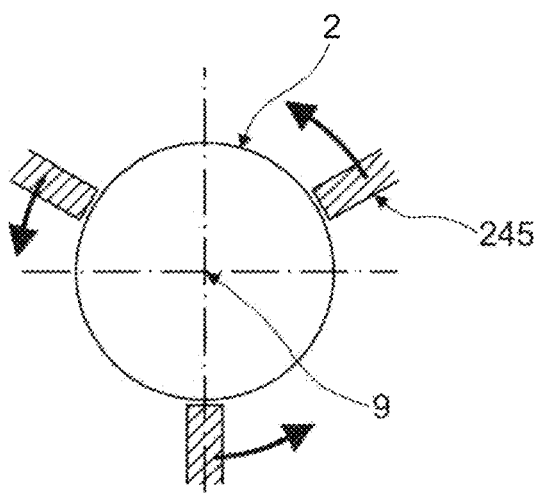
FIG. 12b shows a further variant of a vertical displacement device for use in a process according to the present invention illustrating circumferential movement of the arms.

FIG. 12b shows a further embodiment in which this displacement of the holding arms 245 is not effected radially, but both radially inward or outward and together with a movement component in the circumferential direction of the container, as indicated by the three curved arrows.

Figure 12D:
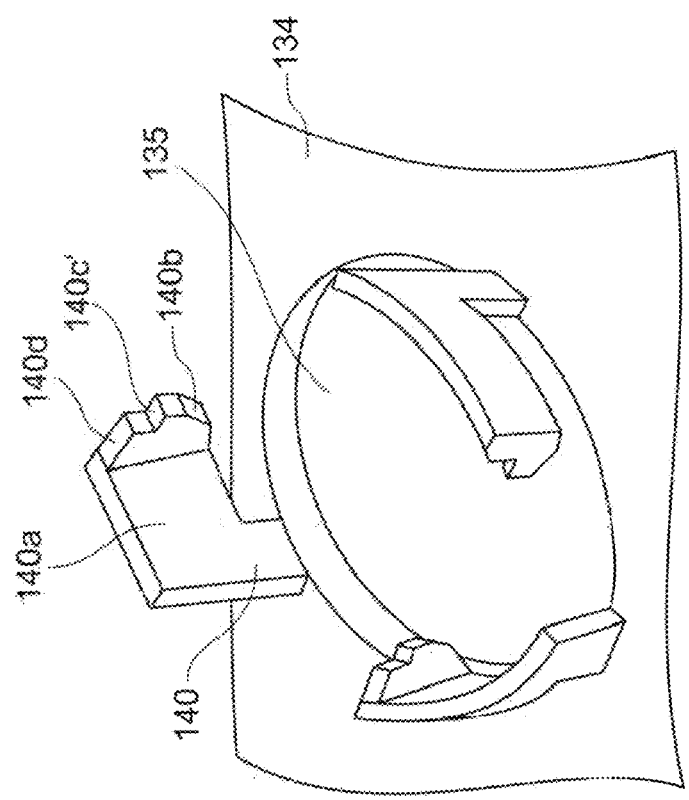
FIG. 12d shows a perspective view of the further variant of FIG. 12c.
Figure 12C:
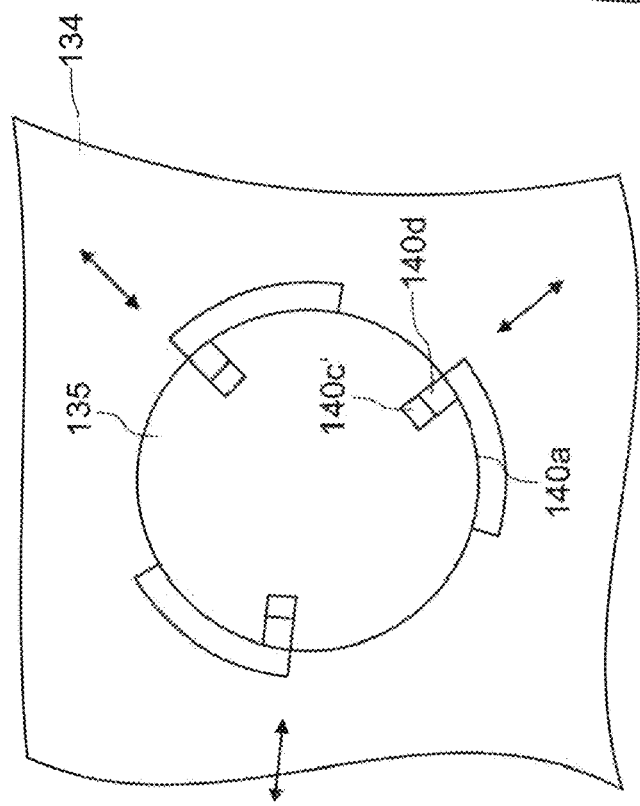
FIG. 12c shows a top view of a further variant of a vertical displacement device for use in a process according to the present invention illustrating resilient movement of the arms.
Figure 12G:
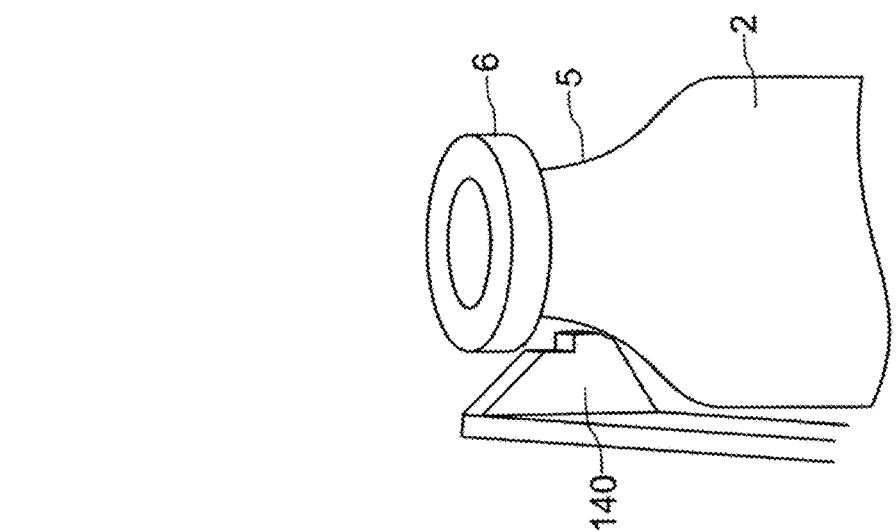
FIG. 12g shows a third step of installation of the further variant of FIG. 12c.
Figure 12F:
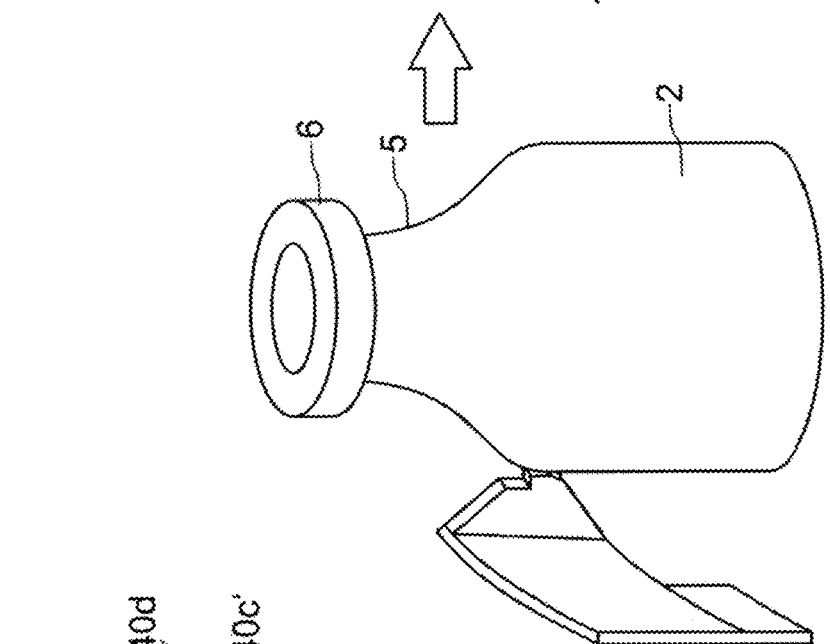
FIG. 12f shows a second step of installation of the further variant of FIG. 12c.
Figure 12E:
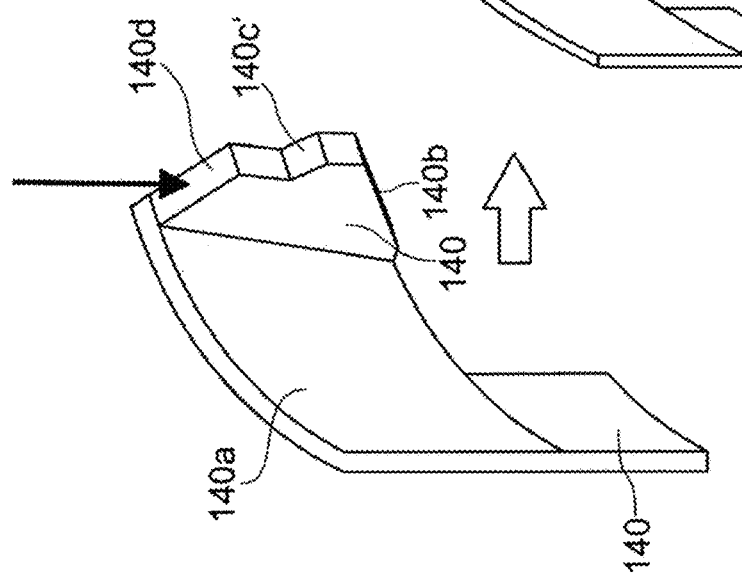
FIG. 12e shows a first step of installation of the further variant of FIG. 12c.

FIGS. 12c and 12d show a further variant of a holding structure 134, in which a comparable spreading of the resilient holding arms 140 is implemented at the holding structure 134 rather than at the vertical displacement device for releasing and holding the containers. According to the plan view of FIG. 12c, three resilient holding arms 140a are disposed around the aperture 135 in the planar carrier 134, similar to the holding arm described above with reference to FIG. 2m. According to FIG. 12d, the base of the holding arm 140 is formed to be relatively narrow, whereas that portion that is actually used for the supporting of the containers is formed at a rectangular, relatively large portion 140a, including the upper and lower slanted insertion surfaces 140d, 140b and the step-shaped holding nose 140c' on which the upper rim of the container (not shown) rests loosely or at least with a radial clearance. Upon insertion of the container into the aperture 135, the upper slanted insertion surface 140d and the holding nose 140c' get in abutment with the sidewall of the container, wherein in this case the holding arm is not bent backward, i.e. radially outward, but swiveled open in a rotary movement in order to let the container pass through. If the container is finally inserted so far into the aperture that the neck portion enters the region of the holding nose 140c', the holding arm 140 swivels back to the initial position and holds the container at the neck, as described above for example with reference to FIG. 2m. This is shown in the sequence of steps of FIGS. 12e, 12f, and 12g, namely first the initial position (step 1 in FIG. 12e), then the insertion of the container 2 from above (step 2 in FIG. 12f) and then the supporting of the container 2 on the holding arm 140 (step 3 in FIG. 12g).

Figure 12H:
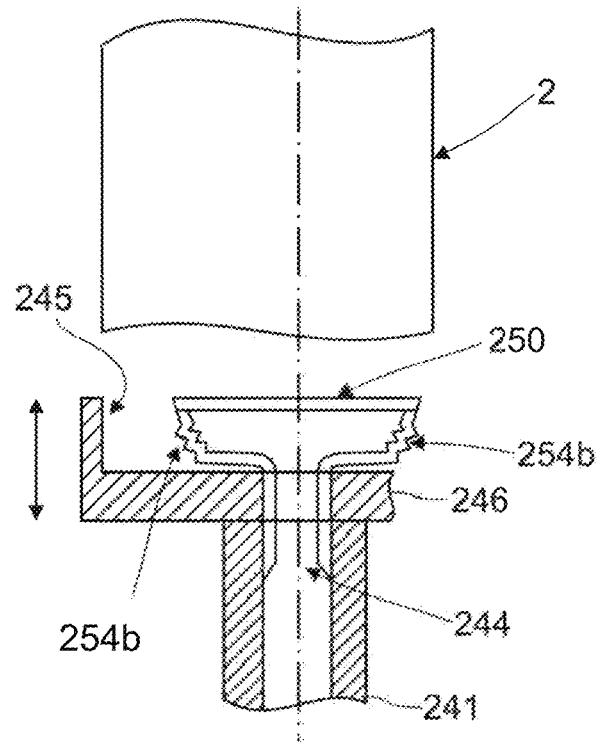
FIG. 12h shows a further variant of a vertical displacement device for use in a process according to the present invention illustrating prior to negative pressure attachment.
Figure 12I:
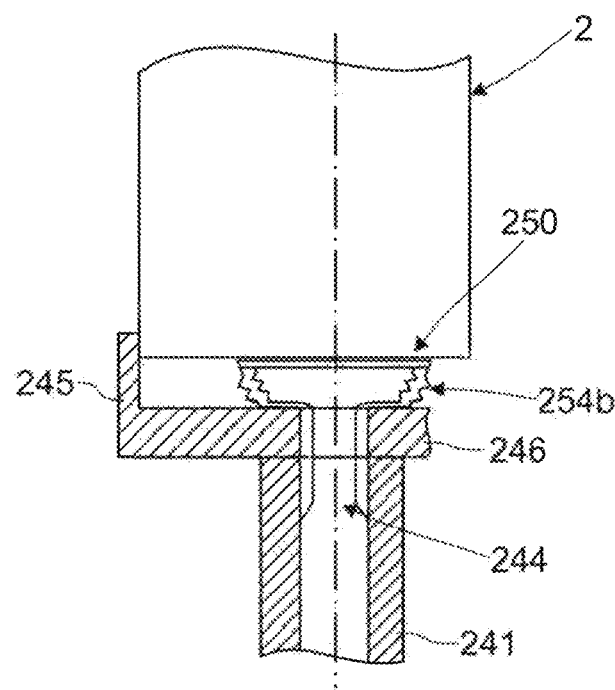
FIG. 12i shows the vertical displacement device of FIG. 12h, after negative pressure attachment.

FIGS. 12h and 12i show a further embodiment of a vertical displacement device, when the container 2 is released (FIG. 12h) and when the container 2 is pulled down toward the holding arms 245 by applying a negative pressure to the suction cap 250. In contrast to the embodiment of FIG. 7a, the suction cap 250 of a resilient plastic or rubber is clipped directly into the axial through-hole 244 of the push rod shaft 241. The upper rim of the suction cap 250 together with edge portions of the holding arms 245 directly form a supporting surface for supporting the bottom of the container 2. If the inner edge of the holding arms is inclined upwards, tolerances of the diameter of the container 2 can be compensated in a simple manner. The suction cap 250 is, on the one hand, sufficiently resilient to provide a sufficient sealing effect upon application of the negative pressure, on the other hand, it is sufficiently rigid to allow a reliable and uniform supporting of the container 2 on the push rod shaft 241.

Figure 12K:
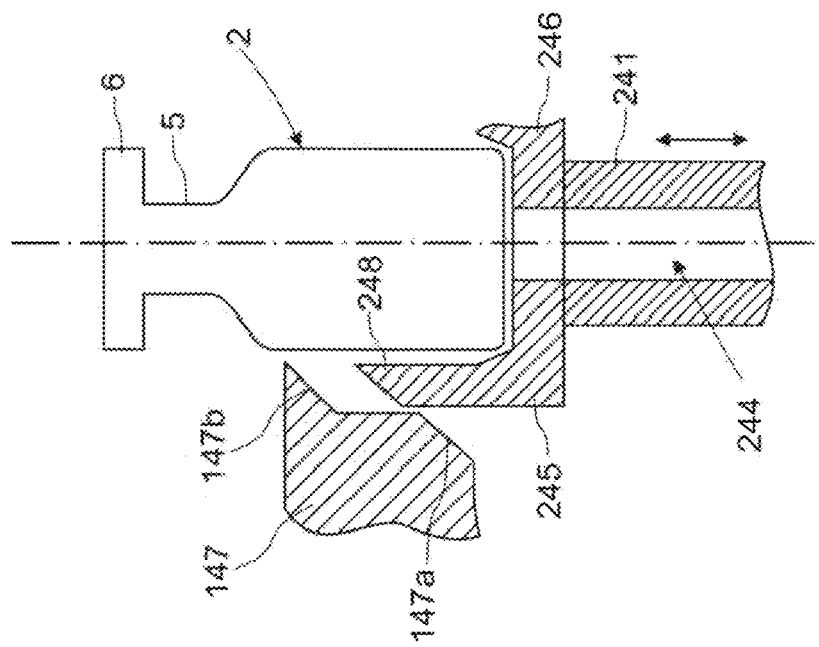
FIG. 12k shows the vertical displacement device of FIG. 12j, after disengagement.
Figure 12J:
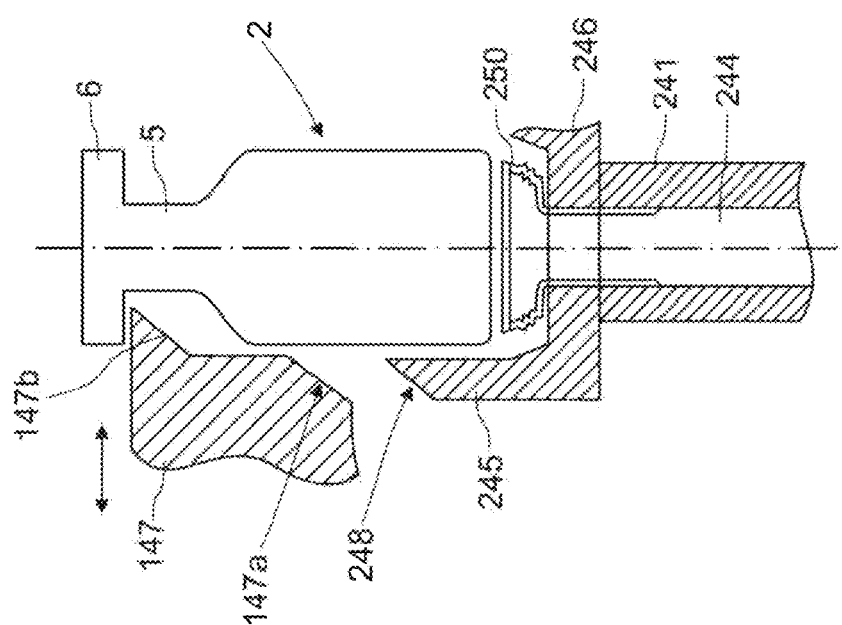
FIG. 12j shows a further variant of a vertical displacement device for use in a process according to the present invention illustrating cooperative movement between the vertical displacement device and the holding devices after engagement.

FIGS. 12j and 12k show a further embodiment, wherein the vertical displacement device cooperates with the holding devices of the holding structure in order to loosen the containers for release and to bring them again into engagement with the containers. For this purpose the holding device 147 of the holding structure not shown here can be adjusted radially inwardly and outwardly, for example, is pivotally radially, as indicated by the double arrow in FIG. 12j. At the bottom edge of the holding device a slanted surface 147a is formed, which cooperates with an opposite slanted surface 248 at the upper edge of the holding arms 245 (or is formed in another region of the vertical displacement device). For raising the vials 2 from the position shown in FIG. 12j to a raised position, the push rod 241 is first raised up and pushes the vial 2 upwards until the slanted surfaces 248 on the holding arms 245 get in contact with the slanted surfaces 147a on the bottom edges of the holding devices 147. In this position the transition region between the cylindrical side wall of the vial 2 and the constricted neck portion 5 gets in the vicinity of the projecting nose 147b of the holding devices 147. With further raising of the push rod, the slanted surfaces 147a and 248 slide against one another, which results in an outward resetting of the holding devices 147 and thus results in a complete release of the vial 2 (see FIG. 12k), which can then be lifted out further above of the holding structure. Here, the holding arms 245 of the vertical displacement device act as cams for controlling the position of the holding devices 147 of the holding structure. Obviously, a corresponding coordinated displacement of the holding devices of the holding structure can also be implemented by means of a displacement device separately provided in the region of the processing station or of the vertical displacement device.

With reference to the FIGS. 13a to 13c, a further embodiment of a vertical displacement device is described hereinafter, in which vials 2 are clamped on the bottom edge thereof for pulling them down. For this purpose, according to FIG. 13a a pressure cuff 249, inflatable by a fluid and provided with at least one pressure chamber 249a, is provided on the inside of the holding ring 242 of the push rod shaft 241, which enables an unimpeded or at least low-friction insertion of the vial into the receptacle in the holding ring 242 in its relaxed home position until the supporting surface 246 is reached. In order to grip a vial 2, a pressure is applied to the pressure chambers 249a of the pressure cuff, so that they increase in a defined manner radially inwardly, until finally the bottom edge of the vial 2 is clamped, as shown in FIG. 13b. In this position, the vial 2 is fixed on the vertical displacement device; any lateral shifting of the vial 2 is prevented. In this position, the vial 2 can be raised upward (see. FIG. 13c) or be pulled down.

As will be readily apparent to the person skilled in the art upon reading the above description, the holding structures exemplified above and procedures for the displacement of the vertical displacement device and the holding devices may as well be combined in other ways with each other as described above.

As will be readily apparent to the person skilled in the art when studying the above description, in general the aforementioned aspect of the positive-fit or frictional coupling between directly adjacent holding structures is independent of the specific design of the holding of the vials at such holding structures, so that this aspect in principle may also be claimed as an independent aspect of the present invention independently from the specific design of the holding of the vials at such holding structures.

The holding force exerted by each of the holding devices on the containers is sufficient to hold the containers reliably on the holding structure. In particular, the holding force exerted is greater than the weight of the containers, if necessary together with the content and sealing plugs. Thus, a reliable holding of the containers on the holding structure is ensured. At the same time, the containers may be displaced in the apertures or receptacles of the holding structure without too much effort, in particular these may be displaced in axial direction or rotated.

Of course, the holding structure (the carrier) in the sense of the present invention may also be formed of a thermoplastic, thermosetting or elastomeric plastic material, wherein at least portions of the holding structure or of the carrier are provided with a coating reducing friction to facilitate the insertion and removal of the containers.

As will be readily apparent to the person skilled in the art upon reading the above description, the various aspects and features of the embodiments described above may be combined in any manner with one another, resulting in numerous further embodiments and modifications. As will be readily apparent to the person skilled in the art upon reading the above description, all such further embodiments and modifications shall be comprised by the present invention, as long as these do not depart from the general solution and scope of the present invention, as defined in the appended claims.

What is claimed is:

1. A process for sealing containers that contain substances for medical, pharmaceutical or cosmetic applications, comprising
    conveying the containers, by means of a conveyor, past at least one processing station or pass it for the treatment or processing while the containers are held by a carrier in a regular arrangement,
    filling the containers with the substance while the containers are held by the carrier,
    pushing caps onto the upper rims of the containers so that the internal volumes of the containers communicate with the environment via the caps positioned on the upper rims of the containers while the containers are held by the carrier,
    subjecting the containers to a freeze-drying process while being held by the carrier by bringing the bottoms of the containers, that are freely and completely accessible from the underside of the carrier, into direct contact with a cooling surface or a cooling finger of a freeze-dryer, wherein the internal volumes of the containers communicate with the environment via the caps positioned on the upper rims of the containers, and
    displacing the caps and the containers in axial direction relative to each other after the freeze-drying process to press down the caps onto the containers while the bottoms of the containers are supported on a supporting surface for sealing the containers with the caps.

2. The process according to claim 1, wherein
    the containers are filled with the substances via the caps positioned on the upper rims of the containers.

3. The process according to claim 1, wherein the cooling surface or cooling finger is a plurality of cooling surfaces or cooling fingers that together with the containers directly supported thereon are stacked one above the other, and wherein the cooling surfaces or cooling fingers of the freeze-dryer are pressed against each other for pushing down the caps of the containers and sealing the containers with the caps.

4. The process according to claim 1, wherein
    the containers are held in openings or receptacles of the carrier in the regular arrangement,
    at least two resilient holding tabs are respectively associated with the openings of receptacles, and
    the containers are each held by the holding tabs in the region of a constricted neck portion below an expanded upper rim at a top end of the respective container with radial clearance and with axial clearance so as to be freely displaceable in axial direction.

5. The process according to claim 4, further comprising slanted insertion surfaces that are formed at upper ends of the holding tabs which are followed by holding noses projecting from the holding tabs radially inwards.

6. The process according to claim 5, wherein the containers are weighed before and after the step of filling for obtaining information on the amount filled-in, which is associated to the individual containers and traced back by a software or by inscription or marking.

7. The process according to claim 6, wherein the containers are lifted for the step of weighing vertically upwards to a raised position using a vertical displacement device and are lowered after the step of weighing to be held again by the carrier in the openings or receptacles and in the regular arrangement.

8. The process according to claim 7, wherein the containers are weighed in the raised position while being held in the openings or receptacles of the carrier by the at least two resilient holding tabs.

9. The process according to claim 7, wherein the containers are weighed in the raised position by means of a weighing device which is integrated into the vertical displacement device.

10. The process according to claim 7, wherein the vertical displacement device comprises a plurality of lifting rods that are aligned along a line and simultaneously raise a number of containers to the raised position.

11. The process according claim 10, wherein the vertical displacement device further comprises a positioning device for positioning the lifting rods relative to the carrier together with the containers held thereon.

12. The process according to claim 11, wherein
    the vertical displacement device further comprises a negative pressure generating device for retracting the containers by means of a negative pressure acting on the bottom portions of the containers, and
    the negative pressure generating device is coupled to the vertical displacement device in such a manner that the negative pressure acts on the bottom portions of the containers via supporting surfaces provided at an upper end of the vertical displacement device, on which the bottom portions of the containers rest during raising of the containers to the raised position, and via suction caps provided in the supporting surface, which abut against the bottom portions of the containers.

13. The process according to claim 11, wherein the vertical displacement device comprises a clamping device for clamping the containers laterally and retracting them to the carrier to the regular arrangement after the treatment or processing.

14. The process according to claim 11, wherein the vertical displacement device comprises a clamping device for pushing the containers downward to the carrier to the regular arrangement after the treatment or processing.

15. A process for sealing containers that contain substances for medical, pharmaceutical or cosmetic applications, comprising
   conveying the containers, by a conveyor, past at least one processing station for the treatment or processing while the containers are held by a carrier in a regular arrangement;
   filling the containers with the substance while being held by the carrier;
   pushing caps onto the upper rims of the containers while being held by the carrier; and
   displacing the caps and the containers in axial direction relative to each other to press down the caps onto the containers while the bottoms of the containers are supported on a supporting surface for sealing the containers with the caps, wherein
   the containers are supported by the carrier so that the bottoms of the containers are freely and completely accessible from the underside of the carrier,
   the containers are subjected to a freeze-drying process after the step of filling while being held by the carrier by bringing the bottoms of the containers into direct contact with one of a plurality of cooling surfaces or cooling fingers of a freeze-dryer,
   the internal volumes of the containers communicate with the environment via the caps positioned on the upper rims of the containers during the freeze-drying,
   the plurality of cooling surfaces or cooling fingers of the freeze-dryer together with the containers directly supported thereon are stacked one above the other, and
   the cooling surfaces or cooling fingers of the freeze-dryer are pressed against each other for pushing down the caps of the containers and sealing the containers with the caps.

16. The process according to claim 15, wherein
   the internal volumes of the containers communicate with the environment via the caps positioned on the upper rims of the containers,
   the containers are filled with the substance via the caps positioned on the upper rims of the containers, and
   the containers are sealed after pushing down the caps.

17. The process according to claim 15, wherein the caps are pushed onto the upper rims of the containers after the step of filling so that the internal volumes of the containers communicate with the environment via the caps positioned on the upper rims of the containers.

18. The process according to claim 15, wherein
   the containers are held in openings or receptacles of the carrier in the regular arrangement,
   at least two resilient holding tabs are respectively associated with the openings of receptacles, and
   the containers are each held by the holding tabs in the region of a constricted neck portion below an expanded upper rim at a top end of the respective container with radial clearance and with axial clearance so as to be freely displaceable in axial direction.

19. The process according to claim 18, further comprising slanted insertion surfaces that are formed at upper ends of the holding tabs, which are respectively followed by holding noses projecting from the holding tabs radially inwards.

20. The process according to claim 19, wherein the containers are weighed before and after the step of filling for obtaining information on the amount filled-in, which is associated to the individual containers and traced back by a software or by inscription or marking.

21. The process according to claim 20, wherein the containers are lifted for the step of weighing vertically upwards to a raised position using a vertical displacement device and are lowered after the step of weighing to be held again by the carrier in the openings or receptacles and in the regular arrangement.

22. The process according to claim 21, wherein the containers are weighed in the raised position while being held in the openings or receptacles of the carrier by the at least two resilient holding arms.

23. The process according to claim 21, wherein the containers are weighed in the raised position by a weighing device that is integrated into the vertical displacement device.

24. The process according to claim 21, wherein the vertical displacement device comprises a plurality of lifting rods that are aligned along a line and simultaneously raise a number of containers to the raised position.

25. The process according to claim 24, wherein the vertical displacement device further comprises a positioning device for positioning the lifting rods relative to the carrier together with the containers held thereon.

26. The process according to claim 25, wherein
   the vertical displacement device further comprises a negative pressure generating device for retracting the containers by a negative pressure acting on the bottom portions of the containers, and
   the negative pressure generating device is coupled to the vertical displacement device in such a manner that the negative pressure acts on the bottom portions of the containers via supporting surfaces provided at an upper end of the vertical displacement device, on which the bottom portions of the containers rest during raising of the containers to the raised position, and via suction caps provided in the supporting surface, which abut against the bottom portions of the containers.

27. The process according to claim 25, wherein the vertical displacement device comprises a clamping device for clamping the containers laterally and retracting them to the carrier to the regular arrangement after the treatment or processing.

28. The process according to claim 25, wherein the vertical displacement device comprises a clamping device for pushing the containers downward to the carrier to the regular arrangement after the treatment or processing.

* * * * *